United States Patent
Johnson et al.

(10) Patent No.: US 12,419,644 B2
(45) Date of Patent: Sep. 23, 2025

(54) BLOOD FLOW CONTROL DEVICES, SYSTEMS, AND METHODS AND ERROR DETECTION THEREOF

(71) Applicants: Certus Critical Care, Inc., Sacramento, CA (US); Wake Forest University Health Sciences, Winston-Salem, NC (US)

(72) Inventors: Michael Austin Johnson, Holladay, UT (US); David Poisner, Carmichael, CA (US); Melanie Mcwade, Portland, OR (US); Timothy Williams, Winston-Salem, NC (US); Lucas Neff, Winston-Salem, NC (US)

(73) Assignees: Certus Critical Care, Inc., Salt Lake City, UT (US); Wake Forest University Health Sciences, Winston-Salem, NC (US)

( * ) Notice: Subject to any disclaimer, the term of this patent is extended or adjusted under 35 U.S.C. 154(b) by 879 days.

(21) Appl. No.: 17/203,742

(22) Filed: Mar. 16, 2021

(65) Prior Publication Data
US 2021/0322026 A1    Oct. 21, 2021

Related U.S. Application Data

(60) Provisional application No. 62/990,302, filed on Mar. 16, 2020.

(51) Int. Cl.
A61B 17/12    (2006.01)
A61B 5/00     (2006.01)
(Continued)

(52) U.S. Cl.
CPC .... A61B 17/12136 (2013.01); A61B 5/02158 (2013.01); A61B 5/4836 (2013.01);
(Continued)

(58) Field of Classification Search
CPC .......... A61B 17/12136; A61B 5/02158; A61B 5/4836; A61B 17/12109; A61B 34/25;
(Continued)

(56) References Cited

U.S. PATENT DOCUMENTS 2,156,289 A    5/1939    Hoy
3,467,101 A    9/1969    Fogarty et al.
(Continued)

FOREIGN PATENT DOCUMENTS

AU    2015201978 A1    5/2015
AU    2015274743 B2    11/2016
(Continued)

OTHER PUBLICATIONS

Adelson, P. David, et al., "Guidelines for the acute medical management of severe traumatic brain injury in infants, children, and adolescents. Chapter 1: Introduction", Pediatric Critical Care Medicine (Jul. 2003); 4(3 Suppl): S2-4.
(Continued)

*Primary Examiner* — Richard G Louis
(74) *Attorney, Agent, or Firm* — COOLEY LLP

(57) ABSTRACT

Systems and methods for blood flow control are described herein. In some variations, a blood flow control system may comprise a blood flow control device. The blood flow control device may be placed within a body of a patient and may comprise an expandable member and a sensor. The sensor may be configured to measure at least one of a physiologic condition of the patient and a pressure associated with the expandable member. The blood flow control system may include at least one controller communicably coupled to the sensor to: receive data indicative of at least one of the physiologic condition of the patient and the pressure associated with the expandable member from the sensor, compare the received data with target data, identify
(Continued)

at least one error based on the comparison, and in response to identifying the error, inhibit at least one function of the blood flow control system.

39 Claims, 17 Drawing Sheets

(51) Int. Cl.
    *A61B 5/0215*     (2006.01)
    *A61B 34/00*     (2016.01)
    *A61B 17/00*     (2006.01)
    *A61B 34/20*     (2016.01)
    *A61B 90/00*     (2016.01)

(52) U.S. Cl.
    CPC ........ *A61B 17/12109* (2013.01); *A61B 34/25* (2016.02); *A61B 2017/00022* (2013.01); *A61B 2017/00075* (2013.01); *A61B 2017/00119* (2013.01); *A61B 2017/00557* (2013.01); *A61B 34/20* (2016.02); *A61B 2090/064* (2016.02)

(58) Field of Classification Search
    CPC .......... A61B 34/20; A61B 2017/00022; A61B 2017/00075; A61B 2017/00119; A61B 2017/00557; A61B 2090/064; A61B 2560/0257; A61B 2560/2576; A61B 5/6853; A61B 5/746; A61B 2017/00398; A61B 2017/00725; A61B 2017/00734; A61B 2090/0809; A61B 17/12036; A61B 17/1204; A61M 60/295; A61M 60/31; A61M 60/531; A61M 60/585; A61M 60/497; A61M 60/538; A61M 60/139
    See application file for complete search history.

(56) References Cited

U.S. PATENT DOCUMENTS

| | | |
|---|---|---|
| 3,791,374 A | 2/1974 | Guarino |
| 4,396,385 A | 8/1983 | Kelly et al. |
| 4,464,172 A | 8/1984 | Lichtenstein |
| 4,691,708 A | 9/1987 | Kane |
| 4,713,888 A | 12/1987 | Broselow |
| 4,777,951 A | 10/1988 | Cribier et al. |
| 4,823,469 A | 4/1989 | Broselow |
| 4,846,174 A | 7/1989 | Willard et al. |
| 4,865,549 A | 9/1989 | Sonsteby |
| 4,926,885 A | 5/1990 | Hinkle |
| 4,983,166 A | 1/1991 | Yamawaki |
| 5,047,045 A | 9/1991 | Arney et al. |
| 5,087,246 A | 2/1992 | Smith |
| 5,135,494 A | 8/1992 | Engelson et al. |
| 5,152,776 A | 10/1992 | Pinchuk |
| 5,158,529 A | 10/1992 | Kanai |
| 5,169,386 A | 12/1992 | Becker et al. |
| 5,217,456 A | 6/1993 | Narciso, Jr. |
| 5,282,479 A | 2/1994 | Havran |
| 5,320,605 A | 6/1994 | Sahota |
| 5,344,398 A * | 9/1994 | Hara ...................... A61B 18/18 604/21 |
| 5,383,856 A | 1/1995 | Bersin |
| 5,447,503 A | 9/1995 | Miller |
| 5,486,192 A | 1/1996 | Walinsky et al. |
| 5,505,702 A | 4/1996 | Arney |
| 5,522,400 A | 6/1996 | Williams |
| 5,558,644 A | 9/1996 | Boyd et al. |
| 5,571,093 A | 11/1996 | Cruz et al. |
| 5,607,394 A | 3/1997 | Andersen et al. |
| 5,678,570 A | 10/1997 | Manning |
| 5,718,678 A | 2/1998 | Fleming, III |
| 5,738,652 A | 4/1998 | Boyd et al. |
| 5,779,731 A | 7/1998 | Leavitt |
| 5,911,702 A | 6/1999 | Romley et al. |
| 6,011,988 A | 1/2000 | Lynch et al. |
| 6,013,019 A | 1/2000 | Fischell et al. |
| 6,042,532 A | 3/2000 | Freed et al. |
| 6,102,930 A | 8/2000 | Simmons, Jr. |
| 6,113,579 A | 9/2000 | Eidenschink et al. |
| 6,146,370 A | 11/2000 | Barbut |
| 6,161,547 A | 12/2000 | Barbut |
| 6,165,199 A | 12/2000 | Barbut |
| 6,190,304 B1 | 2/2001 | Downey et al. |
| 6,190,356 B1 | 2/2001 | Bersin |
| 6,231,551 B1 | 5/2001 | Barbut |
| 6,231,572 B1 | 5/2001 | Hart et al. |
| 6,248,083 B1 | 6/2001 | Smith et al. |
| 6,248,121 B1 | 6/2001 | Nobles |
| 6,254,569 B1 | 7/2001 | O'Donnell et al. |
| 6,280,434 B1 | 8/2001 | Kinoshita et al. |
| 6,315,768 B1 | 11/2001 | Wallace |
| 6,394,977 B1 | 5/2002 | Taylor et al. |
| 6,423,031 B1 | 7/2002 | Donlon |
| 6,453,572 B2 | 9/2002 | Cross et al. |
| 6,565,552 B1 | 5/2003 | Barbut |
| 6,575,932 B1 | 6/2003 | O'Brien et al. |
| 6,579,221 B1 | 6/2003 | Peterson |
| 6,592,557 B2 | 7/2003 | Barbut |
| 6,602,270 B2 | 8/2003 | Leschinsky et al. |
| 6,620,128 B1 | 9/2003 | Simhambhatla |
| 6,635,046 B1 | 10/2003 | Barbut |
| 6,656,153 B1 | 12/2003 | Sakai et al. |
| 6,666,814 B2 | 12/2003 | Downey et al. |
| 6,669,679 B1 | 12/2003 | Savage et al. |
| 6,679,860 B2 | 1/2004 | Stiger |
| 6,695,811 B2 | 2/2004 | Samson et al. |
| 6,712,806 B2 | 3/2004 | St. Germain et al. |
| 6,719,270 B2 | 4/2004 | Ozawa |
| 6,719,720 B1 | 4/2004 | Voelker et al. |
| 6,733,513 B2 | 5/2004 | Boyle et al. |
| 6,735,532 B2 | 5/2004 | Freed et al. |
| 6,736,790 B2 | 5/2004 | Barbut et al. |
| 6,743,196 B2 | 6/2004 | Barbut et al. |
| 6,746,462 B1 | 6/2004 | Selmon et al. |
| 6,767,345 B2 | 7/2004 | St. Germain et al. |
| 6,796,959 B2 | 9/2004 | Davis et al. |
| 6,796,992 B2 | 9/2004 | Barbut |
| 6,848,448 B1 | 2/2005 | St. Germain et al. |
| 6,868,739 B1 | 3/2005 | Krivitski et al. |
| 6,936,056 B2 | 8/2005 | Nash et al. |
| 6,979,318 B1 | 12/2005 | McDonald et al. |
| 7,166,097 B2 | 1/2007 | Barbut |
| 7,229,403 B2 | 6/2007 | Schock et al. |
| 7,341,571 B1 | 3/2008 | Harris et al. |
| 7,434,326 B2 | 10/2008 | Gifford |
| 7,468,027 B2 | 12/2008 | Barbut et al. |
| 7,503,904 B2 | 3/2009 | Choi |
| 7,503,909 B2 | 3/2009 | Kusu et al. |
| 7,763,043 B2 | 7/2010 | Goodin et al. |
| 7,867,195 B2 | 1/2011 | Barbut et al. |
| 7,888,740 B2 | 2/2011 | Tsutsumi et al. |
| 7,892,469 B2 | 2/2011 | Lim et al. |
| 7,909,810 B2 | 3/2011 | Noone |
| 7,927,346 B2 | 4/2011 | Vancamp et al. |
| 7,951,186 B2 | 5/2011 | Eidenschink et al. |
| 7,951,819 B2 | 5/2011 | Niculescu-Duvaz et al. |
| 7,959,644 B2 | 6/2011 | Shriver |
| 7,993,324 B2 | 8/2011 | Barbut |
| 8,088,103 B2 | 1/2012 | Teeslink et al. |
| 8,088,121 B2 | 1/2012 | Nishide et al. |
| 8,162,879 B2 | 4/2012 | Hattangadi et al. |
| 8,241,241 B2 | 8/2012 | Evans et al. |
| 8,262,611 B2 | 9/2012 | Teeslink et al. |
| 8,419,648 B2 | 4/2013 | Corl et al. |
| 8,430,899 B2 | 4/2013 | Dae et al. |
| 8,499,681 B2 | 8/2013 | Kanner et al. |
| 8,545,382 B2 | 10/2013 | Suzuki et al. |
| 8,628,461 B2 | 1/2014 | Mohl |
| 8,655,798 B2 | 2/2014 | Humphrey et al. |
| 8,672,868 B2 | 3/2014 | Simons |
| 8,672,930 B2 | 3/2014 | Wittenberger |
| 8,747,358 B2 | 6/2014 | Trombley, III et al. |
| 8,790,297 B2 | 7/2014 | Bromander et al. |

(56) References Cited

U.S. PATENT DOCUMENTS

| | | |
|---|---|---|
| 8,814,900 B2 | 8/2014 | Fleming, III |
| 8,888,740 B2 | 11/2014 | Barbut et al. |
| 8,900,214 B2 | 12/2014 | Nance et al. |
| 8,948,848 B2 | 2/2015 | Merhi |
| 8,951,565 B2 | 2/2015 | Mccarthy |
| 8,961,426 B2 | 2/2015 | Martin et al. |
| 9,108,000 B2 | 8/2015 | Kassab |
| 9,131,874 B2 | 9/2015 | Eliason et al. |
| D748,257 S | 1/2016 | Franklin |
| 9,393,384 B1 | 7/2016 | Kapur et al. |
| 9,402,952 B2 | 8/2016 | Beyersdorf |
| 9,414,843 B2 | 8/2016 | Pavcnik et al. |
| 9,474,882 B2 | 10/2016 | Franklin |
| 9,492,084 B2 | 11/2016 | Behar et al. |
| 9,682,217 B2 | 6/2017 | Franklin et al. |
| 9,687,333 B2 | 6/2017 | Angel et al. |
| 10,004,622 B2 | 6/2018 | Sanati et al. |
| 10,111,669 B2 | 10/2018 | Eliason et al. |
| 10,143,789 B2 | 12/2018 | Frost |
| 10,149,962 B2 | 12/2018 | Franklin et al. |
| 10,188,345 B2 | 1/2019 | Venkatraman et al. |
| 10,232,142 B2 | 3/2019 | Franklin |
| 10,279,094 B2 | 5/2019 | Williams et al. |
| 10,279,152 B2 | 5/2019 | Kapur et al. |
| 10,335,152 B2 | 7/2019 | Barbut et al. |
| 10,368,872 B2 | 8/2019 | Franklin et al. |
| 10,569,062 B2 | 2/2020 | Franklin |
| 10,758,715 B2 | 9/2020 | Kapur et al. |
| 10,765,841 B2 | 9/2020 | Zhadkevich |
| 10,806,903 B2 | 10/2020 | Franklin et al. |
| 10,842,975 B2 | 11/2020 | Kapur et al. |
| 10,881,770 B2 | 1/2021 | Tuval et al. |
| 10,885,813 B2 | 1/2021 | Krummenacher et al. |
| 11,013,515 B2 | 5/2021 | Zhadkevich |
| 11,058,864 B2 | 7/2021 | Frost |
| 11,135,408 B2 | 10/2021 | Schwartz et al. |
| 11,154,690 B2 | 10/2021 | Avneri et al. |
| 11,253,264 B2 | 2/2022 | Franklin et al. |
| 11,311,365 B2 | 4/2022 | Zhadkevich |
| 11,464,703 B2 | 10/2022 | Johnson et al. |
| 11,596,411 B2 | 3/2023 | Johnson et al. |
| 11,602,592 B2 | 3/2023 | Johnson et al. |
| 11,633,192 B2 | 4/2023 | Johnson et al. |
| 11,672,951 B2 | 6/2023 | Franklin et al. |
| 11,857,737 B2 | 1/2024 | Franklin et al. |
| 12,251,111 B2 | 3/2025 | Johnson |
| 2002/0007146 A1 | 1/2002 | Omaleki et al. |
| 2002/0062119 A1 | 5/2002 | Zadno-Azizi |
| 2002/0072647 A1 | 6/2002 | Schock et al. |
| 2002/0115982 A1 | 8/2002 | Barbut et al. |
| 2002/0193735 A1 | 12/2002 | Stiger |
| 2003/0023200 A1 | 1/2003 | Barbut et al. |
| 2003/0032974 A1 | 2/2003 | Leschinsky et al. |
| 2003/0167038 A1 | 9/2003 | Yozu et al. |
| 2003/0226568 A1 | 12/2003 | McKinley et al. |
| 2004/0073162 A1 | 4/2004 | Bleam et al. |
| 2004/0082935 A1 | 4/2004 | Lee et al. |
| 2004/0097813 A1 | 5/2004 | Williams |
| 2004/0111006 A1* | 6/2004 | Alferness ............ A61M 60/295 600/16 |
| 2004/0111016 A1 | 6/2004 | Casscells et al. |
| 2004/0254483 A1 | 12/2004 | Zdeblick et al. |
| 2004/0254528 A1 | 12/2004 | Adams et al. |
| 2005/0015048 A1 | 1/2005 | Chiu et al. |
| 2005/0059931 A1 | 3/2005 | Garrison et al. |
| 2005/0148812 A1 | 7/2005 | Nigroni et al. |
| 2005/0234293 A1* | 10/2005 | Yamamoto ............ A61B 90/57 600/102 |
| 2005/0261725 A1 | 11/2005 | Crawford et al. |
| 2006/0064059 A1 | 3/2006 | Gelfand et al. |
| 2006/0100639 A1 | 5/2006 | Levin et al. |
| 2006/0287569 A1 | 12/2006 | Schock et al. |
| 2007/0043307 A1 | 2/2007 | Raulerson et al. |
| 2007/0043409 A1 | 2/2007 | Brian, III et al. |
| 2007/0106258 A1 | 5/2007 | Chiu et al. |
| 2007/0118095 A1 | 5/2007 | Barbut |
| 2007/0129466 A1 | 6/2007 | Kagawa et al. |
| 2007/0135830 A1 | 6/2007 | Schaeffer |
| 2007/0208291 A1 | 9/2007 | Patel |
| 2007/0219441 A1 | 9/2007 | Carlin et al. |
| 2007/0219466 A1 | 9/2007 | Tremulis et al. |
| 2007/0219488 A1 | 9/2007 | Francescatti |
| 2007/0270935 A1 | 11/2007 | Newhauser et al. |
| 2008/0027356 A1 | 1/2008 | Chen et al. |
| 2008/0051764 A1 | 2/2008 | Dent et al. |
| 2008/0082046 A1 | 4/2008 | Kato et al. |
| 2008/0082119 A1 | 4/2008 | Vitullo |
| 2008/0097300 A1 | 4/2008 | Eskaros et al. |
| 2008/0178882 A1 | 7/2008 | Christopher et al. |
| 2008/0188803 A1 | 8/2008 | Jang |
| 2008/0243067 A1 | 10/2008 | Rottenberg et al. |
| 2008/0243221 A1 | 10/2008 | Arcand |
| 2008/0262477 A1 | 10/2008 | Djaladat |
| 2009/0012467 A1 | 1/2009 | Suzuki et al. |
| 2009/0026595 A1 | 1/2009 | Kadoi |
| 2009/0062666 A1 | 3/2009 | Roteliuk |
| 2009/0156978 A1* | 6/2009 | Faul ...................... A61B 17/11 604/9 |
| 2009/0171222 A1* | 7/2009 | Valdes ................... A61B 5/022 600/490 |
| 2009/0171272 A1 | 7/2009 | Tegg et al. |
| 2009/0171293 A1 | 7/2009 | Yang et al. |
| 2009/0265951 A1 | 10/2009 | Black |
| 2009/0287079 A1 | 11/2009 | Shriver |
| 2009/0312807 A1 | 12/2009 | Boudreault et al. |
| 2010/0016735 A1 | 1/2010 | Harpas et al. |
| 2010/0041984 A1 | 2/2010 | Shapland et al. |
| 2010/0113939 A1* | 5/2010 | Mashimo ........ A61M 25/10187 600/488 |
| 2010/0234915 A1 | 9/2010 | Herlich et al. |
| 2010/0262076 A1 | 10/2010 | Rowe et al. |
| 2010/0268017 A1 | 10/2010 | Siess |
| 2010/0280451 A1 | 11/2010 | Teeslink et al. |
| 2010/0292635 A1 | 11/2010 | Sundar |
| 2010/0318114 A1 | 12/2010 | Pranevicius et al. |
| 2011/0034768 A1 | 2/2011 | Ozaki et al. |
| 2011/0144742 A1 | 6/2011 | Madrid et al. |
| 2011/0196412 A1 | 8/2011 | Levit et al. |
| 2011/0230821 A1 | 9/2011 | Babic |
| 2011/0295177 A1 | 12/2011 | Mohl |
| 2011/0295301 A1 | 12/2011 | Hoem et al. |
| 2011/0295302 A1 | 12/2011 | Mohl |
| 2011/0301630 A1 | 12/2011 | Hendriksen et al. |
| 2012/0101413 A1 | 4/2012 | Beetel et al. |
| 2012/0108979 A1 | 5/2012 | Franklin et al. |
| 2012/0109057 A1 | 5/2012 | Krolik et al. |
| 2012/0116352 A1 | 5/2012 | Rangi |
| 2012/0130359 A1 | 5/2012 | Turovskiy |
| 2012/0172911 A1 | 7/2012 | Welch |
| 2012/0209176 A1 | 8/2012 | Anderson |
| 2012/0215166 A1 | 8/2012 | Barki |
| 2012/0220884 A1* | 8/2012 | Yamashita ............. A61B 5/022 600/490 |
| 2012/0271231 A1 | 10/2012 | Agrawal |
| 2012/0302994 A1 | 11/2012 | Wilson et al. |
| 2013/0060316 A1 | 3/2013 | Sanati et al. |
| 2013/0102926 A1 | 4/2013 | Eliason et al. |
| 2013/0102929 A1 | 4/2013 | Haight et al. |
| 2013/0172786 A1 | 7/2013 | Olson et al. |
| 2013/0178750 A1 | 7/2013 | Sheehan et al. |
| 2013/0190619 A1 | 7/2013 | Nudel |
| 2013/0190633 A1 | 7/2013 | Dorando et al. |
| 2013/0281787 A1 | 10/2013 | Avneri et al. |
| 2013/0281869 A1 | 10/2013 | Barbut et al. |
| 2013/0289607 A1 | 10/2013 | Pedersen et al. |
| 2013/0338637 A1 | 12/2013 | Fischer, Jr. et al. |
| 2014/0221898 A1 | 8/2014 | Kurrus et al. |
| 2014/0243873 A1 | 8/2014 | Franklin |
| 2014/0249504 A1 | 9/2014 | Franklin et al. |
| 2014/0249573 A1* | 9/2014 | Arav ..................... A61B 17/42 606/202 |
| 2014/0316012 A1 | 10/2014 | Freyman et al. |
| 2014/0323846 A1 | 10/2014 | Niebel et al. |
| 2014/0350523 A1 | 11/2014 | Dehdashtian et al. |

(56) References Cited

U.S. PATENT DOCUMENTS

| | | |
|---|---|---|
| 2014/0364835 A1 | 12/2014 | Allen et al. |
| 2014/0378869 A1 | 12/2014 | Sela et al. |
| 2015/0011900 A1* | 1/2015 | Lu .................. A61B 5/0022 |
| | | 600/490 |
| 2015/0012031 A1 | 1/2015 | Rago et al. |
| 2015/0039012 A1 | 2/2015 | Solar et al. |
| 2015/0133892 A1 | 5/2015 | Joe et al. |
| 2015/0157326 A1 | 6/2015 | Schiemanck et al. |
| 2015/0165174 A1 | 6/2015 | Helkowski et al. |
| 2015/0245867 A1 | 9/2015 | Gross |
| 2015/0272732 A1 | 10/2015 | Tilson et al. |
| 2015/0290372 A1 | 10/2015 | Muller et al. |
| 2015/0327836 A1 | 11/2015 | Stone et al. |
| 2015/0367098 A1 | 12/2015 | Aggerholm et al. |
| 2016/0000446 A1 | 1/2016 | Eliason et al. |
| 2016/0029995 A1 | 2/2016 | Navratil et al. |
| 2016/0166197 A1 | 6/2016 | Venkatraman et al. |
| 2016/0206798 A1 | 7/2016 | Williams et al. |
| 2016/0213893 A1 | 7/2016 | Franklin |
| 2016/0262647 A1 | 9/2016 | Berenfeld |
| 2016/0310103 A1 | 10/2016 | Liu et al. |
| 2016/0375230 A1 | 12/2016 | Lee et al. |
| 2017/0043123 A1 | 2/2017 | Franklin |
| 2017/0049946 A1 | 2/2017 | Kapur et al. |
| 2017/0164876 A1 | 6/2017 | Hyde et al. |
| 2017/0245794 A1 | 8/2017 | Sharma et al. |
| 2017/0266379 A1 | 9/2017 | Harrity |
| 2017/0348049 A1 | 12/2017 | Vrba et al. |
| 2017/0368313 A1 | 12/2017 | Franklin et al. |
| 2018/0064350 A1 | 3/2018 | Thakur et al. |
| 2018/0146872 A1 | 5/2018 | Shaknovich |
| 2018/0147375 A1 | 5/2018 | Johnson et al. |
| 2018/0154129 A1 | 6/2018 | Paul et al. |
| 2018/0193650 A1 | 7/2018 | Srivastava et al. |
| 2018/0228951 A1 | 8/2018 | Schwammenthal et al. |
| 2018/0236203 A1 | 8/2018 | Franklin et al. |
| 2018/0243541 A1 | 8/2018 | Kapur et al. |
| 2019/0015630 A1 | 1/2019 | Franklin et al. |
| 2019/0046762 A1 | 2/2019 | Rogers et al. |
| 2019/0046769 A1 | 2/2019 | Avneri et al. |
| 2019/0076152 A1 | 3/2019 | Franklin et al. |
| 2019/0126014 A1 | 5/2019 | Kapur et al. |
| 2019/0290845 A1 | 9/2019 | List |
| 2019/0307462 A1 | 10/2019 | Franklin et al. |
| 2019/0336665 A1 | 11/2019 | Frost |
| 2019/0378436 A1 | 12/2019 | Krummenacher et al. |
| 2020/0038566 A1 | 2/2020 | Johnson et al. |
| 2020/0046364 A1 | 2/2020 | Johnson et al. |
| 2020/0054520 A1 | 2/2020 | Johnson et al. |
| 2020/0163707 A1 | 5/2020 | Sliwa et al. |
| 2020/0238018 A1 | 7/2020 | Lee et al. |
| 2020/0276419 A1 | 9/2020 | Franklin et al. |
| 2020/0329995 A1 | 10/2020 | Stone et al. |
| 2020/0375603 A1 | 12/2020 | Parekh et al. |
| 2021/0030423 A1 | 2/2021 | Starnes |
| 2021/0038229 A1 | 2/2021 | Radl et al. |
| 2021/0045864 A1 | 2/2021 | Pelssers et al. |
| 2021/0212697 A1 | 7/2021 | Frost et al. |
| 2021/0236136 A1 | 8/2021 | Mohl et al. |
| 2021/0275783 A1 | 9/2021 | Johnson et al. |
| 2021/0290243 A1 | 9/2021 | Franklin et al. |
| 2021/0330959 A1 | 10/2021 | Frost |
| 2021/0338245 A1 | 11/2021 | Johnson et al. |
| 2021/0353298 A1 | 11/2021 | Williams et al. |
| 2021/0370025 A1 | 12/2021 | Pickering et al. |
| 2022/0323083 A1 | 10/2022 | Franklin et al. |
| 2022/0401709 A1 | 12/2022 | Beeby et al. |
| 2023/0001141 A1 | 1/2023 | Franklin et al. |
| 2023/0079117 A1 | 3/2023 | Beeby et al. |
| 2023/0138661 A1 | 5/2023 | Mohlin et al. |
| 2023/0270444 A1 | 8/2023 | Fong et al. |
| 2023/0338037 A1 | 10/2023 | Johnson |
| 2023/0355866 A1 | 11/2023 | Johnson et al. |
| 2023/0380702 A1 | 11/2023 | Poisner |
| 2023/0414220 A1 | 12/2023 | Johnson et al. |
| 2023/0414221 A1 | 12/2023 | Franklin et al. |
| 2024/0165380 A1 | 5/2024 | Williams et al. |

FOREIGN PATENT DOCUMENTS

| | | |
|---|---|---|
| AU | 2014223477 B2 | 2/2017 |
| AU | 2014223556 B2 | 5/2017 |
| AU | 2016232781 B2 | 11/2017 |
| AU | 2017272335 B2 | 6/2018 |
| AU | 2014317859 B2 | 5/2019 |
| CA | 2941438 A1 | 12/2015 |
| CA | 2980018 A1 | 9/2016 |
| CA | 2990479 A1 | 12/2017 |
| CN | 1216929 A | 5/1999 |
| CN | 102740906 A | 10/2012 |
| CN | 105339035 A | 2/2016 |
| CN | 105792879 A | 7/2016 |
| DE | 3424552 A1 | 1/1986 |
| EM | 0026882830001 | 3/2019 |
| EP | 0188467 A1 | 7/1986 |
| EP | 1094861 B1 | 4/2005 |
| EP | 1658808 A1 | 5/2006 |
| EP | 1911484 A2 | 4/2008 |
| EP | 2308541 A1 | 4/2011 |
| EP | 2347726 A2 | 7/2011 |
| EP | 2389974 A1 | 11/2011 |
| EP | 2716323 A1 | 4/2014 |
| EP | 2837402 A2 | 2/2015 |
| EP | 3148603 B1 | 1/2018 |
| EP | 3260158 B1 | 11/2018 |
| EP | 3270997 B1 | 7/2019 |
| EP | 3560416 A1 | 10/2019 |
| EP | 3424552 B1 | 4/2020 |
| EP | 2961464 B1 | 5/2020 |
| EP | 3549121 B1 | 9/2021 |
| FR | 2961464 A1 | 12/2011 |
| GB | 902441 A | 8/1962 |
| GB | 2297259 A | 7/1996 |
| GB | 90026882830001 | 4/2015 |
| IL | 240775 B | 11/2018 |
| JP | H03198868 A | 8/1991 |
| JP | H03280962 A | 12/1991 |
| JP | H09164208 A | 6/1997 |
| JP | H1080497 A | 3/1998 |
| JP | 2000217922 A | 8/2000 |
| JP | 2002505165 A | 2/2002 |
| JP | 2002505919 A | 2/2002 |
| JP | 2003079738 A | 3/2003 |
| JP | 2003535652 A | 12/2003 |
| JP | 2004533290 A | 11/2004 |
| JP | 2007014820 A | 1/2007 |
| JP | 2008237529 A | 10/2008 |
| JP | 2008546471 A | 12/2008 |
| JP | 2010538797 A | 12/2010 |
| JP | 2011055942 A | 3/2011 |
| JP | 2011245300 A | 12/2011 |
| JP | 2013042912 A | 3/2013 |
| JP | 2015120088 A | 7/2015 |
| JP | 2017516624 A | 6/2017 |
| JP | 6286564 B2 | 2/2018 |
| JP | 6343009 B2 | 6/2018 |
| JP | 6343290 B2 | 6/2018 |
| JP | 6345192 B2 | 6/2018 |
| JP | 2018523534 A | 8/2018 |
| JP | 6408176 B2 | 10/2018 |
| JP | 6472536 B2 | 2/2019 |
| WO | WO-9220398 A1 | 11/1992 |
| WO | WO-9713542 A1 | 4/1997 |
| WO | WO-9834670 A2 | 8/1998 |
| WO | WO-9924105 A2 | 5/1999 |
| WO | WO-9944666 A2 | 9/1999 |
| WO | WO-0078386 A1 | 12/2000 |
| WO | WO-0197743 A2 | 12/2001 |
| WO | WO-02085443 A1 | 10/2002 |
| WO | WO-2004049970 A2 | 6/2004 |
| WO | WO-2006014631 A1 | 2/2006 |
| WO | WO-2006135853 A2 | 12/2006 |
| WO | WO-2007001701 A1 | 1/2007 |

(56) References Cited

FOREIGN PATENT DOCUMENTS

| | | |
|---|---|---|
| WO | WO-2007022592 A1 | 3/2007 |
| WO | WO-2008013441 A1 | 1/2008 |
| WO | WO-2009039203 A2 | 3/2009 |
| WO | WO-2010030882 A1 | 3/2010 |
| WO | WO-2010070685 A1 | 6/2010 |
| WO | WO-2011133736 A2 | 10/2011 |
| WO | WO-2013/096548 A1 | 1/2013 |
| WO | WO-2013096713 A2 | 6/2013 |
| WO | WO-2014003809 A1 | 1/2014 |
| WO | WO-2014036530 A1 | 3/2014 |
| WO | WO-2014134215 A1 | 9/2014 |
| WO | WO-2014152191 A1 | 9/2014 |
| WO | WO-2014176668 A1 | 11/2014 |
| WO | WO-2015006828 A1 | 1/2015 |
| WO | WO-2015035393 A1 | 3/2015 |
| WO | WO-2015100393 A1 | 7/2015 |
| WO | WO-2015/181167 A1 | 12/2015 |
| WO | WO-2015191685 A1 | 12/2015 |
| WO | WO-2016126369 A1 | 8/2016 |
| WO | WO-2016/145163 A1 | 9/2016 |
| WO | WO-2016/149653 A2 | 9/2016 |
| WO | WO-2016/149653 A3 | 11/2016 |
| WO | WO-2016196837 A1 | 12/2016 |
| WO | WO-2017/210584 A1 | 12/2017 |
| WO | WO-2018089837 A1 | 5/2018 |
| WO | WO-2018/132623 A1 | 7/2018 |
| WO | WO-2018/195507 A1 | 10/2018 |
| WO | WO-2019195323 A1 | 10/2019 |
| WO | WO-2020/039083 A2 | 2/2020 |
| WO | WO-2020033372 A1 | 2/2020 |
| WO | WO-2020157648 A1 | 8/2020 |
| WO | WO-2021178937 A1 | 9/2021 |
| WO | WO-2021188602 A2 | 9/2021 |
| WO | WO-2022266397 A2 | 12/2022 |
| WO | WO-2023043513 A1 | 3/2023 |
| WO | WO-2023086344 A1 | 5/2023 |
| WO | WO-2023224679 A2 | 11/2023 |
| WO | WO-2023225110 A1 | 11/2023 |
| WO | WO-2023230630 A1 | 11/2023 |
| WO | WO-2024030319 A1 | 2/2024 |
| WO | WO-2024228736 A2 | 11/2024 |

OTHER PUBLICATIONS

[Author Unknown], "Technology Pipeline". Certus Critical Care Inc. (Retrieved on Jun. 17, 2022); [Online] Retrieved from the Internet, https://www.certuscriticalcare.com/technology-portfolio, 16 pages.

Bonnici, Maximilian, et al., "Successfully Stifling Retroperitoneal and Pelvic Exsanguination by Resuscitative Endovascular Balloon Occlusion of the Aorta in a Rural Setting", Journal of Endovascular Resuscitation and Trauma Management (2022); 6(2): 110-115.

Borzelli, Antonio, et al., "Successful Endovascular Embolisation of an Unusual Giant Pseudoaneurysm of the Middle Colic Artery", Journal of Endovascular Resuscitation and Trauma Management (2022); 6(2): 84-90.

Borzelli, Antonio, et al., "Successful Endovascular Management of a Massive Hemoptysis due to a Rare Oncological Giant Pulmonary Artery Pseudoaneurysm", Journal of Endovascular Resuscitation and Trauma Management (2022); 6(2): 91-96.

Certus Critical Care Presentation, "Beyond REBOA: An experimental model of Endovascular Variable Aortic Control (EVAC) using an automated extracorporeal circuit", Society for Military Surgeons' Boston (Mar. 2, 2016), 21 pages.

Certus Critical Care Presentation, "New Endovascular Techniques for Trauma: NextGenREBOA", Vienna Endovascular Trauma Meeting (Feb. 2016), 46 pages.

Chieregato, Arturo, et al., "Cerebral Blood Flow In Traumatic Contusions Is Predominantly Reduced after An Induced Acute Elevation Of Cerebral Perfusion Pressure", Neurosurgery (2007); 60(1): 115-123.

Davidson, Anders J., et al., "Small Adjustments, Big Effects: Physiologic Considerations for the Clinical Implementation of Next Generation Resuscitative Balloon Occlusion of the Aorta (REBOA)", Journal of the American College of Surgeons (Oct. 2016); 223(4): e218-e219.

Davidson, Anders J., et al., "Potential benefit of early operative utilization of low profile, partial resuscitative endovascular balloon occlusion of the aorta (P-REBOA) in major traumatic hemorrhage", Trauma Surgery & Acute Care Open (Aug. 2016); 1(1): e000028.

Detrano, Robert, et al., "Bayesian probability analysis: a prospective demonstration of its clinical utility in diagnosing coronary disease", (Mar. 1, 1984); Circulation 69(3): 541-547.

Dubose, Joe, "Evolving Paradigms in Vascular Injury Management", University of Maryland, Adams Crowley Shock Trauma Center (Mar. 17, 2016); 99 pages.

Fenton, Norman, et al., "Comparing risks of alternative medical diagnosis using Bayesian arguments", Journal of Biomedical Informatics (Aug. 2010); 43(4):485-495.

Gantner, Dashiell, et al., "Intravenous fluids in traumatic brain injury: what's the solution?", Current Opinion in Critical Care (Aug. 2014); 20(4): 385-389.

Guidance for the Use of Bayesian Statistics in Medical Device Clinical Trials, U.S. Department of Health and Human Services, Food and Drug Administration, Center for Devices and Radiological Health, Division of Biostatistics, Office of Surveillance and Biometrics, Feb. 5, 2010, 50 pages.

Hoareau, Guillaume L., et al., "Automated Partial Versus Complete Resuscitative Endovascular Balloon Occlusion of the Aorta for the Management of Hemorrhagic Shock in a Pig Model of Polytrauma: a Randomized Controlled Pilot Study", Military Medicine (Nov.-Dec. 2020); 185(11-12): e1923-e1930.

Holcomb, John B., et al., "Causes of Death in U.S. Special Operations Forces in the Global War on Terrorism: 2001-2004", Annals of Surgery (Jun. 2007); e245(6): 986-991.

International Preliminary Report on Patentability for International Application No. PCT/US2021/022644, mailed Sep. 20, 2022, 17 pages.

Invitation to Pay Additional Fees for International Application PCT/US2022/033898, mailed Oct. 25, 2022, 21 pages.

Kalogeris, Theodore, et al., "Cell Biology of Ischemia/Reperfusion Injury", International Review of Cell and Molecular Biology (2012); 298: 229-317.

Kochanek, Patrick M., et al., "Guidelines for the acute medical management of severe traumatic brain injury in infants, children, and adolescents—second edition", Pediatric Critical Care Medicine (2012); 13(1 Suppl): S1-S2.

Kochanek, Patrick M., et al. "Guidelines for the Management of Pediatric Severe Traumatic Brain Injury, Third Edition: Update of the Brain Trauma Foundation Guidelines", Pediatric Critical Care Medicine (Mar. 2019); 20(3S): S1-S82.

Leavesley, S. J. et al, "A device for performing automated balloon catheter inflation ischemia studies", Plos One (Apr. 25, 2014); 9(4): 9 pages.

Mcgreevy, David T, et al., "EndoVascular resuscitation and Trauma Management Specialists in Training—The Future of EVTM Education", Journal of Endovascular Resuscitation and Trauma Management (2022); 6(2): 77-78.

Mcgreevy, David T, et al., "The Use of a Single Proglide for Large Sheath Delivery Systems", Journal of Endovascular Resuscitation and Trauma Management (2022); 6(2): 116-118.

Mundasad, Smitha, "Balloon surgery stops fatal bleeding at roadside", BBC News, Jun. 17, 2014, [online], [retrieved on unknown]. Retrieved from the Internet URL: https://www.bbc.com/news/health-27868418, 3 pages.

Nieto-Calvache, Albaro José, et al., "Technical Considerations for the Use of REBOA in the Management of Placenta Accreta Spectrum", Journal of Endovascular Resuscitation and Trauma Management (2022); 6(2): 79-83.

Patel et al., "Bayesian Designs for Device Clinical Trials," MDG Forum, Waltham, MA., Nov. 3, 2010, downloaded from web page:http://www.cytel.com/pdfs/Pate1Bayes_Devices_Siides_11.18.10.pdf; 17 pages.

(56) References Cited

OTHER PUBLICATIONS

Patel, Nathan T. P., et al., "Endovascular Perfusion Augmentation for Critical Care Decreases Vasopressor Requirements while Maintaining Renal Perfusion", Shock: Injury, Inflammation, and Sepsis: Laboratory and Clinical Approaches 57(5); (May 1, 2022): 740-748.
PCT/US2021/021264, International Search Report and Written Opinion mailed Jun. 2, 2021, 17 pages.
PCT/US2021/021264, International Preliminary Report on Patentability, mailed Sep. 6, 2022, 16 pages.
PCT/US2022/033896, Invitation to Pay Additional Fees, mailed Oct. 6, 2022, 18 pages.
Peiniger, Sigune, et al., "Balanced massive transfusion ratios in multiple injury patients with traumatic brain injury", Critical Care (Feb. 22, 2011); 15(1): 1-9.
Rasmussen, Todd E., et al., "Ahead of the curve: Sustained innovation for future combat casualty care", Journal of Trauma and Acute Care Surgery 79.4 (Oct. 2015): S61-S64.
Russo, Rachel M., et al., "A pilot study of chest tube versus pigtail catheter drainage of acute hemothorax in swine", Journal of Trauma and Acute Care Surgery (Dec. 2015); 79(6): 1038-1043.
Safe Study Investigators, "Saline or Albumin for Fluid Resuscitation in Patients with Traumatic Brain Injury", New England Journal of Medicine (Aug. 30, 2007); 357(9): 874-884.
Sam II, Albert, et al., "Blunt traumatic aortic transection: endoluminal repair with commercially available aortic cuffs", Journal of Vascular Surgery (Nov. 2003); 38(5): 1132-1135.
Sandgren, Thomas, et al. "The diameter of the common femoral artery in healthy human: Influence of sex, age, and body size", Journal of Vascular Surgery (Mar. 1999); 29(3): 503-510.
Screen capture from YouTube video clip entitled "Evolving Paradigms In Vascular Injury Management—Joseph DuBose—M.D.," 1 page, uploaded on Sep. 12, 2017; Presented on Mar. 22, 2016 by user "Surgery Grand Rounds 2016". Retrieved from Internet: https://www.youtube.com/watch?v=YfSYEM797Gg.
Shehab, Maysam, et al., "REBOA and the Open Abdomen", Journal of Endovascular Resuscitation and Trauma Management (2022); 6(2): 97-101.
Sohn, Vance Y., et al., "Demographics, treatment, and early outcomes in penetrating vascular combat trauma", Archives of Surgery (Aug. 18, 2008); 143(8): 783-787.
Spinella, Philip C., et al., "The Association of Blood Component Use Ratios With the Survival of Massively Transfused Trauma Patients With and Without Severe Brain Injury", Journal of Trauma and Acute Care Surgery (Aug. 2011); 71(2): S343-S352.
Sugiyama, Takuya, et al., "Transcatheter Arterial Embolization for Blunt Hepatic Trauma in a Preschooler", Journal of Endovascular Resuscitation and Trauma Management (2022); 6(2): 106-109.
Sumislawski, Joshua J, et al., "Resuscitative Endovascular Balloon Occlusion of the Aorta as a Bridge to Organ Donation after Blunt Trauma", Journal of Endovascular Resuscitation and Trauma Management (2022); 6(2): 102-105.
U.S. Appl. No. 63/277,428, inventors Fabro; Myra et al., filed Nov. 9, 2021.
Weingart, Scott, MD FCCM; "Podcast 170—the ER REBOA Catheter with Joe DuBose", EMCrit Blog (Mar. 21, 2016); [Online] Accessed on Aug. 30, 2022; Retrieved from the Internet, https://emcrit.org/emcrit/er-reboa/, 3 pages.
Williams, Timothy Keith, et al., "Extending resuscitative endovascular balloon occlusion of the aorta: Endovascular variable aortic control in a lethal model of AQ1 hemorrhagic shock", Journal of Trauma and Acute Care Surgery (Apr. 30, 2016); 00(00): 1-8.
Abid et al. (2020). "Reperfusion repercussions: A review of the metabolic derangements following resuscitative endovascular balloon occlusion of the aorta." J Trauma Acute Care Surg vol. 89, No. 2, Supplement 2. pp. S39-S44.
Beyer et al. (2019). "Resuscitative Endovascular Balloon Occlusion of the Aorta (REBOA) Induced Myocardial Injury is Mitigated by Endovascular Variable Aortic Control (EVAC)." J Trauma Acute Care Surg. 87(3):590-8. doi:10.1097/TA.0000000000002363.
Beyer et al. (2019). "Resuscitative endovascular balloon occlusion of the aorta (REBOA) in a swine model of hemorrhagic shock and blunt thoracic injury." Eur J Trauma Emerg Surg. Published online. doi:10.1007/s00068-019-01185-3.
Curtis et al. (2019). "Resuscitative endovascular balloon occlusion of the aorta during non-ST elevation myocardial infarction: A case report." Trauma. 21(2): 147-151. doi:10.1177/1460408618767701.
Davidson et al. (2016). "Potential benefit of early operative utilization of low profile, partial resuscitative endovascular balloon occlusion of the aorta (P-REBOA) in major traumatic hemorrhage." Trauma surgery & acute care open. 1: 1-3.
Davidson et al. (2017). "A novel model of highly lethal uncontrolled torso hemorrhage in swine." J Surg Res. 218: 306-315. doi:10.1016/j.jss.2017.06.045.
Davidson et al. (2017). "Incremental balloon deflation following complete reboa results in steep inflection of flow and rapid reperfusion in a large animal model of hemorrhagic shock." J Trauma Acute Care Surg. 83(1):139. doi:10.1097/TA.0000000000001502.
Davidson et al. (2018). "The pitfalls of resuscitative endovascular balloon occlusion of the aorta: Risk factors and mitigation strategies." J Trauma Acute Care Surg. 84(1): 192. doi:10.1097/TA.0000000000001711A.
Extended European Search Report mailed on Sep. 17, 2020 for European Application No. 18738917.6, 8 pages.
Extended European Search Report mailed on Dec. 18, 2020 for European Application No. 18788177.6, 8 pages.
Forte et al. (2019). "Titrate to equilibrate and not exsanguinate! Characterization and validation of a novel partial resuscitative endovascular balloon occlusion of the aorta catheter in normal and hemorrhagic shock conditions." J Trauma Acute Care Surg. 87(5): 1015-1025. DOI: 10.1097/TA.0000000000002378.
Forte et al. (2020). "Validation of a novel partial resuscitative endovascular balloon occlusion of the aorta device in a swine hemorrhagic shock model: Fine tuning flow to optimize bleeding control and reperfusion injury." J Trauma Acute Care Surg. 89(1): 58-67.
Hoareau et al. (2018). "Acute Kidney Injury Following Resuscitative Aortic Occlusion: A Systematics Review." Journal of Endovascular Resuscitation and Trauma Management. 2(2): 57-65.
Hoareau et al. (2019). "Endocrine Effects of Simulated Complete and Partial Aortic Occlusion in a Swine Model of Hemorrhagic Shock." Mil Med. 184(5-6): e298-e302. doi:10.1093/milmed/usy287.
Hoareau et al. (2019). "Renal effects of three endoaortic occlusion strategies in a swine model of hemorrhagic shock." Injury. 50(11): 1908-1914. doi:10.1016/j.injury.2019.08.037.
Horeau et al. (2020). "Esmolol reduces myocardial injury induced by resuscitative endovascular balloon occlusion of the aorta (REBOA) in a porcine model of hemorrhagic shock." Injury. 51: 2165-2171.
Hoareau et al. (2020). "Automated partial versus complete resuscitative endovascular balloon occlusion of the aorta for the management of hemorrhagic shock in a pig model of polytrauma: a randomized controlled pilot study." Manuscript Draft submitted to Military Medicine on Mar. 6, 2020. 29 pages.
Johnson et al. (2016). "Partial resuscitative balloon occlusion of the aorta (P-REBOA): Clinical technique and rationale." J Trauma Acute Care Surg. vol. 81, No. 5, Supplement 1. S133-7. DOI: 10.1097/TA.0000000000001146.
Johnson et al. (2017). "The Effect of REBOA, Partial Aortic Occlusion and Aggressive Blood Transfusion on Traumatic Brain Injury in a Swine Polytrauma Model." J Trauma Acute Care Surg. 83(1):61. doi:10.1097/TA.0000000000001518.
Johnson et al. (2017). "Small changes, big effects: The hemodynamics of partial and complete aortic occlusion to inform next generation resuscitation techniques and technologies." J Trauma Acute Care Surg. 2017;82(6):1106-1111.
Johnson et al. (2019). "Endovascular perfusion augmentation for critical care: partial aortic occlusion for treatment of severe ischemia—reperfusion shock." Shock. 51(5): 659-66.
Johnson et al. (2020). "Letter to the Editor Re: Titrate to equilibrate and not exsanguinate!" J Trauma Acute Care Surg. 88(2): e107. doi:10.1097/TA.0000000000002528.

(56) References Cited

OTHER PUBLICATIONS

Johnson et al. (2020). "Response to the letter to the editor regarding: Titrate to equilibrate and not exsanguinate! Characterization and validation of a novel partial resuscitative endovascular balloon occlusion of the aorta catheter in normal and hemorrhagic shock conditions." J Trauma Acute Care Surg. 88(2): e108.
Johnson et al. (2020). "Letter to the Editor: Response to Letter from Dr. Martin et al.: Not Ready for Prime Time: Intermittent Versus Partial REBOA for Prolonged Hemorrhage Control In a Highly Lethal Porcine Injury Model." J Trauma Acute Care Surg. 88(6):e150-1. doi: 10.1097/TA.0000000000002629.
Johnson et al. (2020). "Not ready for prime time: Intermittent versus partial resuscitative endovascular balloon occlusion of the aorta for prolonged hemorrhage control in a highly lethal porcine injury model." J Trauma Acute Care Surg. 88(2): 298-304. doi:10.1097/TA.0000000000002558.
Kuckelman et al. (2018). "Extending the golden hour for Zone 1 resuscitative endovascular balloon occlusion of the aorta: Improved survival and reperfusion injury with intermittent versus continuous resuscitative endovascular balloon occlusion of the aorta of the aorta in a porcine severe truncal hemorrhage model." J Trauma Acute Care Surg. 85(2): 318-326.
Matsumura et al. (2019). "Distal pressure monitoring and titration with percent balloon volume: feasible management of partial resuscitative endovascular balloon occlusion of the aorta (P?REBOA)." European Journal of Trauma and Emergency Surgery. pp. 1-7. DOI: https://doi.org/10.1007/s00068-019-01257-4.
PCT/US2018/013413, International Search Report and Written Opinion mailed Apr. 4, 2018, 20 pages.
PCT/US2018/013413, International Preliminary Report on Patentability, mailed Jul. 16, 2019, 18 pages.
PCT/US2018/028694, International Search Report and Written Opinion mailed Jul. 9, 2018, 11 pages.
PCT/US2018/028694, International Preliminary Report on Patentability, mailed Oct. 22, 2019, 10 pages.
PCT/US2021/022644, Invitation to Pay Additional Fees, mailed Aug. 16, 2021, 25 pages.
Russo et al. (2016). "Emerging Endovascular Therapies for Non-Compressible Torso Hemorrhage." Shock Augusta Ga. 46(3 Suppl 1): 12-19. doi:10.1097/SHK.0000000000000641.
Russo et al. (2016). "Extending the golden hour: Partial resuscitative endovascular balloon occlusion of the aorta in a highly lethal swine liver injury model." J Trauma Acute Care Surg. 80(3): 372-380. doi:10.1097/TA.0000000000000940.
Russo et al. (2016). "Partial Resuscitative Endovascular Balloon Occlusion of the Aorta in Swine Model of Hemorrhagic Shock." J Am Coll Surg. 223(2): 359-368. doi:10.1016/j.jamcollsurg.2016.04.037.
Russo et al. (2017). "Two lives, one REBOA: Hemorrhage control for urgent cesarean hysterectomy in a Jehovah's Witness with placenta percreta." Journal of Trauma and Acute Care Surgery. Sep. 1, 2017;83(3):551-3.
Simon et al. (2017). "A Case of Resuscitative Endovascular Balloon Occlusion of the Aorta (REBOA) Use in Penetrating Abdominal Aortic Injury." Journal of Endovascular Resuscitation and Trauma Management. 1(1): 53-7.
Simon et al. (2018). "Lower extremity cooling reduces ischemia-reperfusion injury following Zone 3 REBOA in a porcine hemorrhage model." J Trauma Acute Care Surg vol. 85, No. 3: 512-528. DOI: 10.1097/TA.0000000000001990.
Tibbits et al. (2018). "Location Is Everything: The Hemodynamic Effects of REBOA in Zone 1 versus Zone 3 of the Aorta." J Trauma Acute Care Surg. 85(1):101-7. doi:10.1097/TA.0000000000001858.
White et al. (2020). "A New Pressure-Regulated, Partial REBOA Device Achieves Targeted Distal Perfusion." Journal of Surgical Research. 256: 171-179.
Williams et al. (2016). "Extending REBOA: Endovascular Variable Aortic Control (EVAC) in a Lethal Model of Hemorrhagic Shock." Journal of Trauma and Acute Care Surgery, vol. 81, No. 2, pp. 294-301.
Williams et al. (2017). "Automated variable aortic control versus complete aortic occlusion in a swine model of hemorrhage." J Trauma Acute Care Surg. 82(4): 694-703. doi:10.1097/TA.0000000000001372.
Williams et al. (2017). "What's in a name ?: A consensus proposal for a common nomenclature in the endovascular resuscitative management and REBOA literature." J Endovasc Resusc Trauma Manag. 1(1):9-12. doi:10.26676/jevtm.v1i1.7.
Williams et al. (2018). "EVAC versus REBOA in a Swine Model of Hemorrhage and Ischemia Reperfusion Injury." J Trauma Acute Care Surg. 85(3):519-26. doi:10.1097/TA.0000000000002008.
Williams et al. (2018). "A Novel Automated Endovascular Variable Aortic Control Device to Expand Function of Standard REBOA Catheters." Journal of Endovascular Resuscitation and Trauma Management. 2(3): 1-8. DOI: 10.26676/jevtm.v2i3.65.
U.S. Appl. No. 17/194,053, filed Mar. 5, 2021 by Johnson et al. (copy not attached).
Divani et al., "Blood Pressure Variability Predicts Poor In-Hospital Outcome in Spontaneous Intracerebral Hemorrhage" Stroke (2019) 50(8):2023-2029.
Extended European Search Report mailed on Mar. 25, 2024 for European Application No. EP23207427.8, 13 pages.
International Search Report and Written Opinion for International Application No. PCT/US2023/011298 dated Mar. 15, 2024, 23 pages.
Invitation to pay additional fees for International Application No. PCT/US2023/011298, dated Jan. 23, 2024, 17 pages.
Non-Final Office Action for U.S. Appl. No. 18/078,857 dated Mar. 6, 2024, 9 pages.
Tsoukalas et al., "A solid-state pressure-sensing microsystem for biomedical applications" Sensors and Actuators A: Physical (1997) 62(1-3):551-555.
International Search Report and Written Opinion for Application No. PCT/US2022/033896, mailed on Nov. 28, 2022, 25 pages.
International Search Report and Written Opinion for International Application No. PCT/US2022/033898 dated Dec. 16, 2022, 30 pages.
International Search Report and Written Opinion for International Application No. PCT/US2022/049335 dated Mar. 15, 2023, 15 pages.
Chengod et al., "Selective left bronchial intubation and left-lung isolation in infants and toddlers: analysis of a new technique" J Cardiothorac Vasc Anesth. Oct. 2005;19(5):636-641.
Deaton, "Image-Guided Thrombectomy in Vascular Surgery" Endovascular Today Jul. 2005, 32-35.
Final Office Action for U.S. Appl. No. 17/194,053 mailed Oct. 10, 2024, 27 pages.
Final Office Action for U.S. Appl. No. 18/078,857 mailed Aug. 19, 2024, 7 pages.
Gerstenfeld et al., "Pulmonary vein isolation using a compliant endoscopic laser balloon ablation system in a swine model" J. Interv Card Electrophysiol (2010) 29:1-9.
Gu et al., "A new technique for sizing of atrial septal defects" Catheter Cardiovasc Interv. Jan. 1999; 46(1):51-57.
International Search Report and Written Opinion for PCT Application No. PCT/US2023/072764 mailed Dec. 20, 2024, 22 pages.
Mathis et al., "Physical Characteristics of Balloon Catheter Systems Used in Temporary Cerebral Artery Occlusion" AJNR Am J Neuroradiol (1994) 15:1831-1836.
Mccarthy et al., "Automated Balloon Control in Resuscitative Endovascular Balloon Occlusion of the Aorta", IEEE Transactions on Biomedical Engineering, IEEE, USA (2019) 66(6):1723-1729.
Non-Final Office Action for U.S. Appl. No. 17/842,755 mailed Jan. 16, 2025, 32 pages.
Non-Final Office Action for U.S. Appl. No. 18/160,248 mailed on Oct. 9, 2024, 13 pages.
Non-Final Office Action for U.S. Appl. No. 18/193,369 mailed Jul. 2, 2024, 8 pages.
Notice of Allowance for U.S. Appl. No. 18/078,857, mailed on Jan. 7, 2025, 8 pages.
Notice of Allowance for U.S. Appl. No. 18/160,248 mailed on Feb. 6, 2025, 9 pages.

(56) References Cited

OTHER PUBLICATIONS

Notice of Allowance for U.S. Appl. No. 18/193,369 mailed Jan. 8, 2025, 7 pages.

Notice of Allowance mailed on Sep. 11, 2024, for U.S. Appl. No. 18/078,857, filed Dec. 9, 2022, 9 pages.

Okell et al., "A theoretical framework for quantifying blood volume flow rate from dynamic angiographic data and application to vessel-encoded arterial spin labeling MRI" Medical Image Analysis, vol. 17, Issue 8, pp. 1025-1036, Dec. 2013.

Owens et al., "Handbook of Endovascular Peripheral Interventions" Springer (2012), 462 pages.

Saab, "Applications of High-Pressure Balloons in the Medical Device Industry" Medical Device & Diagnostic Industry Magazine Sep. 2000, 18 pages.

Scott et al., "A novel fluoroscopy-free, resuscitative endovascular aortic balloon occlusion system in a model of hemorrhagic shock" J Trauma Acute Care Surg. Jul. 2013; 75(1):122-128.

\* cited by examiner

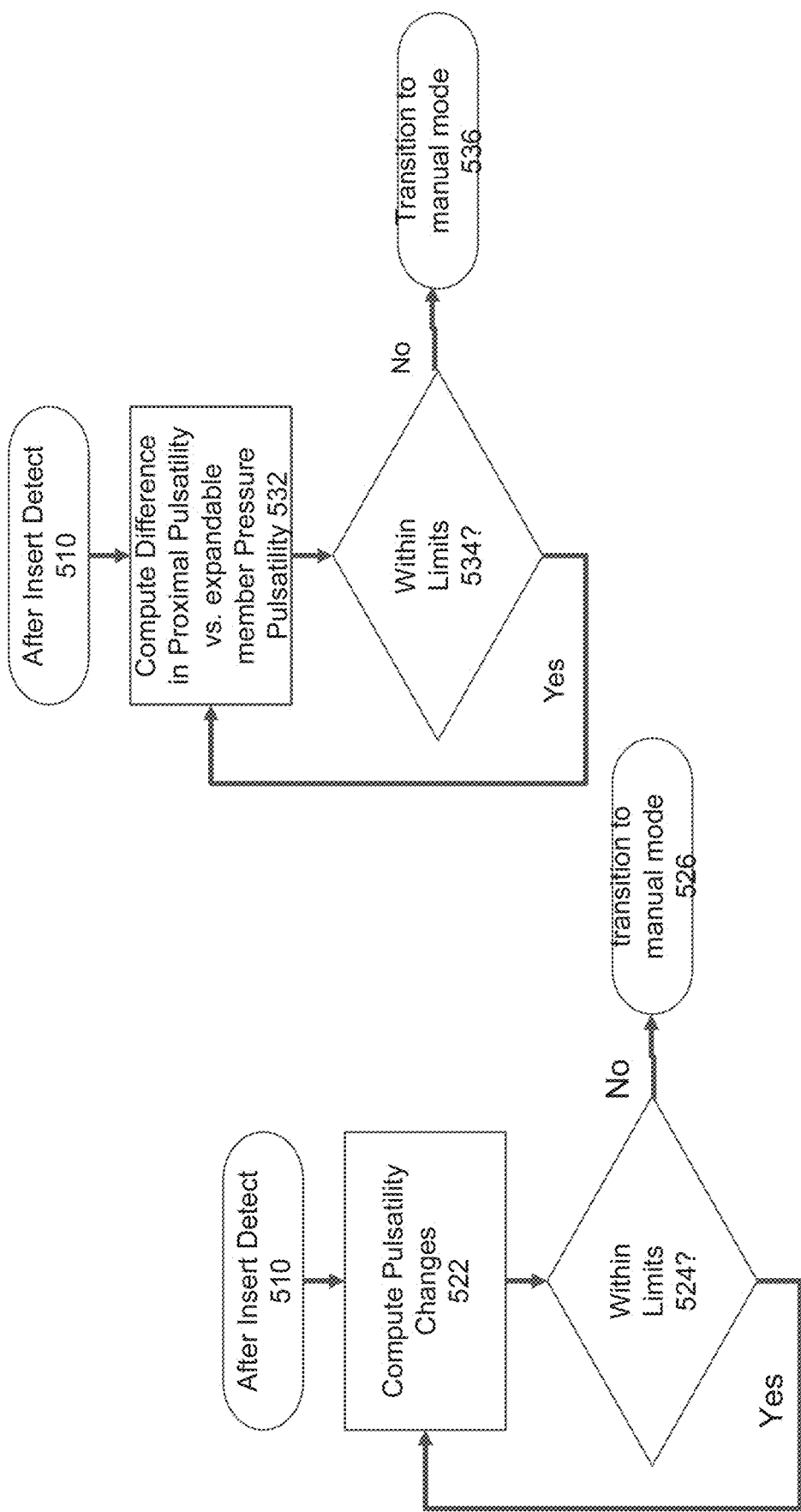

BLOOD FLOW CONTROL DEVICES, SYSTEMS, AND METHODS AND ERROR DETECTION THEREOF

CROSS-REFERENCE TO RELATED APPLICATIONS

This application claims priority to U.S. Patent Application Ser. No. 62/990,302 filed Mar. 16, 2020, which is hereby incorporated in its entirety by this reference.

GOVERNMENT SUPPORT

This invention was made with government support under grant FA8650-20-2-6116 awarded by the United States Air Force/Air Force Material Command. The government has certain rights in the invention.

TECHNICAL FIELD

This invention relates generally to the field of error condition detection and response in medical devices.

BACKGROUND

Typically, medical devices may undergo some tests prior to use. These tests are usually to demonstrate that medical devices can perform reliably and safely during use. However, despite such tests some medical devices may still be prone to errors. For example, tests may be conducted after manufacturing medical devices but before shipping the medical devices to a point of use. In such scenarios, these medical devices may be prone to damage during shipment or during set up at the point of use. Similarly, at the point of use, continuous use of medical devices may subject components of the medical devices to wear and tear that may result in failure.

Damage and/or degradation, such as, for example, excessive force or vibrations, exposure to temperatures outside predefined ranges, excess UV exposure, moisture intrusion, and/or excess electrostatic discharge, (collectively referred to herein as "damage") to one or more components of a medical device can lead to errors when the medical device is in use. Such errors can significantly impact the health of a patient and may even be life threatening. More specifically, balloon catheters are therapeutic devices to treat shock in patients. Balloon catheters are placed inside a part (e.g., a blood vessel) of a patient's body to control the flow of blood to vital organs. Errors during a therapeutic treatment due to damage to balloon catheters can be life threatening to a patient.

Conventionally, blood flow control systems such as balloon catheters are controlled manually during a procedure. An operator may manually inflate and/or deflate a balloon on the balloon catheter, using, for example, a syringe, to perform the procedure. During the procedure, the operator may monitor, visually and/or with the assistance of other medical devices, the physiologic conditions of the patient in order to determine the amount of inflation and/or deflation. The amount of inflation and/or deflation in turn may control the blood flow in the patient. However, relying solely on manual control (e.g., manual inflation and/or deflation) may make the procedure susceptible to human errors.

While, automated balloon catheters that assist in controlling blood flow when placed in a patient's aorta have recently been developed (e.g., see Johnson et al WO 2018/132623), additional devices, systems, and methods to effectively identify and respond to errors and alarms while using such catheters would be desirable. For example, additional devices, systems, and methods capable of detecting damage to one or more components of the system, e.g., due to transit or otherwise, and/or capable of detecting errors due to other circumstances, e.g., interference from another device, clotting in a blood vessel, etc., or prediction that increased flow would result in excessive bleeding are desirable to avoid automated inflation and/or deflation based on incorrect or inaccurate measurements. As can clearly be appreciated, the consequences of automatically controlling blood flow in a patient without responding to errors due to damage or physiologic changes may be life threatening to the patient.

Accordingly, there is an unmet need for sophisticated devices, systems and methods for identifying and responding to errors and physiologic alarms in medical devices (e.g., automated balloon catheters, semi-automated balloon catheters, etc.).

SUMMARY

Blood flow control devices, systems, and methods are described herein. In some variations, a blood flow control system may comprise a blood flow control device for placement within a body of a patient. The blood flow control device may comprise an expandable member and a sensor configured to measure at least one of a physiologic condition of the patient and a pressure associated with the expandable member. The blood flow control system may also comprise one or more controllers communicably coupled to the sensor and configured to: receive data indicative of at least one of the physiologic condition of the patient and the pressure associated with the expandable member from the sensor, compare the received data with target data, identify at least one error based on the comparison, and inhibit at least one function of the blood flow control system in response to identifying the error.

In some variations, the system may further comprise a pump to control a volume of the expandable member. In some variations, the at least one function may comprise automatic control of the expandable member. In some variations, the one or more controllers may be configured to inhibit automatic control of the expandable member by transitioning the blood flow control system from an automatic mode of operation to a manual mode of operation.

In some variations, the at least one error may indicate an error in the placement of the blood flow control device. The received data may be proximal mean arterial pressure from the proximal sensor and distal mean arterial pressure from the distal sensor. The one or more controllers may be further configured to compare at least one of the proximal mean arterial pressure and the distal mean arterial pressure to a target value.

In some variations, the at least one error may indicate clotting that may interfere with a function of the sensor. The received data may be proximal systolic pressure, proximal diastolic pressure, and expandable member pressure. The one or more controllers may be configured to compare a proximal average pulsatility to an expandable member pressure pulsatility. In some variations, the one or more controllers may be configured to compare a distal average pulsatility to an expandable member pulsatility.

In some variations, the at least one error may indicate electrical interference from another device. The received data may be proximal blood pressure and distal blood pressure. The one or more controllers may be configured to compare the proximal blood pressure to a first threshold value and the distal blood pressure to a second threshold value. In some variations, the received data may be heartbeat. The one or more controllers may be configured to compare the heartbeat to a target heartbeat range. In some variations, the one or more controllers may be configured to transition the blood flow control system to the manual mode in response to the electrical interference exceeding a threshold time. In some variations, the one or more controllers may be configured to transition the blood flow control system to the automatic mode in response to the electrical interference not exceeding a threshold time.

In some variations, the at least one error may indicate an error in pressure gradient between the first sensor and the second sensor. The sensor may include a proximal sensor and a distal sensor. The received data may be proximal mean arterial pressure from the proximal sensor and distal mean arterial pressure from the distal sensor. The one or more controllers may be configured to compare distal pulsatility to a target distal pulsatility.

In some variations, the sensor may include a proximal sensor and a distal sensor. The error may indicate an error in functionality with at least one of the proximal sensor and the distal sensor. In some variations, the received data may be proximal mean arterial pressure from the proximal sensor and distal mean arterial pressure from the distal sensor. The one or more controllers may be configured to compare the proximal mean arterial pressure to the distal mean arterial pressure.

In some variations, the one or more controllers may inhibit at least one function by shutting down the blood flow control system. In some variations, the error may indicate damage to the sensor. The received data may be proximal pressure, distal pressure, and expandable member pressure. The one or more controllers may be configured to compare at least one of the proximal pressure, the distal pressure, and the expandable member pressure to at least one target value.

In some variations, the error may indicate damage to the expandable member. The received data may be expandable member pressure. The one or more controllers may be configured to compare the expandable member pressure to a target value.

In some variations, the error may indicate that the expandable member may have reached a maximum value. The received data may be expandable member pressure. The one or more controllers may be configured to compare the expandable member pressure to a maximum threshold value.

In some variations, the system may further comprise a user interface communicably coupled to the one or more controllers. The one or more controllers may be further configured to transmit an alert to a user via the user interface. In some variations, the target data may comprise a user-inputted target value. The alert may indicate an error in the target value. The received data may be proximal systolic blood pressure. The one or more controllers may be configured to compare the proximal systolic blood pressure to the target value.

In some variations, the received data may be a number of automatic inflation of the expandable member. The one or more controllers may be configured to compare the number of automatic inflations to reach the target value to a threshold count. The target value may indicate a target blood pressure measurement. In some variations, the received data may be a number of automatic deflation of the expandable member. The one or more controllers may be configured to compare the number of automatic deflations to reach the target value to a threshold count. The target value may indicate a target blood pressure measurement.

In some variations, the alert may indicate an unsafe occlusion time. The unsafe occlusion time may be total time at occlusion. In some variations, the unsafe occlusion time may be a duration of most recent uninterrupted time at occlusion. In some variations, the received data may be distal systolic pressure and occlusion time. The one or more controllers may be configured to compare the occlusion time to a first threshold value and the distal systolic pressure to a second threshold value.

In some variations a blood flow control system may comprise a blood flow control device for placement within a body of a patient. The blood flow control device may comprise an expandable member and a sensor configured to measure at least one of a physiologic condition of the patient and a pressure associated with the expandable member. The blood flow control system may also comprise one or more controllers communicably coupled to the sensor and configured to: receive data indicative of at least one of the physiologic condition of the patient and the pressure associated with the expandable member from the sensor, compare the received data with target data, identify at least one error based on the comparison, and inhibit at least one function of the blood flow control system in response to identifying the error. In some variations, the alert may indicate an unsafe occlusion time. The target data may comprise a user-inputted target value. The alert may indicate an error in the target value.

In some variations, a method for controlling blood flow in a patient may comprise advancing a distal portion of a blood flow control device through a blood vessel of a patient. The distal portion may comprise an expandable member and a sensor. The method may also include receiving data indicative of at least one of a physiologic condition of the patient in the blood vessel and a pressure of the expandable member from the sensor. The method may also include comparing the received data with target data, identifying at least one error based on the comparison, and inhibiting at least one function of the blood flow control device in response to identifying the error.

In some variations, advancing the distal portion of the blood flow control device may include advancing the expandable member to an artery of the patient. In some variations, inhibiting the at least one function may include inhibiting an automatic control of the expandable member. In some variations, inhibiting the automatic control of the expandable member may comprise automatically transitioning the blood flow control device from an automatic mode of operation to a manual mode of operation.

In some variations, comparing the received data with target data may comprise comparing at least one of a proximal mean arterial pressure and a distal mean arterial pressure to a target value. The error may be indicative of an error in advancing the distal portion of the blood flow control device through the blood vessel.

In some variations, comparing the received data with target data may comprise comparing a proximal average pulsatility to an expandable member pressure pulsatility. The error may be indicative of a clotting in the blood vessel. In some variations, comparing the received data with target data may comprise comparing a distal average pulsatility to an expandable member pressure pulsatility. The error may indicative of a clotting in the blood vessel.

In some variations, comparing the received data with target data may comprise comparing a proximal blood pressure to a first threshold value and a distal blood pressure to a second threshold value. The error may be indicative of electrical interference from another device. In some variations, the method may include transitioning the blood flow control device to the manual mode in response to the electrical interference exceeding a threshold time. In some variations, the method may include transitioning the blood flow control device to the automatic mode in response to the electrical interference not exceeding the threshold time.

In some variations, inhibiting the automatic control of the expandable member may shutting down the blood flow control system. In some variations, comparing the received data with target data may comprise comparing at least one of a proximal pressure, a distal pressure, and an expandable member pressure to at least one target value. The error may be indicative of damage to the sensor.

In some variations, comparing the received data with target data may comprise comparing an expandable member pressure to a target value. The error may be indicative of damage to the expandable member. In some variations, comparing the received data with target data may comprise comparing an expandable member pressure to a maximum threshold value. The error may be indicative of the expandable member having reached a maximum volume.

In some variations, the method may further comprise transmitting an alert indicating the error to a user interface. In some variations, comparing the received data with target data may comprise comparing a proximal systolic blood pressure to a target value. Transmitting the alert may comprise transmitting an instruction to change the target value.

In some variations, comparing the received data with target data may comprise comparing an occlusion time to a first threshold value and a distal systolic pressure to a second threshold value. Transmitting the alert may comprise indicating an unsafe occlusion time.

In some variations, a blood flow control system may comprise a blood flow control device configured to be placed within a portion of a body of a patient. The blood flow control device may comprise an expandable member and at least one sensor. A pump may be operably coupled to the expandable member. One or more controllers may be communicably coupled to the blood flow control device and the pump. The one or more controllers may be configured to: automatically control inflation of the expandable member using the pump in an automatic mode based on data from the at least one sensor, identify an error in the blood flow control system, and upon identification of the error, automatically transition the blood flow control system from the automatic mode to a manual mode so as to inhibit automatic control of the expandable member with the one or more controllers.

In some variations, a method for assisting in blood flow control may include placing an expandable member of a blood flow control system in a blood vessel of a body. The blood flow control system may comprise a first blood pressure sensor positioned proximal of the expandable member and a second blood pressure sensor positioned distal of the expandable member. The method may also include receiving first and second blood pressure measurements from the first and second sensors respectively after placing the expandable member in the blood vessel. The method may also include comparing the first blood pressure measurement to a first range of target blood pressures and the second blood pressure measurement to a second range of target blood pressures. The first and second ranges may correspond to expected blood pressure values in the blood vessel. The method may also include automatically transitioning the blood flow control system from an automatic mode of operation to a manual mode of operation in response to determining that at least one of the blood pressure measurements falls outside the corresponding range.

In some variations, a system for assisting in blood flow control may comprise a blood flow control device comprising an expandable member having a volume. A first sensor may be positioned proximal of the expandable member. A second sensor may be positioned distal of the expandable member. The first sensor may be configured to measure a first blood pressure of the patient and the second sensor is configured to measure a second blood pressure of the patient. In some variations, a pump may be operably coupled to the expandable member and configured to change the volume of the expandable member. One or more controllers may be communicably coupled to the first sensor, the second sensor, and the pump. The one or more controllers may be configured to: change a volume of the expandable member, receive first and second blood pressure measurements from the first and second sensors respectively in response to the change to the volume of the expandable member, and compare the first blood pressure measurement to a first range of target blood pressures and the second blood pressure measurement to a second range of target blood pressures. The first and second target ranges may correspond to expected blood pressure values based on the change to the volume of the expandable member. The one or more controllers may be configured to automatically transition the blood flow control system from an automatic mode of operation to a manual mode of operation in response to determining that at least one of the blood pressure measurements falls outside the corresponding range.

In some variations, a system for assisting in blood flow control may comprise a blood flow control device comprising an expandable member having a volume. A first blood pressure sensor may be positioned proximal of the expandable member and a second blood pressure sensor may be positioned distal of the expandable member. The one or more controllers may be communicably coupled to the first sensor and the second sensor. The one or more controllers may be configured to: receive first and second blood pressure measurements respectively from the first and the second blood pressure sensors in response to a placement of the expandable member within a portion of the patient's body. The one or more controllers may be configured to compare the first blood pressure measurement to a first range of target blood pressures and the second blood pressure measurement to a second range of target blood pressures. The first and second ranges may correspond to expected blood pressure values in the portion of the patient's body. The one or more controllers may be configured to automatically transition the blood flow control system from an automatic mode of operation to a manual mode of operation in response to determining that at least one of the blood pressure measurements falls outside the corresponding range.

BRIEF DESCRIPTION OF THE DRAWINGS

FIGS. 5A-5I are flow diagrams of an exemplary variations of a runtime check test.

DETAILED DESCRIPTION

Figure 1:
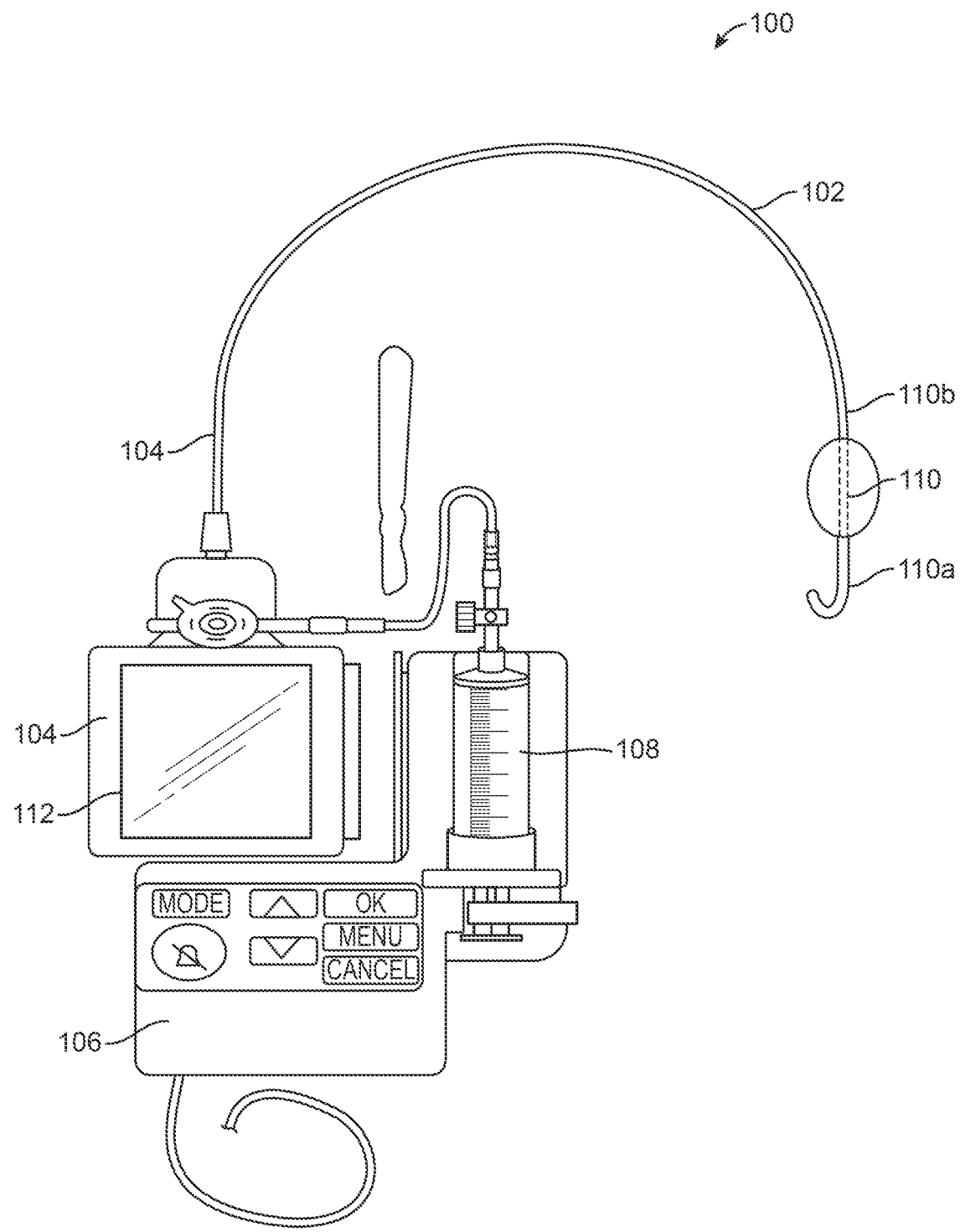
FIG. 1 illustrates an exemplary variation of a blood flow control system.

Non-limiting examples of various aspects and variations of the invention are described herein and illustrated in the accompanying drawings.

Balloon catheters are therapeutic devices to treat shock in patients. Balloon catheters may be strategically placed within a blood vessel (e.g. aorta) of a patient in shock. An expandable member included in the balloon catheter may be inflated and/or deflated to partially or fully occlude the blood vessel. The amount of occlusion may regulate the blood flow to vital organs in the patient's body. This in turn may help maintain adequate oxygen delivery to the vital organs.

Conventionally, the inflation and/or deflation of the expandable member may be performed manually. For example, a fluid (e.g., saline, etc.) and/or a compressed gas (e.g., carbon dioxide, etc.) may be introduced into the expandable member such that the expandable member attains a specific volume that corresponds to an amount of occlusion in the blood vessel. An operator may use a syringe to inject or remove the fluid and/or the compressed gas from the expandable member in order to inflate or deflate the expandable member. The amount of fluid to be injected or removed may be determined by continuously monitoring the physiologic conditions of the patient. For example, one or more sensors may determine the blood pressure upstream from occlusion, downstream from occlusion, and/or at the site of the occlusion. The operator may monitor the sensor data and may adjust the amount of fluid and/or compressed gas injected or removed from the expandable member accordingly. By adjusting the amount of fluid and/or compressed gas in the expandable member, the operator adjusts the volume of the expandable member, thereby adjusting the amount of occlusion in the blood vessel. However, such continuous manual control of the expandable member may be prone to human errors.

To combat this, more recently, automated balloon catheters have been introduced to automate the inflation and/or deflation of the expandable member. In automated balloon catheters, one or more controllers may continuously monitor the physiologic conditions of the patient by monitoring sensor data from the sensor(s). The syringe may be coupled to an actuation mechanism that may automatically inject or remove fluid and/or compressed gas from the expandable member based on the sensor data. For instance, the actuation mechanism may be coupled to the controller(s) to adjust the amount of fluid and/or compressed gas based on the data from the sensor(s). This in turn may control the volume of the expandable member.

However, damage to one or more components of the automated balloon catheter may lead to errors in sensor data. Put differently, the actual physiologic condition (e.g., blood pressure, heart rate, respiratory rate, intracranial pressure, cerebral oxygenation, cerebral blood flow, or electro-encephalographically) of the patient may not correspond to the data from the sensor(s) due to damages to the components. Additionally, if the operator errs during the procedure (e.g., places the automated balloon catheter in a different blood vessel than intended, at a different position, etc.), the data from the sensor(s) may correspond to physiologic conditions that may be different from expected physiologic conditions. Without error detection, the controller(s) in the automated balloon catheter may continue to adjust the volume of the expandable member based on the erroneous physiologic values due to inaccurate sensor(s) data and/or operator errs. This may cause the controller(s) to inject or remove an undesirable amount of compressible fluid, thereby inflating or deflating the expandable member by an undesirable volume.

While the errors may be due to physical problems with the device, a second set of state detection alarms may be critical when controlling blood flow and blood pressure within a patient using balloon catheters. These physiologic alarms may notify a user when a specific physiologic state has been predicted or been reached. Identifying these physiologic states may be accomplished by analysis of current physiology, such as blood pressure, but can also be predicted by identifying changes in physiology in response to changes in the balloon catheter. Identifying physiologic states through the identification of physiologic changes in response to balloon changes is possible when balloon changes are automated and accurately recorded.

Accordingly, it may be advantageous to notify a user (e.g., a surgeon, an operator, etc.) of the physiologic state of the patient during the use of automated balloon catheters (e.g., aortic occlusion device). For instance, physiologic states may be assessed and monitored to identify the status of a patient. In some variations, an expected physiologic change may be predicted for a change in a volume of the expandable member. The actual physiologic state of the patient may be compared to the expected physiologic state. If there is a mismatch, an alert may be transmitted to the user to alter and/or stop the treatment of the patient.

A method for controlling blood flow and an automated blood flow control system that detects errors and physiologic states and responds to the errors and physiologic states by automatically adjusting control of the expandable member is described herein. In some variations, the blood flow control system may include a blood flow control device, such as, for example, an elongate body comprising an expandable member. The devices, systems, and methods described herein may identify errors due to any number of different circumstances, including but not limited to, physical damage of one of more components of the blood flow control system, interference due to excess electrical noise, physical interference with one or more sensors (e.g., clotting blocking the sensor), operator errs, etc. The physiologic state predictions may include but are not limited to predicted ongoing bleeding, predicted hemodynamic collapse, predicted changes in the aortic size, etc. For instance, the devices, systems and methods described herein may identify errors or physiologic states in the data from the sensor(s), and based on this data, may inhibit at least one function of the blood flow control system.

As mentioned above, the blood flow control systems described herein may comprise a blood flow control device for placement within a part of a body (e.g., within a blood vessel such as, for example, the aorta) of a patient. The blood flow control device may include an elongate body, an expandable member and a sensor. The sensor may be configured to measure a physiologic condition of the patient and/or a pressure associated with the expandable member. The blood flow control system may further comprise one or more controllers that may be communicably coupled to the sensor. The controller(s) may be configured to receive data from the sensor that may be indicative of the physiologic condition of the patient and/or the pressure associated with the expandable member. The controller(s) may compare the received data with target data and may identify at least one error or physiologic state based on the comparison. In response to identifying the error or state, the controller(s) may inhibit at least one function of the blood flow control system.

For instance, the controller(s) may inhibit and/or prevent further automated adjustment or control of the size (e.g., volume) of the expandable member when certain conditions exist. Put differently, the controller(s) may automatically transition the blood flow control system from an automatic mode, wherein the size of the expandable member is automatically controlled by the controller(s), to a manual mode, wherein the size of the expandable member is manually controlled by a user using the blood flow control system (e.g., a user interface of the blood flow control system). Additionally, or alternately, the controller(s) may inhibit the function of the blood flow control system by preventing use (e.g., turning off or otherwise preventing use) of all or a portion of the blood flow control system (e.g., preventing use of the user interface, preventing use of the controller entirely, preventing use of the entire system). In some instances, the controller(s) may transmit alerts to a user (e.g., an operator, a surgeon, etc.) indicating an error or change in physiologic state. In this manner, the size of the expandable member may be adjusted in an accurate manner by the controller(s) despite damage to components within the blood flow control system, errors in therapeutic procedures, or changes in the patient's physiology.

Blood Flow Control System

FIG. 1 illustrates an exemplary variation of a blood flow control system 100. The blood flow control system 100 may comprise a blood flow control device 104, an elongate body 102, an expandable member 110, one or more controllers, such as, device controller 112 and system controller 106, one or more sensors, a pump 108, and a user interface. The blood flow control device 104 may comprise an elongate body 102, such as, for example, a catheter, and an expandable member 110, such as, for example, a balloon. The expandable member 110 may be disposed on, coupled to, integrated with, attached to, or otherwise affixed to the elongate body 102. The blood flow control device 104 may also comprise one or more sensors (not shown in FIG. 1) and optionally a device controller 112. In variations in which the blood flow control device 104 comprises one or more sensors, the sensors may be disposed on, coupled to, integrated with, attached to, or otherwise affixed to the elongate body 102. In other variations, one or more of the sensors may be external to or separate from the blood flow control device 104. The sensor(s) may be operably coupled to one or both of the device controller 112 and the system controller 106. In some variations, the sensor(s) and thereby the blood flow control device 104 may be communicably coupled to the system controller 106 (e.g., via the device controller 112). The expandable member 110 and therefore the blood flow control device 104 may be operably coupled to the pump 108. The pump 108 may include or may otherwise be coupled to an actuation mechanism (not shown in FIG. 1) that may be controlled by the system controller 106. While described above as two controllers, a device controller 112 and a system controller 106, it should be appreciated that a single controller could be utilized to perform the functions of both the device controller 112 and the system controller 106 described herein, and/or any of the functions of the device controller 112 could be performed by the system controller 106 and vice versa. Accordingly, any of the components described herein as coupled to either the device controller 112 or the system controller 106 may be coupled to the other of the device controller 112 or the system controller 106 or to both controllers, as the case may be.

Blood Flow Control Device 104

As described above and depicted in FIG. 1, the blood flow control device 104 may comprise an elongate body 102, an expandable member 110 coupled to the elongate body 102, and one or more sensors coupled to or integrated with a shaft of the elongate body 102.

Elongate Body 102

The elongate body 102 may comprise a shaft sized and shaped for placement within a blood vessel (e.g., aorta, vein, etc.) of a patient. In some variations, the elongate body 102 may have a length sufficient to reach a patient's aorta via the femoral or radial artery. For example, in some variations, the elongate body 102 may be a catheter configured to be inserted into the femoral or radial artery and to extend through the patient's vasculature into the aorta. In some variations, the elongate body 102 may be steerable. For example, in some variations, the elongate body 102 be mechanically coupled to knobs, levers, pullwires, and/or the like that may be used to steer or otherwise deflect a distal end of the shaft of the elongate body 102. In some variations, the elongate body 102 may include one or more lumens (not shown in FIG. 1) therethrough. The lumen(s) may be partial lumen(s) (e.g., open on one end) and may be disposed within or lie within the movable shaft. Alternatively, the movable shaft may define one or more lumen(s). In some variations, the lumen(s) may include an intake or inflation lumen and an exhaust or deflation lumen to deliver fluid and/or compressed gas to the expandable member and to recover the fluid and/or compressed gas from the expandable member 110, respectively.

Expandable Member 110

The expandable member 110 may be one of disposed on, coupled to, integrated with, attached to, and/or affixed to the shaft of the elongate body 102 and a size of the expandable member may be controllable by a controller or a user. For example, the expandable member may be configured to expand and contract and/or inflate and deflate such that the size (e.g., volume) of the expandable member may change during use of the blood flow control system. In some variations, the expandable member may be an inflatable/deflatable balloon, while in other variations the expandable member may comprise a shape memory material, in yet other variations, the expandable member may be connected to mechanical linkage (e.g., wires, etc.) to change the size of the expandable member. The expandable member 110 may comprise any suitable elastomeric material (e.g., polyurethane, silicone, etc.). Alternatively, the expandable member 110 may comprise polyester, nylon, etc. During use, blood flow may be regulated or otherwise controlled by changing a size of the expandable member 110, thereby altering the area of the blood vessel that is occluded by the expandable member 110. Fluid and/or compressed gas may be delivered through one or more lumens in the elongate body 102 in order to control and/or adjust the size (e.g., volume) of the expandable member 110. Thus, in some variations, the expandable member 110 may be strategically placed within the aorta of a patient and the size of the expandable member 110 may control blood flow through the aorta of the patient such that blood flow distal to expandable member 110 may be impeded to augment blood pressure proximal to expandable member 110. The outer surface of the expandable member 110 may be configured to contact or otherwise interface with the wall(s) of the patient's blood vessel (e.g., at complete occlusion).

Although FIG. 1 illustrates one expandable member 110 configured to regulate blood flow through the aorta of the patient, it should be readily understood that the blood flow control device 104 may include any number of suitable expandable members 110. For instance, the blood flow control device 104 may include two expandable members 110 disposed on, coupled to, integrated with, attached to, and/or affixed to the elongate body 102 in series. Similarly, the blood flow control device may include three expandable members disposed on, coupled to, integrated with, attached to, and/or affixed to the elongate body 102 in series spaced at equal distance from each other. In some variations, the expandable member 110 may comprise a plurality of balloons (e.g., two, three, four, or more) positioned in series along the length of the elongate body 102 or disposed within each other. In variations comprising a plurality of balloons, the balloons may be configured to expand and contract individually or separately.

Sensor(s)

The blood flow control system may comprise one or more sensors (e.g., two, three, four, five, or more). In some variations, the blood flow control device may itself comprise one or more sensors, while in other variations, one or more sensors may be integrated into the system separately from the blood flow control device. In some variations, the blood flow control device may comprise one or more sensors, and one or more sensors may be integrated into the system separately from the blood flow control device. For example, one or more sensors (e.g., a distal sensor, a proximal sensor) may be integrated with and/or disposed on the elongate body 102 of the blood flow control device.

Additionally or alternatively, one or more sensors may be disposed on tubing that may be coupled to open ports in elongate body 102. For example, one or more sensors (e.g., a proximal sensor, a distal sensor) may be connected via a saline-filled tube that may connect to open ports that are proximal or distal to the expandable member 110. Put differently, instead of being disposed on the elongate body 102, these sensors may be coupled to saline-filled tubes that are fluidly coupled to the elongate body 102 (e.g., at ports proximal or distal to the expandable member) via the saline-filled tube. In such variations, the pressure along the saline-filled tube may be measured by the proximal sensor and the distal sensor.

In yet other alternative variations, the one or more sensors may be integrated into and/or disposed on the blood flow control system 100 via a combination of the saline-filled tube and via one or more wires.

In variations in which the blood flow control device comprises one or more sensors, the blood flow control device may comprise any suitable number of sensors (e.g., two, three, four, five, or more) and the sensors may be positioned in any suitable location for measuring a physiologic condition of the patient and/or a characteristic of the expandable member. For example, the blood flow control device may comprise a first, distal sensor, and a second, proximal sensor. The distal sensor, the position of which is indicated by reference numeral 110b, may be disposed between a tip of the elongate body 102 and the expandable member 110. A proximal sensor, the position of which is indicated by reference numeral 110a, may be disposed between the base of the elongate body 102 (where the elongate body 102 couples to device controller 112) and the expandable member 110. Each of the distal sensor and the proximal sensor may measure patient physiologic information, such as physiologic information indicative of blood flow through the aorta, to determine the patient's underlying physiology. For example, the distal sensor and the proximal sensor may measure a local blood pressure of the patient at or around the position of the respective sensor. For example, the distal sensor may measure a blood pressure of the patient within the blood vessel at a region surrounding 110b and the proximal sensor may measure a blood pressure of the patient within the blood vessel at a region surrounding 110a. The data from the distal sensor may be used to measure the distal systolic pressure and the distal diastolic pressure of the patient. For instance, distal systolic pressure and distal diastolic pressure may be inferred from a waveform of the blood pressure. Distal systolic pressure may be measured by analyzing peaks of the waveform for a given time duration. Distal diastolic pressure may be measured by analyzing valleys of the waveform for the given time duration. Distal mean arterial pressure may be measured from the distal systolic pressure and the distal diastolic pressure. In a similar manner, the data from the proximal sensor may be used to measure the proximal systolic pressure and the proximal diastolic pressure of the patient. For instance, proximal systolic pressure and proximal diastolic pressure may be inferred from a waveform of the blood pressure. Proximal systolic pressure may be measured by analyzing peaks of the waveform for a given time duration. Proximal diastolic pressure may be measured by analyzing valleys of the waveform for the given time duration. Proximal mean arterial pressure may be measured from the proximal systolic pressure and the proximal diastolic pressure.

Although the proximal sensor and the distal sensor may measure a blood pressure of the patient, in some variations, the blood pressure may be used to calculate one or more of heart rate, respiratory rate, blood flow rate, cardiac output of the patient, and/or the like.

Note that the terms "proximal" and "distal," as used herein in relation to sensor(s) and/or particular localized blood pressure readings, refer to blood flow directionality from the heart. That is, "proximal" is closer to the heart while "distal" is further from the heart. This is not to be confused with the reversed usage of the terms when described from the perspective of a medical device such as a catheter, where the "distal end" of the medical device would commonly be understood as the end with the expandable element 110 furthest from the system controller 106 and the "proximal end" would be understood as the end closer to the operator.

In some variations, the blood flow control device may further comprise an expandable member sensor (not shown in FIG. 1). In some variations, the expandable member sensor may be coupled to, integrated with and/or disposed on the expandable member 110 or on the elongate body 102 within the expandable member 110. In some variations, the expandable member sensor may be coupled to, integrated with and/or disposed on the device controller 112 and may be fluidly coupled to the expandable member.

The expandable member sensor may detect a characteristic of the expandable member, such as, for example, a pressure of fluid and/or compressed gas inside the expandable member 110. In some variations, the pressure and/or changes to the pressure of fluid and/or compressed gas inside the expandable member 110 may be analyzed to detect one or more errors. For instance, the expandable member sensor may detect when the pressure of the fluid and/or compressed gas inside the expandable member 110 is too high. In some variations, the expandable member sensor may detect an unexpected pressure change inside the expandable member 110. This may be indicative of a rupture in the expandable member 110. In some variations, if the trend of the change in pressure inside the expandable member 110 is dissimilar with the expected change based on the trend in proximal pressure or distal pressure, the expandable member sensor may detect this difference from expected change. In some variations, the expandable member sensor may detect spikes in the pressure inside the expandable member 110 during changes to the movement of the pump 108 in order to detect if the movement of the pump 108 corresponds to the expected pressure inside the expandable member 110. In some variations, the expandable member sensor may detect the amount (e.g., a volume) of fluid and/or compressed gas that has been added or removed from the expandable member 110.

Additionally or alternatively, in some variations, the blood flow control device may further optionally comprise a flow sensor (not shown in FIG. 1). The flow sensor may be integrated with and/or disposed on the expandable member 110 and may measure the amount and/or rate of blood flowing past the expandable member 110. In variations in which a blood flow sensor is not included, the amount and/or rate of blood flowing past the expandable member 110 may be determined from measurements obtained from other sensors, such as, for example, one or more of the proximal sensor, the distal sensor, and the expandable member sensor.

In some variations, the blood flow control device may further comprise a barometer (not shown in FIG. 1). The barometer may be integrated with and/or disposed within a housing of the device controller 112 and/or may be disposed within the elongate body 102 and may be communicatively coupled to the device controller 112. In some variations, the barometer may be integrated with and/or disposed within a housing of the system controller 106 and may communicatively coupled thereto. The system may also comprise a plurality of barometers, such as, for example, device controller barometer and a system controller barometer. The one or more barometers may measure ambient pressure at the location of the patient. For instance, the proximal sensor and the distal sensor may measure the absolute blood pressure. However, the barometer may measure the ambient pressure at the location of the patient. Accordingly, the blood pressure reported by the blood flow control system 100 may be blood pressure that is relative to the ambient pressure at the location of the patient (e.g., taking into consideration changes to ambient pressure as the patient is transported). Additionally or alternatively, the blood flow control device may include a gauge sensor to measure the relative pressure of the blood relative to the ambient air.

Device Controller 112

The blood flow control device 104 may comprise a device controller 112, which may be coupled to a base of the elongate body 102. The device controller 112 may be communicatively coupled to one or more sensors, such as, for example, the proximal sensor, the distal sensor, and/or the expandable member sensor. For example, the device controller 112 may be electronically coupled to the proximal sensor, the distal sensor and/or the expandable member sensor.

In some variations, the device controller 112 may comprise a housing. The housing may be coupled to the elongate body 102 and may contain a number of electronic components, such as, for example, a biasing circuit, an optional amplifier, a filter, and an Analog-to-Digital Conversion (ADC) circuit. The ADC circuit may output the readings obtained from the sensors (e.g., the proximal sensor and the distal sensor), thereby indicating a physiologic condition of the patient. For example, in some variations, the proximal sensor and the distal sensor may each include three connection wires—a power wire and two output wires. The output wires may be connected to the biasing circuit and the power wire. The biasing circuit may provide power to the power wire and appropriate resistance to the two output wires. The two output wires may be coupled to the amplifier which may amplify the differential voltage created across the two output wires. The amplifier may be coupled to the filter which may reduce high frequency and/or low frequency noise from the output of the amplifier. The output of the filter may be coupled to the Analog-to-Digital Conversion (ADC). The output of the ADC may be at a variety of rates and sample sizes indicating a physiologic condition of the patient. The device controller 112 may include any of the components and/or features described with respect to the system controller 106 described herein.

Pump 108

As depicted in FIG. 1, the blood flow control systems described herein may comprise a pump 108, which may be operably coupled to the expandable member 110 to facilitate adjusting a size thereof. The pump 108 may be contained within (e.g., within an open or closed cavity or chamber) or otherwise carried by or coupled to the housing of the device controller 112 or the system controller 106 and may be communicably coupled to one or both of the device controller 112 and the system controller 106. The pump 108 may comprise or otherwise be coupled to an elongate member comprising a lumen (e.g., tubing), which may in turn be coupled to a lumen of the elongate body of the blood flow control device (e.g., an inlet or inflation lumen). In this manner, the pump 108 may be in fluid communication with the expandable member 110.

Alternatively, a set of one or more valves may be utilized to control the flow of a compressed gas, such as carbon dioxide. In some variations, the pump may be fluidly coupled to a valve (e.g., a stopcock valve) which may regulate the flow of fluid and/or compressed gas to the expandable member 110. In some variations, the expandable element may additionally or alternatively include a shape-change material (e.g., nitinol) configured to controllably expand and contract in response to applied electrical current, voltage, temperature, or pressure, for example. Such variations may include a frame formed from the shape-change material that is attached to one or more membranes to form a "sail" that can controllably open and close according to selective shape change of the frame. Such membranes may be made from a polymeric material suitable for contact with the aorta, for example.

The size (e.g., volume) of the expandable member may be adjusted using the system and/or device controller 112, 106 and the pump 108. For example, the system and/or device controller 112, 106 may determine an amount of fluid and/or compressed gas that is to be injected into or removed from the expandable member 110 so as to adjust the size of the expandable member 110 and thereby affect blood flow. The system and/or device controller 106, 112 may control (e.g., move, modify or control a position thereof) an actuation mechanism included in the pump 108. The actuation mechanism of the pump may inject or remove the fluid and/or compressed gas from the expandable member 110 based on instructions from the system and/or device controller 106. In some variations, the actuation mechanism may comprise a plunger. Put another way, the pump 108 may include a plunger positioned within a barrel containing the fluid and/or compressed gas. In some variations, the pump 108 may be a syringe pump. The syringe pump may inject or remove fluid and/or compressed gas from the expandable member 110. In some variations, the actuation mechanism may inject the fluid and/or compressed gas into the expandable member 110 using the normal action of syringe. However, the removal of the fluid and/or compressed gas may be activated via a screw actuation. For example, the inflation may be accomplished by putting pressure on the end of the plunger so that it is inserted into the barrel of the syringe, but, once pressure is released, a screw actuator may be engaged, and deflation may occur only by rotation of the screw mechanism, which may allow for greater precision in deflation. In other variations, the pump 108 may be a peristaltic pump.

Although the above paragraph describes specific variations of the pump 108, it should be readily apparent that pump 108 may be any suitable pump operably and/or communicatively coupled to an actuation mechanism so as to inject and/or remove the fluid and/or compressed gas from the expandable member 110. In some variations, the pump 108 may be communicatively coupled to a position sensor, which may provide information on the position of a portion of the pump 108 and thus how much fluid has been delivered to the expandable member 110 as further described herein.

In some variations, the pump 108 may be operably coupled to a stepper motor and/or a controller arm. In some variations, the stepper motor and/or the controller arm may provide actuation mechanism for the pump 108. In addition to providing an actuation mechanism for the pump 108, the stepper motor and/or the controller arm may provide additional means to further adjust the volume of the expandable member 110. For instance, one or more wires may be wound around the expandable member 110. The stepper motor and/or the controller arm may be configured to tighten or loosen the wires relative to a point on the elongate body 102 so as to further adjust the volume of the expandable member 110. That is, the tightening and loosening of the wires may further adjust the expansion and/or contraction of the expandable member 110.

System Controller 106

In some variations, the blood flow control system may comprise a system controller 106 in addition to the device controller 112. The system controller 106 may be coupled to the blood flow control device 104, for example, via the device controller 112, or in variations without a device controller 112, via the elongate body 102 directly. The device controller 112 may be communicably coupled to the sensors in the system. For example, the system controller 106 may be communicably coupled to one or more of the proximal sensor, the distal sensor, the expandable member sensor, the barometer, and the flow sensor (when included), and, in variations comprising more than one controller, may be communicably coupled to the device controller 112. For example, in some variations, the proximal sensor and the distal sensor may be electronically coupled to the device controller 112, which in turn may be communicably coupled to the system controller 106.

The device controller 112 may comprise a housing, which may contain a number of electronic components, such as, for example, the biasing circuit, the amplifier, the filter, and the ADC circuit. The sensor readings extracted from the ADC circuit may be transmitted from the device controller 112 to the system controller 106.

In some variations, the device controller 112 may further comprise a motion sensor and/or a position sensor communicably coupled to the pump 108. In some variations, the position sensor may measure a position of a portion of the pump 108. For instance, the position sensor may measure a position of a plunger of a syringe pump 108. The position of the portion of the pump 108 may be used to infer the amount of fluid that has been delivered to and/or removed from the expandable member 110.

Additionally or alternatively, the device controller 112 may comprise a motion sensor (e.g., encoders such as magnetic encoder, optical encoder etc.). If the pump 108 is actuated using a motor, the encoder may monitor the movement of the motor, which may be used to determine the amount of inflation and/or deflation in the expandable member 110. In some variations, the motion sensor may be a magnetic encoder. Additionally or alternatively, the motion sensor may be an optical encoder. In some variations, the flow sensor described above may determine the amount of inflation and/or deflation in the expandable member 110.

Alternatively, the proximal sensor and the distal sensor may be electronically coupled to the system controller 106. The system controller 106 may comprise a housing. The housing may contain a number of electronic components, such as, for example, a biasing circuit, an amplifier, a filter, and an Analog-to-Digital Conversion (ADC) circuit. The ADC circuit may output the readings obtained from the sensors (e.g., the proximal sensor and the distal sensor), thereby indicating a physiologic condition of the patient. For example, in some variations, the proximal sensor and the distal sensor may each include three connection wires—a power wire and two output wires. The output wires may be connected to the biasing circuit and the power wire. The biasing circuit may provide power to the power wire and appropriate resistance to the two output wires. The two output wires may be coupled to the amplifier which may amplify the differential voltage created across the two output wires. The amplifier may be coupled to the filter which may reduce high frequency and/or low frequency noise from the output of the amplifier. The output of the filter may be coupled to the Analog-to-Digital Conversion (ADC). The output of the ADC may be at a variety of rates and sample sizes indicating a physiologic condition of the patient.

Accordingly, the sensor readings from the proximal sensor and the distal sensor may be extracted directly at the system controller 106. In some variations, the expandable member pressure sensor, the barometer, and optionally the flow sensor may transmit sensor data directly to the system controller 106. The data from the sensors in the system may be collected continuously or intermittently and may be collected over a defined period of time. In some variations, the data from the proximal sensor and the distal sensor may be collected continuously, such as for example, every 3 seconds, 4 seconds, 5 seconds, 6 seconds, 7 seconds, 8 seconds, 9 seconds, or 10 seconds (including all values and sub-ranges therein, such as, for example, between about 3 second and about 6 second, about 4 second and about 6 second, or between about 5 second or about 6 second). In some variations, the data from the proximal sensor and the distal sensor may be collected every 5 seconds at 200 Hz.

In some variations, data may be collected from the expandable member sensor continuously such as, for example, every 3 seconds, 4 seconds, 5 seconds, 6 seconds, 7 seconds, 8 seconds, 9 seconds, or 10 seconds (including all values and sub-ranges therein, such as, for example, between about 3 second and about 6 second, about 4 second and about 6 second, or between about 5 second or about 6 second).

In some variations, data from the sensors may be analyzed over a discrete period of time. For instance, the data may be analyzed for example, every 3 seconds, 4 seconds, 5 seconds, 6 seconds, 7 seconds, 8 seconds, 9 seconds, or 10 seconds (including all values and sub-ranges therein, such as, for example, between about 3 second and about 6 second, about 4 second and about 6 second, or between about 5 second or about 6 second). In some variations, the actuation mechanism to the pump 108 may include a stepper motor. In such variations, the data may be analyzed based on the motion of the stepper motor (e.g., 1300 steps per second) and/or based on the sequence of the movement of the motor (e.g., between 25-2000 milliseconds).

The system controller 106 may include one or more processors (e.g., CPU). The processor(s) may be any suitable processing device configured to run and/or execute a set of instructions or code, and may include one or more data processors, image processors, graphics processing units, digital signal processors, and/or central processing units. The processor(s) may be, for example, a general purpose processor, a Field Programmable Gate Array (FPGA), an Application Specific Integrated Circuit (ASIC), and/or the like. The processor(s) may be configured to run and/or execute application processes and/or other modules, processes and/or functions associated with the blood flow control system 100.

In some variations, the system controller 106 may run and/or execute application processes and/or other modules. These processes and/or modules when executed by a processor may be configured to perform a specific task. These specific tasks may collectively enable the system controller 106 to automatically operate and control the blood flow control system 100 while detecting errors and responding to the errors. Specifically, these specific tasks may enable the system controller 106 to detect errors and automatically adjust inflation and/or deflation of the expandable member 110 accordingly.

The system controller 106 may comprise a processor. Generally, the processor (e.g., CPU) described here may process data and/or other signals to control one or more components of the system. The processor may be configured to receive, process, compile, compute, store, access, read, write, and/or transmit data and/or other signals. In some variations, the processor may be configured to access or receive data and/or other signals from one or more of a sensor (e.g., proximal sensor, distal sensor, expandable member sensor, etc.) and a storage medium (e.g., memory, flash drive, memory card). In some variations, the processor may be any suitable processing device configured to run and/or execute a set of instructions or code and may include one or more data processors, image processors, graphics processing units (GPU), physics processing units, digital signal processors (DSP), analog signal processors, mixed-signal processors, machine learning processors, deep learning processors, finite state machines (FSM), compression processors (e.g., data compression to reduce data rate and/or memory requirements), encryption processors (e.g., for secure wireless data and/or power transfer), and/or central processing units (CPU). The processor may be, for example, a general-purpose processor, Field Programmable Gate Array (FPGA), an Application Specific Integrated Circuit (ASIC), a processor board, and/or the like. The processor may be configured to run and/or execute application processes and/or other modules, processes and/or functions associated with the system. The underlying device technologies may be provided in a variety of component types (e.g., metal-oxide semiconductor field-effect transistor (MOSFET) technologies like complementary metal-oxide semiconductor (CMOS), bipolar technologies like generative adversarial network (GAN), polymer technologies (e.g., silicon-conjugated polymer and metal-conjugated polymer-metal structures), mixed analog and digital, and/or the like.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

Generally, the blood flow control systems described here may comprise a memory configured to store data and/or information. In some variations, the memory may comprise one or more of a random access memory (RAM), static RAM (SRAM), dynamic RAM (DRAM), a memory buffer, an erasable programmable read-only memory (EPROM), an electrically erasable read-only memory (EEPROM), a read-only memory (ROM), flash memory, volatile memory, non-volatile memory, combinations thereof, and the like. In some variations, the memory may store instructions to cause the processor to execute modules, processes, and/or functions associated with a blood flow control device, such as signal waveform generation, expandable element control, data and/or signal transmission, data and/or signal reception, and/or communication. Some variations described herein may relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. In some variations, the system controller 106 and the device controller 112 may be integrated into a single controller.

Communication Device or Module

Figure 2:
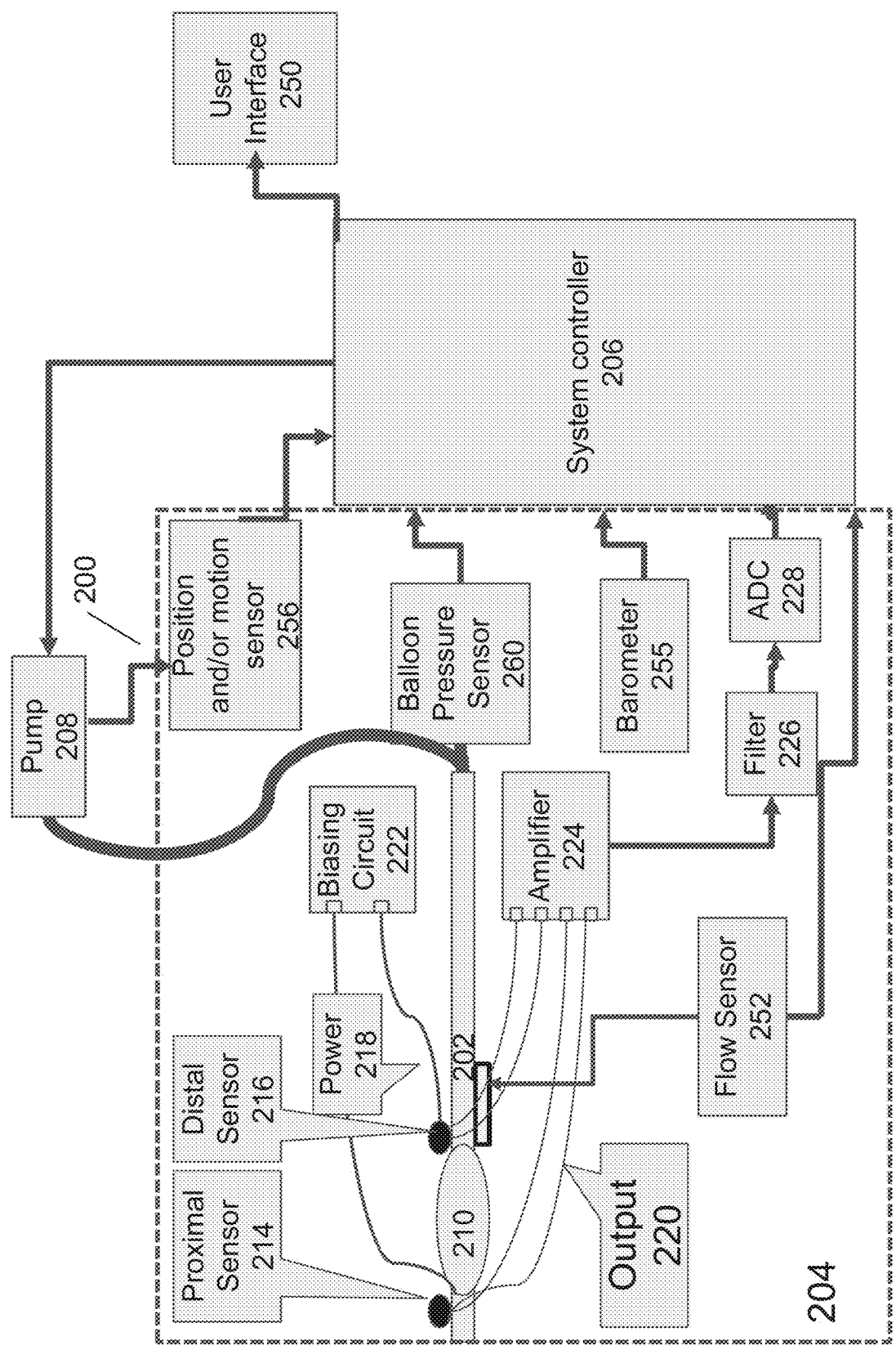
FIG. 2 is a schematic of an exemplary variation of a blood flow control system.

In some variations, the system controller 106 may include at least one communication device or module (e.g., communication module 126 as shown in FIG. 2), such as a wireless communication module to communicate with one or more other devices. For example, the communication module may be configured to communicate data (e.g., sensor data, target blood pressures, target blood pressure ranges, state of the blood flow control system, such as internal temperature of blood flow control system, battery charge level of the blood flow control system, time of day, and/or properties of the blood flow control system, such as hardware and firmware revision number of the blood flow control system, system capabilities, etc.) and/or determinations or calculations made based on the data (e.g. errors, physiologic states, clinical decision support), to one or more devices, such as, for example, an external computer, a mobile device (e.g., a smartphone), a tablet, or the like. The communication device may comprise a network interface configured to connect the blood flow control device to another device or system (e.g., Internet, remote server, database) by wired or wireless connection. In some variations, the blood flow control device and/or system may be in communication with other devices (e.g., cell phone, tablet, computer, smart watch, and the like) via one or more wired and/or wireless networks. In some variations, the network interface may comprise one or more of a radiofrequency receiver/transmitter, an optical (e.g., infrared) receiver/transmitter, and the like, configured to communicate with one or more devices and/or networks. The network interface may communicate by wires and/or wirelessly with one or more of the blood flow control device, system controller 106, network, database, and server.

The network interface may comprise RF circuitry configured to receive and/or transmit RF signals. The RF circuitry may convert electrical signals to/from electromagnetic signals and communicate with communications networks and other communications devices via the electromagnetic signals. The RF circuitry may comprise well-known circuitry for performing these functions, including but not limited to an antenna system, an RF transceiver, one or more amplifiers, a tuner, one or more oscillators, a mixer, a digital signal processor, a CODEC chipset, a subscriber identity module (SIM) card, memory, and so forth.

Wireless communication through any of the devices may use any of plurality of communication standards, protocols and technologies, including but not limited to, Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (WiFi) (e.g., IEEE 802.11a, IEEE 802.11b, IEEE 802.11g, IEEE 802.11n, and the like), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol. In some variations, the devices herein may directly communicate with each other without transmitting data through a network (e.g., through NFC, Bluetooth, WiFi, RFID, and the like).

The communication device or module may include a wireless transceiver that is integrated into the system controller 106. However, the blood flow control system may additionally or alternatively include a communication module that is separate from the system controller 106.

User Interface

In some variations, the blood flow control system 100 may include a user interface communicably coupled to the system controller 106 and/or the device controller 112. In some variations, the user interface may be a display on the device controller 112 such that the device controller 112 may be communicably coupled to the system controller 106, or vice versa. Alternatively, the user interface may be a display on any suitable computing device (e.g., computer, smartphone, tablets, etc.) communicably coupled to the system controller 106, via, e.g., the communication device or module described herein.

In some variations, the user interface may comprise an input device (e.g., touch screen) and output device (e.g., display device) and be configured to receive input data from one or more of the blood flow control device 104, communications device, system controller 106, pump 108, and the sensor(s). For example, operator control of an input device (e.g., keyboard, buttons, touch screen) may be received by the user interface and may then be processed by the system controller 106 for the user interface to output a control signal to the system controller 106, blood flow control device 104, and/or pump 108. Some variations of an input device may comprise at least one switch configured to generate a control signal. For example, an input device may comprise a touch surface for an operator to provide input (e.g., finger contact to the touch surface) corresponding to a control signal. An input device comprising a touch surface may be configured to detect contact and movement on the touch surface using any of a plurality of touch sensitivity technologies including capacitive, resistive, infrared, optical imaging, dispersive signal, acoustic pulse recognition, and surface acoustic wave technologies. In variations of an input device comprising at least one switch, a switch may comprise, for example, at least one of a button (e.g., hard key, soft key), touch surface, keyboard, analog stick (e.g., joystick), directional pad, mouse, trackball, jog dial, step switch, rocker switch, pointer device (e.g., stylus), motion sensor, image sensor, and microphone. A motion sensor may receive operator movement data from an optical sensor and classify an operator gesture as a control signal. A microphone may receive audio data and recognize an operator voice as a control signal.

A haptic device may be incorporated into one or more of the input and output devices to provide additional sensory output (e.g., force feedback) to the operator. For example, a haptic device may generate a tactile response (e.g., vibration) to confirm operator input to an input device (e.g., touch surface). As another example, haptic feedback may notify that operator input is overridden by the pulsed electric field device.

In some variations, a user may input target value, target range, expected value, expected range, threshold value, threshold range and/or the like for various sensor data via the user interface. For instance, a user may input target/expected/threshold values associated with proximal systolic pressure, proximal diastolic pressure, PMAP, distal systolic pressure, distal diastolic pressure, DMAP, expandable member pressure, expandable member volume, etc via the user interface.

In some variations, the user interface may display to the user blood flow state, graphs of one or more pressure waveforms, proximal pressure, distal pressure, expandable member volume, errors, etc. to the user. In some variations, the user interface may display at least one alert to the user. The alerts may be visual prompts such as text, icons, a combination thereof, etc. Alternatively, the input data, blood flow state, alert, graphs, etc., may be displayed on the user interface via audio prompts such as tones, spoken words, a combination thereof, etc. In some variations, the user interface may include display, such as a liquid crystal display (LCD) panel, a light emitting diode (LED) array, E-link gateway, or other means for displaying numbers, letters, graphs, and/or icons. In some variations, the user interface may include an audio output such as an audio speaker, that produces single tones, sequences of tones, or enunciated messages.

In some variations, errors detected and alerts transmitted by the system controller (described further below) may be ranked and categorized by level of importance (e.g., how harmful the error may be to the efficacy of the blood flow control system and/or the therapeutic procedure) and/or urgency, such as, for example, as high priority alerts, medium priority alerts, and low priority alerts. In some variations, alerts with different importance levels and/or urgency (e.g., high priority alerts, medium priority alerts, and low priority alerts) may be displayed and/or transmitted via the user interface differently. For instance, a high priority alert may be displayed and/or transmitted via the user interface in a manner so as to catch the attention of the user. For example, an array of red lights may continuously blink via the user interface to indicate a high priority alert. Additionally or alternatively, a loud audio tone, or a sequence of audio tones, may be transmitted via the user interface that may indicate the high priority alert. In contrast, for example, low priority alerts may appear as text on a visual display without an array of colored blinking lights, such as red lights.

Figure 8:
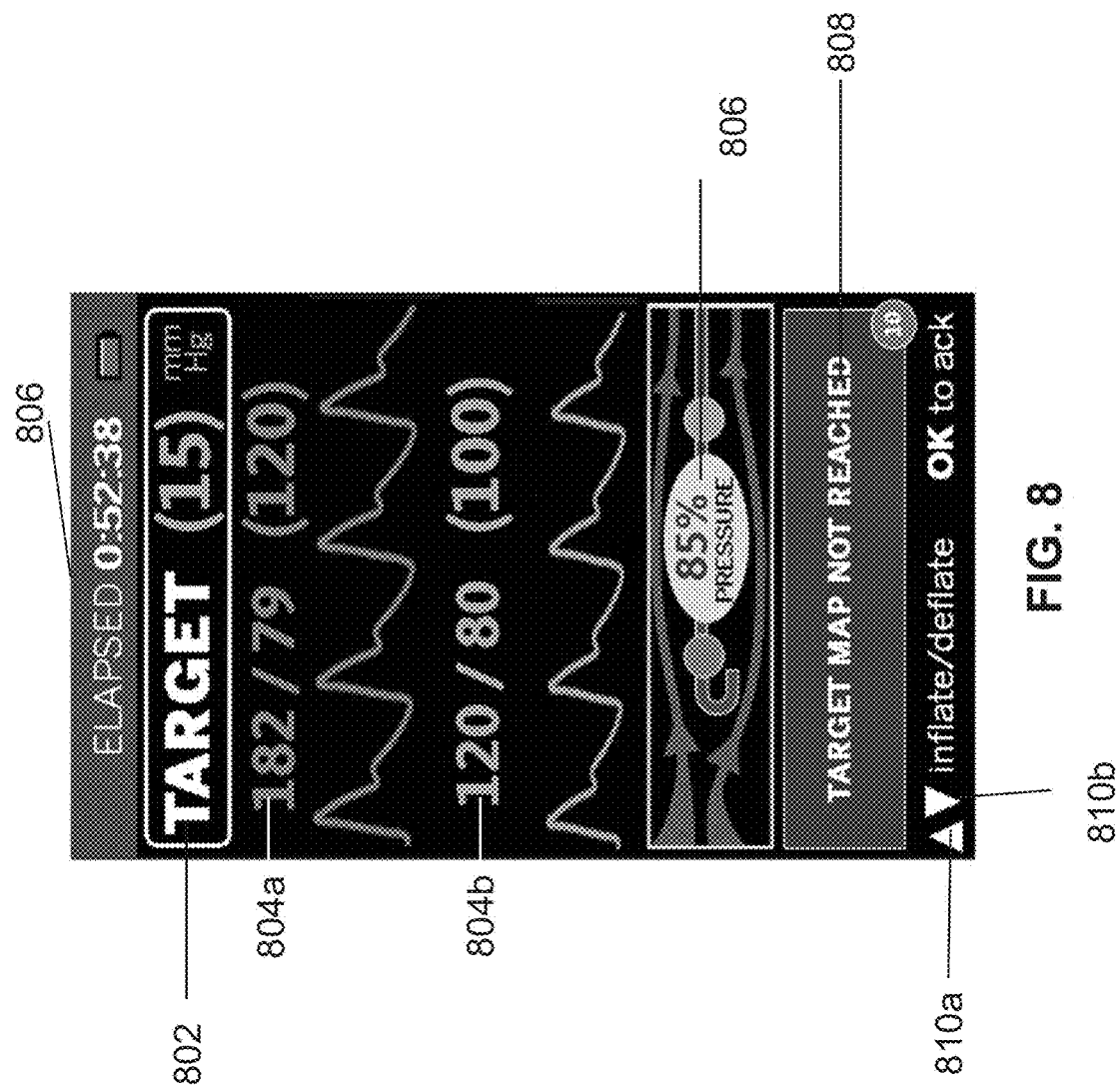
FIG. 8 is an exemplary variation of a user interface used by a blood flow control system to receive data and/or transmit information to a user.

FIG. 8 illustrates an exemplary variation of a user interface with a display that displays blood pressure measurements, expandable member pressure measurements, and alerts. In FIG. 8, the elapsed time since the procedure begun may be displayed as 801. A target value and/or target range associated with specific sensor data may be represented via the user interface. For example, 802 may represent the target blood pressure value that the blood vessel may have to reach in order for the therapeutic intervention to be a success. The display may also comprise the measured proximal pressure 804a and the measured distal pressure 804b, as well as the associated waveforms 812a and 812b. In some variations, the proximal pressure 804a and the associated waveform 812a and the distal pressure 804b and the associated waveform 812b may be displayed in a way such that they can be easily distinguished from each other. For example, the proximal pressure 804a and the associated waveform 812a may be in a first color (e.g., red) while the distal pressure 804b and the associated waveform 812b may be in a second color (e.g., blue). In some variations, the display may also comprise the expandable member pressure 806. For instance, in this example, the expandable member pressure 806 displayed as a percentage, e.g., 85 percent, indicating that the expandable member has reached 85 percent of the maximum allowable pressure for the expandable member. The display may further comprise any applicable alerts 808, such as, for example, "target MAP not reached". It should be appreciated that while the display in FIG. 8 depicts a target MAP error, alerts related to any of the errors described herein may be depicted to communication such alerts to a user. The display may further comprise an indication of the number of currently activate alerts or errors 814, depicted in this example as a numerical value (e.g., 10) contained within a solid circle. In some variations, the display may further comprise one or more buttons 801a and 801b, which may be in the form of arrows or other suitable graphical elements. A user may interact with the button in order to actuate the pump 108 to inflate and/or deflate the expandable member. For example, pressing or clicking 801a may cause the pump to inflate the expandable member while pressing or clicking 801b may cause the pump to deflate the expandable member.

FIG. 2 is a schematic of an exemplary variation of a blood flow control system 200 (e.g., structurally and/or functionally similar to blood flow control system 100 in FIG. 1). As depicted there, the blood flow control system 200 may include a blood flow control device 204 (e.g., structurally and/or functionally similar to blood flow control device 104 in FIG. 1), system controller 206 (e.g., structurally and/or functionally similar to system controller 106 in FIG. 1), a pump 208 (e.g., structurally and/or functionally similar to pump 108 in FIG. 1), and a user interface 250. The blood flow control device 204 may include an expandable member 210 (e.g., structurally and/or functionally similar to expandable member 110 in FIG. 1), a elongate body 202 (e.g., structurally and/or functionally similar to elongate body 102 in FIG. 1), a proximal sensor 214, a distal sensor 216, and an expandable member sensor 206. In some variations, the blood flow control device 204 may further comprise a flow sensor 252 and the system controller 206 may comprise a barometer 255.

The proximal sensor 214 and the distal sensor 216 may be any sensors suitable to measure blood pressure within a vessel. In some instances, the proximal sensor 214 and the distal sensor 216 may be integrated into the elongate body 202 of the blood flow control device 204. The signals from the proximal sensor 214 and distal sensor 216 may be processed and sent to the system controller 206. For example, the proximal sensor 214 and the distal sensor 216 may each be connected to three connection wires: a power wire 218 and two output wires 220. The two output wires 220 may be connected to a biasing circuit 222. The biasing circuit 222 may provide power to the power wire 118 and may provide resistance to the two output wires 220. The two output wires 220 may be coupled to an amplifier 224, which may amplify the differential voltage created across the two output wires 220. The amplifier 224 may be coupled to a filter 226. The filter 226 may reduce high frequency and/or low frequency noise from the output of the amplifier 224. In some variations, the filter 226 may be split (e.g., a first low-pass filter, a second low-pass filter, etc.). For instance, the filter 226 may include a first low-pass filter. The output of the filter 226 and/or the first low-pass filter may be coupled to an Analog-to-Digital Conversion (ADC) 228. The output of the ADC 228 may be at a variety of rates and sample sizes. The output of the ADC may in some variations be coupled to a second low-pass filter that may then be coupled to a system controller 206. Alternatively, the output of the ADC may be communicably coupled to a system controller 206. The system controller 206 may therefore process the sensor data from the proximal sensor 214 and the distal sensor 216 to determine proximal average such as proximal systolic pressure, proximal diastolic pressure, and current PMAP as well as distal average such as distal systolic pressure, distal diastolic pressure, and current DMAP. The proximal average and the distal average may be determined every few heartbeats or every few seconds. It should be readily understood that other arrangements of sensors may be possible. For instance, the proximal sensor 214 and the distal sensor 216 may be integrated with one or more of the components biasing circuit 222, filter 226, amplifier 224, or ADC 228.

In some variations, a user may set a target blood pressure or target blood pressure range (e.g., target DMAP or target DMAP range) using a user interface 250. The target blood pressure may be a numerical representation of a user-intended blood pressure. Therefore, the blood flow control system 200 may activate a pump 208 to expand and/or contract the expandable member 210 to impede blood flow through a vessel of a patient such that the measured blood pressure (e.g., measured DMAP) may be increased or decreased until it matches the target blood pressure or falls within the target blood pressure range (e.g., target DMAP or target DMAP range).

In some variations, the system controller 206 may be communicably coupled to a user interface 250. The user interface may display graphs of pressure waveforms, indicate blood flow state, indicate and alert, etc. In some variations, the user interface 250 may allow users to input target values and/or target ranges. The system controller 206 may perform power-up check tests, runtime check tests, and physiologic condition check as discussed below using the target values and/or target ranges to identify errors and modify the behavior of the blood flow control system 200 based on the errors.

Measurements Determined by System Controller 106

Below are non-limiting examples of measurements that may be determined by the system controller 106 based on sensor data from the proximal sensor, the distal sensor, the expandable member sensor, the barometer, the pump position sensor and optionally the flow sensor. While described below in relation to the system controller 106, it should be appreciated that or more of the measurements may be determined by the device controller 112.

Proximal Average Pressure—The proximal average pressure measurement includes one or more of proximal systolic pressure, proximal diastolic pressure, and current proximal mean arterial pressure (PMAP). In some variations, PMAP may be the arithmetic mean of pressure samples received from the proximal sensor over a time window. For instance, as a non-limiting example, if 800 pressure samples were captured at 200 Hz over a 4 second time window, then the PMAP may be the arithmetic mean of the 800 samples. In some variations, proximal systolic pressure may be the average of peaks in pressure samples collected over the time window. For instance, if three full heartbeats appeared in the 4 second time window, the proximal systolic pressure may be the arithmetic mean of the three peak values. In some variations, proximal diastolic pressure may be the average of the valleys in the pressure samples collected over the time window. For instance, the proximal diastolic pressure may be the arithmetic mean of the three valley values that may have appeared in the 4 second time window.

It should be readily apparent that the proximal average pressure may be calculated in any suitable manner. For instance, instead of receiving samples over a time window, the proximal average pressure may be calculated based on samples received for one or more heartbeats, such as each heartbeat, two heartbeats, three heartbeats, etc. Similarly, proximal average pressure may be the median, mode, etc., of pressure samples received over a time window and/or during one or more heartbeats.

Proximal Pressure Pulsatility—Proximal Pressure pulsatility may indicate changes to the proximal systolic pressure, proximal diastolic pressure, and/or PMAP over a defined time window. For example, proximal pressure pulsatility may be an absolute difference of each of/combination of proximal systolic pressure, proximal diastolic pressure, and/or PMAP over a defined period of time. For instance, proximal pressure pulsatility may be the arithmetic difference between the proximal systolic pressure and the proximal diastolic pressure. In some variations, proximal pressure pulsatility may be a ratio of each of/a combination of proximal systolic pressure, proximal diastolic pressure, and/or PMAP over a time window.

Distal Average Pressure—The distal average pressure measurement includes one or more of distal systolic pressure, distal diastolic pressure, and current distal mean arterial pressure (DMAP). In some variations, DMAP may be the arithmetic mean of pressure samples received from the distal sensor over a time window. For instance, as a non-limiting example, if 800 pressure samples were captured at 200 Hz over a 4 second time window, then the DMAP may be the arithmetic mean of the 800 samples. In some variations, distal systolic pressure may be the average of peaks in pressure samples collected over the time window. For instance, if three full heartbeats appeared in the 4 second time window, the distal systolic pressure may be the arithmetic mean of the three peak values. In some variations, distal diastolic pressure may be the average of the valleys in the pressure samples collected over the time window. For instance, the distal diastolic pressure may be the arithmetic mean of the three valley values that may have appeared in the 4 second time window.

It should be readily apparent that the distal average pressure may be calculated in any suitable manner. For instance, instead of receiving samples over a time window, the distal average pressure may be calculated based on samples received for one or more heartbeats, such as each heartbeat, two heartbeats, three heartbeats, etc. Similarly, distal average pressure may be the median, mode, etc., of pressure samples received over a time window and/or during one or more heartbeats.

Distal Pressure Pulsatility—Distal pressure pulsatility may indicate changes to the distal systolic pressure, distal diastolic pressure, and/or DMAP over a defined time window. For example, distal pressure pulsatility may be an absolute difference of each of/combination of distal systolic pressure, distal diastolic pressure, and/or DMAP over a defined period of time. For instance, distal pressure pulsatility may be the arithmetic difference between the distal systolic pressure and the distal diastolic pressure. In some variations, distal pressure pulsatility may be a ratio of each of/a combination of distal systolic pressure, distal diastolic pressure, and/or DMAP over a time window.

It should be readily understood that "blood pressure measurement" as referred to herein may include one or more of, or a combination of one or more of, proximal systolic pressure, proximal diastolic pressure, PMAP, proximal average pressure, proximal pressure pulsatility, distal systolic pressure, distal diastolic pressure, DMAP, distal average pressure, and distal pressure pulsatility.

Expandable Member Pressure—The expandable member pressure measurement may indicate the pressure of fluid and/or compressed gas in the expandable member 110. The expandable member pressure measurement may be determined from the sensor data obtained from the expandable member sensor.

Expandable Member Volume—The expandable member volume measurement may indicate the amount (e.g., a volume) of fluid and/or compressed gas that may have been added or removed from the expandable member 110. In some variations, the expandable member volume may be determined from the encoder data (e.g., magnetic encoder, optical encoder, etc.) that may measure the movement of the stepper motor (e.g., actuation mechanism to the pump 108).

Expandable Member Mean Arterial Pressure—The Expandable Member Mean Arterial Pressure (Expandable member MAP) may be the arithmetic mean of pressure samples (e.g., pressure sample from above the expandable member and pressure sample from below the expandable member) over a time period. For instance, the expandable member sensor may obtain expandable member pressure samples from above the expandable member and from below the expandable member. The expandable member MAP may be the arithmetic mean of these two pressure samples. As a non-limiting example, if 800 pressure samples were captured at 200 Hz over a 4 second time window, then the Expandable member MAP may be the arithmetic mean of the 800 samples.

Blood Flow Rate—The blood flow rate measurement may indicate the amount or rate of blood flowing past the expandable member 110. In some variations, the blood flow rate may be determined from the sensor data obtained from the flow sensor. Alternatively, the blood flow rate may be determined based on various other measurements such as proximal average pressure, distal average pressure, expandable member pressure, expandable member volume, and loss of pulsatility or change in shape of the waveforms reported by the distal average pressure.

Blood Flow State—The blood flow state may indicate the relative occlusion of the blood vessel provided by the blood flow control device (e.g., expandable member). Put another way, the blood flow state may indicate the level of blood flow in the blood vessel (e.g., high flow or low flow) while the blood flow control device is in use. Thus, the blood flow state may indicate whether there is full occlusion, partial occlusion, or no occlusion in the blood vessel. In some variations, the systems and methods described herein may utilize two blood flow states: Occlusion and Flow. The blood flow state may be determined based on a combination of sensor data including but not limited to expandable member pressure, a rate of change the expandable member sensor data, the pulsatility or cyclical change in the expandable member pressure, expandable member volume, a comparison of the expandable member volume at various points in time, and loss of pulsatility or change in shape of the waveforms reported by the distal average pressure.

In variations in which an Occlusion state and a Flow state are utilized, the system may determine which state is applicable by comparing the blood flow rate to a threshold. For instance, when the blood flow rate is below the threshold, the blood flow state may be designated to be Occlusion, and when the blood flow rate is above the threshold, the blood flow state may be designated to be Flow. In another variation, the system may determine the blood flow state using a difference between two blood pressure measurements, such as, for example, distal systolic pressure and DMAP. This difference may be compared to one or more threshold values, and the blood flow state may be designated to be Occlusion if the pressure difference is below a threshold value and may be designated to be Flow if the pressure difference is above the same, or a different, threshold value. For example, in one variation, the blood pressure measurements utilized to determine blood flow state may be distal systolic pressure and DMAP. In this variation, if the difference between distal systolic pressure and DMAP is less than about 2 mmHg, the blood flow state may be designated as Occlusion. However, if the difference between the distal systolic pressure and DMAP is greater than about 4 mmHg, the blood flow state may be designated as Flow. If the difference between the distal systolic pressure and DMAP is between about 2 mmHg and about 4 mmHg, the blood flow state may optionally be designated as a third state, such as, for example, Low Flow.

In the above example, the blood flow rate to designate the blood flow state as Occlusion and the blood flow rate to designate the blood flow state as Flow was derived from tests conducted using animal data.

When the blood flow rate is not determined, the blood flow state may be designated as indeterminate or/and an alert may be provided to a user to check for occlusion. In some variations, as mentioned above, additional states may be designated for the blood flow state. For example, instead of two states (Occlusion and Flow) there may be several additional states to indicate different levels of flow, such as, for example, High Flow and/or Low Flow. These additional states may be determined using thresholds as described above with respect to the Occlusion and Flow states.

In some variations, the blood flow control system 100 may include a timer to determine the elapsed time at different blood flow states. Put differently, the amount of time in each blood flow state may be measured and/or recorded by the blood flow control system 100 and reported to a user via the user interface.

Total Elapsed Time—The total elapsed time may indicate the elapsed time from the start of use of the blood flow control system 100. For instance, the total elapsed time may indicate the elapsed time from the point at which the blood flow control system 100 is turned on. Alternatively, the total elapsed time may indicate the elapsed time since the start of a therapeutic procedure using the blood flow control system 100. For example, the total elapsed time may indicate the elapsed time from the point at which the expandable member 110 is advanced into a blood vessel of a patient.

Total Time at Occlusion—The total time at Occlusion may indicate the amount of time the blood flow state may be designated as Occlusion. In some variations, if the blood flow state is designated as Occlusion multiple times during a single procedure, the total time at Occlusion may be the cumulative total of each time the blood flow state is designated as Occlusion. In some variations, each time the blood flow state is designated as Occlusion, the total time at Occlusion may be indicative of the amount of time spent in the occlusion state. For example, if the system detects a blood flow state of Occlusion for 3 minutes, followed by a blood flow state of Flow for 3 minutes, followed by a blood flow state of Occlusion for 2 minutes, the system will calculate the total time at Occlusion to be 5 minutes.

Total Time not at Occlusion—The total time not at Occlusion may indicate the amount of time the blood flow state may not be designated as Occlusion. In some variations, if the blood flow state is designated as Occlusion multiple times during a single procedure, the total time not at Occlusion may be the cumulative total of each time the blood flow state is not designated as Occlusion. In some variations, each time the blood flow state is not designated as Occlusion, the total time spent in that state (i.e., not the occlusion state) may be indicative of the total time not at occlusion. For example, if the system detects a blood flow state of Occlusion for 3 minutes, followed by an indeterminate state for 2 minutes, followed by a Flow state for 3 minutes, the system will calculate the total time not at Occlusion to be 5 minutes Automatically Controlling Expandable Member 110

In some variations, the blood flow control system may be configured to operate in an automatic mode and in a manual mode. In the automatic mode, the system controller 106 may control the actuation mechanism of the pump 108 to inflate and deflate the expandable member. Therefore, a volume of the expandable member may be controlled by the system controller 106.

In the manual mode, the system controller 106 may not autonomously control the actuation mechanism of the pump. Instead, the system controller 106 may include one or more buttons (e.g., on the surface of the system controller, on a user interface, etc.) that may be operably and/or communicably coupled to the actuation mechanism of the pump. A user may press the one or more buttons in order to control the actuation mechanism so as to inflate and deflate the expandable member. Thus, the manual mode requires user input to control the expandable member 110. It should be readily apparent that the manual mode of operation is different from a user "manually" controlling the pump without use of the system controller 106. In the manual mode of operation, the user may use the system controller 106 to inflate and deflate the expandable member. In contrast, in instances in which the system controller 106 may shutdown the operation of the blood flow control system, a user may detach the pump 108 from the blood flow control system and may "manually" inflate and deflate the expandable member without using the controller 106 or a user interface of the blood flow control system.

In order to automatically control the expandable member, in some variations, the system may receive a target blood pressure or target blood pressure range. In some variations, the target blood pressure and/or target blood pressure range may be provided to the system controller 106 by a user via a user interface. Alternatively, the system controller 106 may automatically predict a target blood pressure and/or target blood pressure range based on analysis of prior data. For instance, the system controller 106 may determine a pressure range during which a patient was previously stable. The target ranges may be determined based on this determination. For instance, in a non-limiting example, if the distal pressure was determined to be 25 mmHg and the proximal average pressure was stable, then the distal target pressure may be determined to be 25 mmHg and/or the proximal average pressure range at which the stability was exhibited may be determined as the target pressure range for the proximal average pressure. The target blood pressure or target blood pressure range may indicate the blood pressure (s) to be achieved in the blood vessel by therapeutic intervention of the expandable member 110. In the absence of any error condition, the system controller 106 may measure or determine the patient's current blood pressure and compare the measured or determined blood pressure to the target blood pressure or range. If the measured blood pressure is higher or lower than the target blood pressure, or outside the target blood pressure range, the system controller 106 may determine a size of the expandable member 110, or how to adjust the size of the expandable member, to achieve the target blood pressure or a value within the target blood pressure range.

The blood pressure may include any number of blood pressure values, including but not limited to, proximal systolic pressure, proximal diastolic pressure, proximal pressure pulsitility, PMAP, distal systolic pressure, distal diastolic pressure, distal pressure pulsitility, and/or DMAP.

For example, in one variation, the blood pressure used to automatically control the expandable member may be DMAP. In this variation, the system may receive a target DMAP (e.g., a user may set a target DMAP via the user interface) and the system may measure the patient's current DMAP (e.g., based on distal sensor data). If the current DMAP is higher than the target DMAP, the system controller 106 may determine the size of the expandable member 110 that will achieve the desired DMAP. For example, in variations comprising an inflatable balloon, the system controller 106 may determine an amount of fluid and/or compressed gas to be injected into the expandable member 110 to bring the currently measured DMAP to the target DMAP. The system controller 106 may then control the actuation mechanism associated with the pump 108 such that the pump 108 injects the determined amount of fluid and/or compressed gas into the expandable member 110. This inflation of the expandable member 110 may reduce the blood flowing past the expandable member 110, and thus reduce the current DMAP. Conversely, if the current DMAP is lower than the target DMAP, the system controller 106 may determine the amount of fluid and/or compressed gas to be removed from the expandable member 110 so that the current DMAP matches the target DMAP. The system controller 106 then controls the actuation mechanism associated with the pump 108 such that the pump 108 removes the determined amount of fluid and/or compressed gas from the expandable member 110. With the reduced volume of the expandable member 110, more blood may flow past the expandable member 110 and the current DMAP may increase. In this manner, the blood flow control system 100 may activate the pump 108 to adjust the size of the expandable member 110 (e.g., inflate or deflate the expandable member 110) as needed to impede or allow blood flow in the patient such that the current DMAP is increased or decreased until it matches the target DMAP or is within a target DMAP range.

In some variations, the distal sensor may show reduced pulsatility as the expandable member 110 is inflated. The pulsatility may continue to decrease as greater opposition of the expandable member 110 is made against the wall of the vessel. The relationship in loss of pulsatility in distal systolic pressure, distal diastolic pressure, and the change in the rate of increase of pressure in the expandable member 110, and the increase in current PMAP may all independently be predictive of complete vessel occlusion.

Detecting Errors

As mentioned above, in some variations, the system controller 106 may compare one or more measurements obtained or determined from the sensor data (described above) to a target blood pressure range and/or a target blood pressure value. If the measurements do not match the target blood pressure and/or fall outside the target blood pressure range, the system controller 106 may adjust the expansion and/or contraction of the expandable member 110 so that the subsequent measurements reach the target blood pressure and/or fall within the target blood pressure range However, if after adjusting the expandable member 110, the subsequent measurements still do not reach the target blood pressure and/or still fall outside the target blood pressure range, the system controller 106 may detect an error condition. Based on the error condition/type of error detected, system controller 106 may inhibit at least one function of the blood flow control system 100 and/or may provide an alert to the user.

Inhibiting at Least One Function of the Blood Flow Control System

As mentioned above, when certain error conditions are detected, the system controller 106 may inhibit at least one function of the blood flow control system 100. In some variations, inhibition of at least one function of the blood flow control system 100 may comprise shutting down the system. In such variations, a user may detach the pump from the blood flow control system 100 and may manually inflate and deflate the expandable member 110. In other variations, inhibition of at least one function of the blood control system may comprise transitioning the system from automatic to manual mode. In some variations, inhibiting at least one function may include inhibiting automatic inflation and/or automatic deflation of the expandable member 110. For instance, if the expandable member pressure reaches a maximum inflation value, inhibiting the at least one function may comprise inhibiting automatic inflation but continuing to automatically deflate the expandable member 110. In some variations, inhibiting at least one function of the blood flow control system may comprise disabling a component of the blood flow control system, such as, for example, pump related operations (e.g., actuation mechanism, motor operatively coupled to the pump, a battery powering the pump, an external battery to the blood flow control system, and/or the system controller 106). In some variations, even if a component is disabled, the user interface may display waveforms, pressures, proximal average pressure, distal average pressure, expandable member pressure, state of the battery of the blood flow control system, etc. In some variations, when a component is disabled, it can no longer be used in the system until the component and/or entire system is reset (e.g., by user input, by rebooting the system, etc.).

Shutting Down Blood Flow Control System

There are several errors that may result in a system shutdown (system entering a shutdown mode). For example, in some variations, if the error is related to damage of one or more components within the blood flow control system including within the blood flow control device (e.g., damage of distal sensor, proximal sensor, expandable member sensor, etc.) prior to the use of the blood flow control device 104 (e.g., prior to placing the expandable member 110 in a patient's blood vessel), the system controller 106 may shutdown the blood flow control system 100. As another example, if during use of the blood flow control device 104 (e.g., during the therapeutic treatment) an error indicative of the expandable member 110 reaching maximum inflation and/or maximum position is detected, the system controller 106 may inhibit automatic inflation and/or automatic deflation respectively of the expandable member 110.

As used herein, a system shutdown refers to preventing use of all or a portion of the blood flow control system 100 (e.g., by turning off or otherwise). Following a shutdown of the blood flow control system, the user interface and/or controller(s) may no longer be functional to control the blood flow control device and the user interface may no longer provide data from the sensors. In some variations, following a shutdown of the blood flow control system, the controller(s) may not be functional however the user interface and/or the sensors may be functional. In such variations, the user interface may display the sensor data, however, the controller(s) may not control the inflation and deflation of the expandable member. In these variations, inflation and deflation of the expandable member may be performed by hand (as opposed to via the controller), for example, by actuating the syringe by hand.

Thus, if a user would like to continue to provide treatment with the blood flow control device, the user may need to decouple the pump 108 from the system controller 106 (e.g., decouple the pump 106 from an actuation mechanism controlled by the system controller 106). Additionally, as the blood flow control system no longer provides measurement data or allows for control and/or adjustment of the blood flow control device using the system while shutdown, the user may have to manually monitor the physiologic conditions of the patient and manually adjust a size of the expandable member (e.g., by manually injecting and/or removing the fluid and/or compressed gas using the pump).

Transitioning from Automatic Mode to Manual Mode

There are additionally or alternatively several errors that may result in the system automatically transitioning from the automatic mode to the manual mode. In the automatic mode, the adjustment and/or control of the expandable member 110 (e.g., expansion and contraction) may be controlled by the system controller 106 automatically. For example, in the automatic mode, the system controller 106 may automatically control the actuation mechanism associated with the pump 108 to control the amount of fluid and/or compressed gas that may be injected or removed from the expandable member 110 based on the data received from the one or more sensors in the system. In contrast, in the manual mode, the adjustment and/or control of the expandable member 110 may be controlled manually using the system controller 106. For example, the user may control a size of the expandable member 110 using the user interface, which as described in more detail herein, may comprise user inputs such as, for example, buttons. The user inputs may communicate with the system controller 106, which may control the pump 108 (e.g., via the actuation mechanism). Put another way, the user may utilize the user interface to manually adjust expansion and/or contraction of an expandable member 110 using the system controller 106 and the pump 108 (e.g., as a result of user input via the user interface, the system controller 106 may actuate the pump 108).

Thus, in contrast to when the system is shutdown, in manual mode, measurements and/or other data from one or more (e.g., all) of the sensors continues to be provided to the user via, e.g., the user interface, and the system controller 106 continues to be functional to control a size of the expandable element, albeit manually. The user may provide information to the system, e.g., via the user interface, and may manually control the size of the expandable member 110 using, e.g., user inputs on the user interface, which result in the system controller 106 actuating the pump 108. In the manual mode, the system controller 106 will not automatically adjust a size of the expandable member 110 based on sensor data. This is additionally in contrast to the automatic mode, in which in the system is not only receiving and display or otherwise providing data to the user, it is additionally automatically controlling a size of the expandable member 110 based on the received data.

When the system controller 106 transitions to manual mode, the system controller 106 stops automatically controlling the actuation mechanism of the pump 108. In the manual mode, a user may push the push buttons on the system controller 106 to actuate the pump 108 in order to adjust the expansion and contraction of the expandable device 110. In this manner, the actuation mechanism of the pump 108 may be controlled manually using the system controller 106.

Transmitting Alerts to a User

The system may also detect several errors that result in the system providing an alert to the user, but do not otherwise inhibit a function of the system. In some variations, however, the system may detect one or more errors that result in both the system providing an alert to the user and the system inhibiting automated adjustment of the size of the expandable member until a user instructs the system to restart automated adjustment. When these errors occur, the system may not automatically transition to manual mode, but may hold the size/position of the expandable member 110 constant until additional user input is provided.

Examples of errors that may result in transmitting an alert to a user, with or without maintaining a size of the expandable member until further instructed, include but are not limited to user defined errors (e.g., setting a facially incorrect or abnormal target blood pressure or target blood pressure range).

Types of Errors

As discussed above, the blood flow control system 100 may identify various errors. These errors may be due to damage of one or more components within the blood flow control system 100 during shipment and/or due to continuous wear and tear of the components. Additionally or alternatively, these errors may also arise due to issues while performing the therapeutic procedure (e.g., placing the expandable member 110 in an undesirable or incorrect location, issues with inserting the expandable member 110 into a patient's body, electrical interference with other devices (e.g., electrocautery devices), clotting, damage to sensors, setting a wrong target value, etc.).

Some non-limiting examples of various errors detected by the blood flow control system 100 include errors detected during power-up check, errors detected during insertion of the expandable member 110, and errors detected during runtime (e.g., during therapeutic use).

Power-Up Check

In some variations, one or more controllers (e.g., system controller 106 in FIG. 1) may execute power-up check tests when the blood flow control system 100 is first turned on by the user. For example, when the blood flow control system 100 is turned on for the first time, the system controller 106 may automatically initiate one or more power-up check tests. The power-up check tests may include a variety of checks on the blood flow control system 100, such as, for example, determining if there has been damage or degradation to the blood flow control system 100 during shipment. In some variations, the sensor(s) (e.g., proximal sensor, distal sensor, expandable member sensor, etc.) may transmit sensor data to the system controller 106. The system controller 106 may conduct the power-up checks using measurements such as proximal average pressure, distal average pressure, expandable member pressure, a combination thereof, and/or the like.

Sensor Damage

A power check-up test may include determining whether one or more sensors in the blood flow control system are damaged or non-functional. In some variations, the system controller 106 may receive one or more of proximal average pressure from the proximal sensor, distal average pressure from the distal sensor, ambient pressure from the barometer, and/or expandable member pressure from the expandable member sensor. Threshold values and/or threshold ranges may be assigned to the proximal average pressure, distal average pressure, ambient pressure, and/or expandable member pressure. For instance, a user may input threshold values and/or threshold ranges via a user interface. Alternatively, the system controller 106 may determine the threshold values and/or threshold ranges and subsequently assign them to respective measurements. The system controller 106 may compare one or more measurements with their respective threshold values and/or threshold ranges. For example, the system controller may compare the proximal average pressure to a threshold proximal average pressure, the distal average pressure to a threshold distal average pressure, the ambient pressure to a threshold ambient pressure, and the expandable member pressure to a threshold expandable member pressure. Alternatively, the system controller 106 may compare a combination of one or more of the measurements to a combined threshold range. For example, the system controller 106 may compare a function of distal average pressure and proximal average pressure to a combined threshold value and/or threshold range. If the measurements fall outside their respective threshold value and/or threshold range, the system controller 106 may identify an error indicative of sensor damage. In response to detecting this error, the system controller 106 may inhibit the functioning of the blood flow control system 100 by, for example, shutting down the system.

Figure 3:
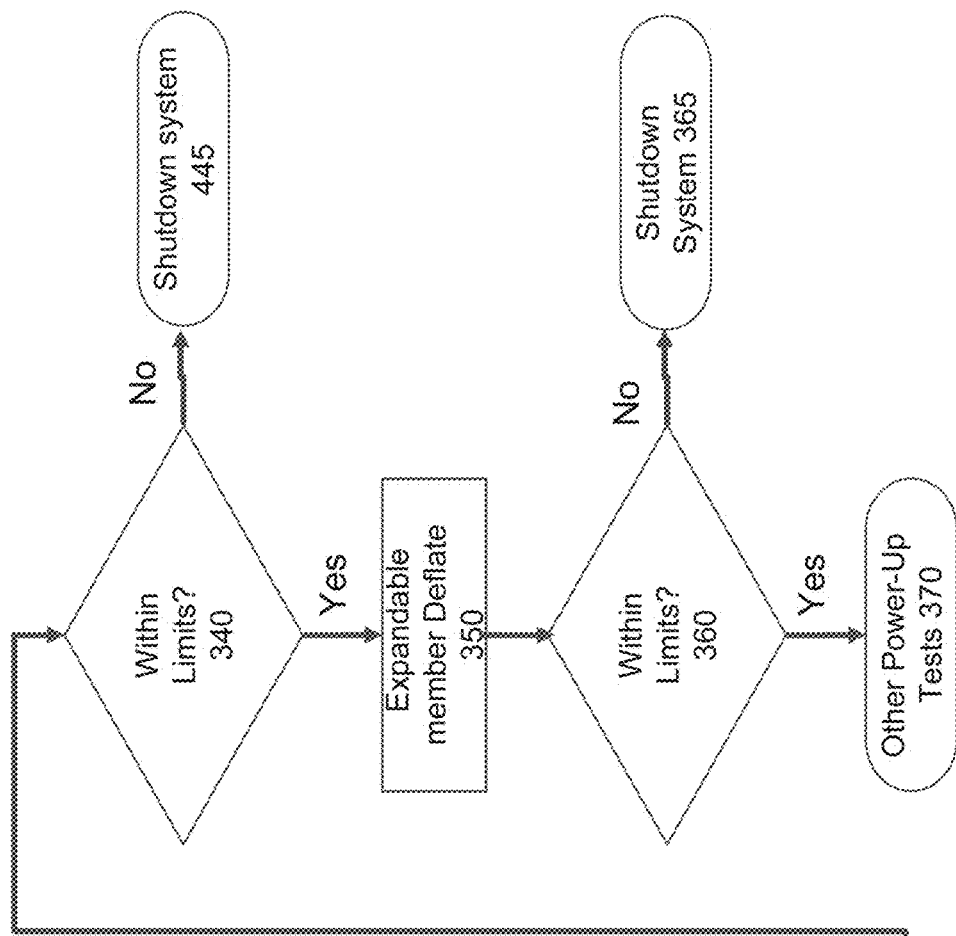
FIG. 3 is an exemplary variation of a flow diagram for various power-up check tests when a user turns the power on to the blood flow control system for the first time.
Figure 3:
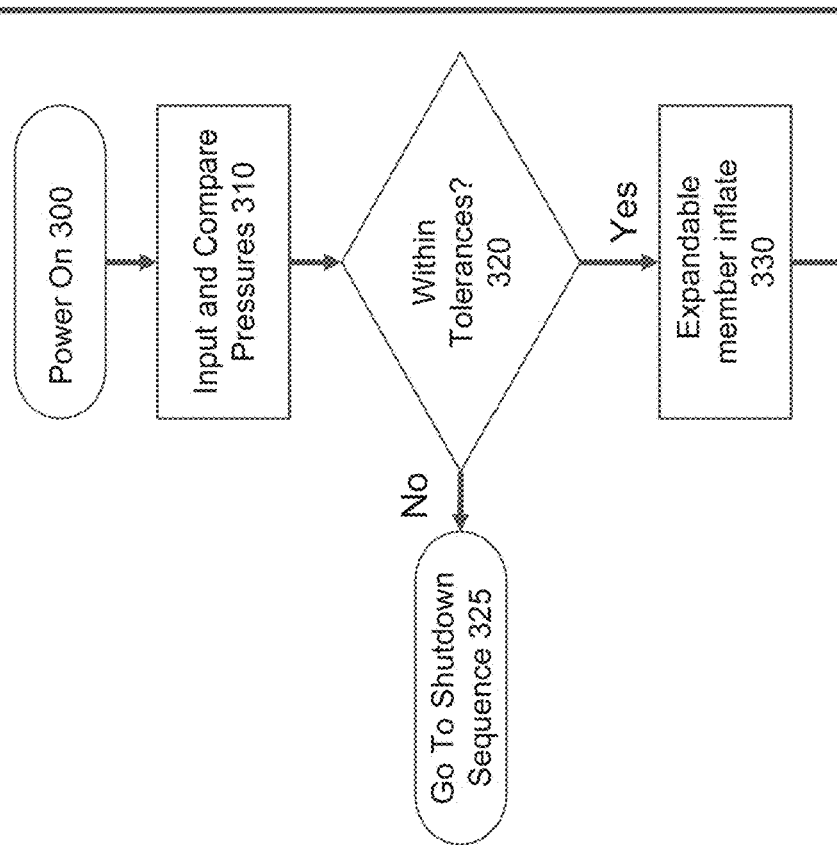

FIG. 3 is an exemplary variation of a flow diagram for various power-up check tests, including a test to determine sensor damage, when a user turns the blood flow control system 100 power on for the first time. At 300, the blood flow control system 100 may be turned on for the first time. In some variations, at 310, during a power-up check test, the system controller 106 may compare proximal average pressure, distal average pressure, expandable member pressure, and/or data from one or more barometers with target values or target ranges. At 320, the system controller 106 may identify if the PMAP, DMAP, expandable member pressure, and/or data from the barometer are at or near target values, and/or fall within their respective target ranges. If the PMAP, DMAP, expandable member pressure, and/or data from the barometer are not at or near the target values and/or within the target ranges, this may indicate that one or more of the sensors may be damaged, (e.g., may have been damaged during shipment).

For example, prior to inserting the elongate body 102 into a patient's body, the PMAP, DMAP, and the data from the barometer may be approximately the same. The value of PMAP, DMAP, and/or pressure from the barometer at power-up may be considered as the "zero-offset." When inserted into the body, the blood pressure of the patient (e.g., data from proximal sensor and distal sensor) may be the arithmetic difference of the value and the "zero-offset."

In some variations, during power-up, if one of PMAP, DMAP, and/or barometer value may differ from each other, then it may indicate that one or more sensors may be damaged. In some variations, if the measurements from the sensor data show a short (e.g., voltage is zero), or an open (e.g., voltage is maximum), this may indicate that one or more sensors may be damaged. In response to detecting this error, at 325, the system controller 106 may inhibit the functioning of the blood flow control system 100 by, for example, shutting down the system.

Expandable Member Damage

In some variations, the power-up check test may further include checking the integrity of the expandable member. The system controller 106 may actuate the pump 108 to inject a small amount of fluid and/or compressed gas into the expandable member 110. The amount of fluid and/or compressed gas injected may be measured using a position sensor and/or using an encoder. In response to injecting the fluid and/or compressed gas into the expandable member, the system controller 106 may receive an expandable member pressure from the expandable member pressure sensor. The system controller may compare the expandable member pressure to an expected pressure. In some variations, if the pump 108 has not yet been attached to the blood flow control system 100, then the expected change in pressure may be zero. In some variations, if the pump 108 has been attached to the blood flow control system 100, but the stopcock has not been opened, the expected change in pressure may still be zero. In some variations, if the stopcock is opened, then the expected change in pressure may be for example, about 20 mmHg with a pump of 100 μL over 100 milliseconds. If the expandable member pressure does not match the expected pressure, the system controller 106 may identify an error indicative of damage to the expandable member. In response to detecting this error, the system controller 106 may inhibit the functioning of the blood flow control system 100 by, for example, shutting down the system.

For example, turning back to FIG. 3, at 330, the power-up check test may further include causing the pump 108 to inject a small amount of fluid and/or compressed gas into the expandable member 110. At 340, the system controller 106 may determine whether the expandable member pressure has changed an expected amount based on the amount of fluid and/or compressed gas injected into the expandable member 110. At step 340, if the expandable member pressure does not follow the expected levels, this indicates an error, and at step 345 the blood flow control system is shutdown.

For example, if after the stopcock valve is opened, the expandable member pressure sees a spike of less than 20 mmHg with an intended movement of 100 μL over 100 milliseconds. in the pump 108, this may indicate that the expandable member pressure is increasing at a lower rate than expected, which may be indicative of a leak in the expandable member.

At step 350, the power-up check test may include causing the pump 108 to remove a small amount of fluid and/or compressed gas from the expandable member 110. At 360, the system controller 106 may determine whether the expandable member pressure has changed an expected amount based on the amount of fluid and/or compressed gas removed from the expandable member 110. At step 360, if the expandable member pressure does not follow the expected levels, then the system controller 106 may detect an error indicating damage to the expandable member. As described above, if an expected spike in the expandable member pressure is not detected, this may be indicative of mechanical damage to the expandable member. In contrast, if the spike to the expandable member pressure is too high, it may be indicative of an obstruction in the fluid path and/or compressed gas path of the expandable member. If the spike to the expandable member is lower than the expected spike then it may be indicative of a leak in the fluid path and/or compressed gas path and/or the expandable member. At 365, the blood flow control system may shutdown.

Low Controller Battery

In some variations, other power-up check tests may include determining the estimated remaining battery-powered operating time. The system controller 106 may compare the battery voltage to a threshold value. If the voltage drops below a threshold value, the system controller 106 may transmit an alert to a user indicating the same via a user interface.

High Controller Temperature

In some variations, the power-up check tests may include determining whether the system controller's 106 internal temperature is greater than a predetermined threshold (e.g., 40 degrees centigrade). If the internal temperature is greater than the predetermined threshold, the system controller 106 may transmit an alert to the user indicating the same.

Audio Error

In some variations, the power-up check tests may include determining an audio error. For example, if the blood flow control system 100 is unable to emit or control audible signals, the blood flow control system 100 may transmit an alert to a user (e.g., via the user interface) notifying the user of the error.

While described above in a particular order, it should be appreciated that the power-up check tests may be performed in any order, need not be performed in the order described, and a system need not perform every power-up check test for every therapeutic procedure.

Runtime Check

In some variations, after completion of the power-up check tests, a user may be instructed, e.g., via a user interface, to insert the expandable member 110 into the patient's blood vessel (e.g., artery, aorta, etc.). At this point, system controller 106 may activate the runtime system checks.

Runtime checks may be implemented during the therapeutic procedure, and may be used during all or any portion thereof. For example, runtime checks may be utilized as the expandable member 110 is inserted into a patient's blood vessel. Additionally or alternatively, runtime checks may be utilized after the expandable member 110 is positioned at a desired location within the blood vessel and is being used to control blood flow in the blood vessel. In some variations, the sensor(s) (e.g., proximal sensor, distal sensor, expandable member sensor, etc.) may transmit sensor data to the system controller 106. The system controller 106 may conduct the runtime checks using any of the measurements described herein, such as, for example, proximal average pressure, distal average pressure, expandable member pressure, a combination thereof, and/or the like.

Communications Error

In some variations, the power-up check tests may include determining a communications error. In some variations, as soon as the device controller 112 is coupled to the systems controller 106, the systems controller may run the communications error check (for example, every 1 second). In some variations, sensor data may be received at the system controller 106 periodically (e.g., every couple of seconds such as every 1, 2, 3, 4, 5, 6, seconds or more, including all values and sub-ranges therein). In some variations, the system controller 106 may retrieve the measurements from the sensor data periodically (e.g., every couple of seconds and/or within a set time period). A failure to retrieve measurements in a periodic manner (e.g., within a set time period) may be indicative of communication issues between the system controller 106 and one or more sensors. Accordingly, the system controller 106 may detect a communications error if the system controller 106 cannot retrieve one or more measurements from sensor data periodically. In response to detecting this error, the controller may transmit an alert and/or an error message to a user. The user may have to detach the pump from the blood flow control system 100 and may have to manually inflate and/or deflate the expandable member.

In one example, a failure to retrieve current DMAP or current PMAP for a maximum period of 3 seconds may trigger the error. In response, the system controller 106 may inhibit automatic inflation and/or deflation of the expandable member. The user may have to manually inflate and/or deflate the expandable member. In another example, a failure to retrieve expandable member pressure for a maximum period of 1 second may cause the system controller 106 to inhibit automatic control of the expandable member such that the user may have to manually inflate and/or deflate the expandable member.

Insertion Sequence Error

In use, the expandable member 110 of a blood flow control device described herein may be advanced through the patient's vasculature and inserted into a target blood vessel. The expandable member 110 may be positioned at a desired location within the blood vessel to provide therapeutic intervention. At times, despite the user's intention to insert the expandable member 110 into a particular blood vessel, the user may inadvertently insert the expandable member 110 into a different location. Accordingly, the blood flow control systems described here may include an insertion sequence error that may be detected upon insertion of the expandable member 110.

In response to positioning the expandable member at a desired location, the system controller 106 may receive sensor data from one or more sensors. For instance, the system controller 106 may receive proximal average pressure, distal average pressure and/or barometer data. In some variations, the system controller 106 may combine the proximal average pressure, distal average pressure, and barometer data to generate an insertion signature. In other variations, the system controller 106 may combine just the proximal average pressure and the distal average pressure to generate an insertion signature. The system controller 106 may then compare the generated insertion signature to an expected insertion signature based on the desired location for therapeutic intervention (e.g., arterial vessel, aorta). In some variations, the expected insertion signature may be a threshold value that combines one or more of an expected proximal average pressure, an expected distal average pressure, and an expected barometer reading. If the insertion signatures do not match or if the generated insertion signature is not within a threshold range, the system controller 106 may detect an insertion sequence error. In some variations, if the expandable member is not in the right location, the generated insertion signature may not be current, and the system controller 106 may detect an insertion sequence error. In response to detecting this error, the system controller 106 may inhibit a function of the blood flow control system. For example, the system controller 106 may shutdown the system 100, or may place the system in manual mode and prevent the system from entering the automatic mode. Put another way, the system controller 106 may allow the system to enter manual mode, but may prevent or inhibit the system from entering automatic mode. In some variations, the system controller 106 may inhibit the system from entering automatic mode until user confirmation of proper placement is received.

For example, generally, when the expandable member 110 is inserted into a blood vessel, the proximal average pressure may increase and the distal average pressure may decrease. In some variations, these changes in the physiologic conditions may be seen after initial inflation of the expandable member. For example, an increase in the proximal average pressure and a decrease in the distal average pressure may be seen just or shortly after initial inflation following insertion of the expandable member 110. However, the barometer may show little or no change to the ambient pressure. The increase to proximal average pressure and decrease in distal average pressure in combination with no change to barometer readings may indicate an insertion signature. In some variations, pulsatile waveforms on the proximal average pressure and the distal average pressure may indicate an insertion signature. In some variations, if the distal MAP is slightly higher than proximal MAP, it may be indicative of insertion of the expandable member in an incorrect location. In some variations, if distal pulsatility is slightly higher than proximal pulsatility, it may be indicative of insertion of the expandable member in an incorrect location. It should be noted again here that proximal may be tip end of the elongate body 102 and distal may be the expandable member end of the elongate body in these examples.

Figure 4:
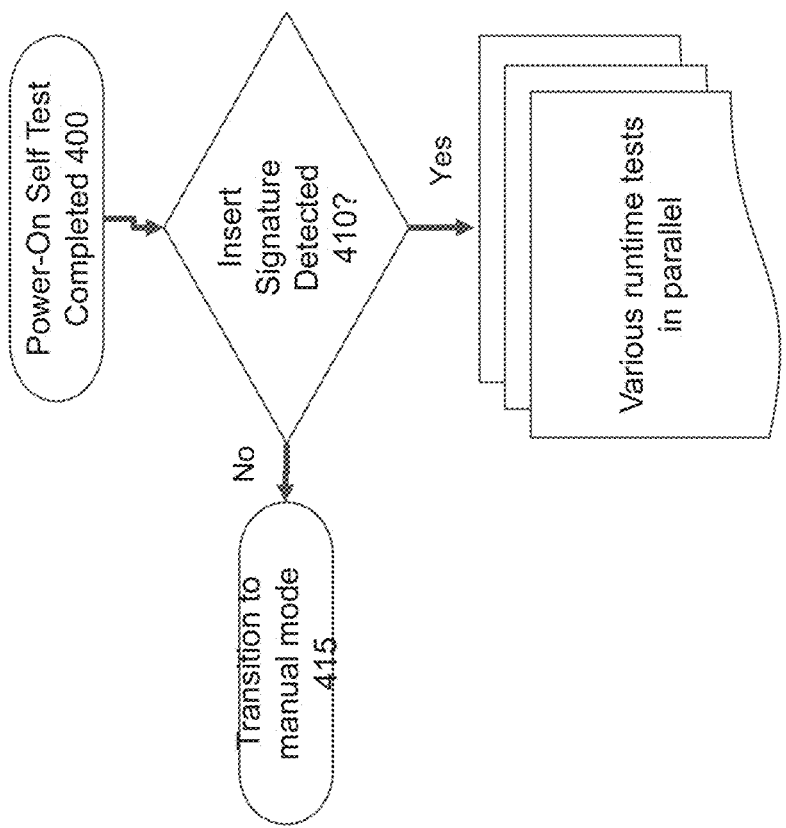
FIG. 4 is a flow diagram of an exemplary variation of a runtime check test.

FIG. 4 is a flow diagram of an exemplary variation of a runtime check test for insertion sequence error. At 410, the system controller 106 may check for an insertion signature. As discussed above, the insertion signature may be one or more of, or a combination of, proximal average pressure, and/or distal average pressure. If at 410, the insertion signature does not match an expected insertion signature, the system controller 106 may detect an insertion signature error at 415. For instance, if in response to inserting the expandable member 110 into a blood vessel, the proximal average pressure and distal average pressure do not increase, the system controller 106 may detect the insertion sequence error.

As another example, the insertion signature may be based on combination of PMAP and DMAP. In this example, the system controller 106 may receive PMAP and DMAP, calculate a difference between the received DMAP and a threshold DMAP value (e.g., 1 mmHg) and compare the difference to the received PMAP. If the system controller 106 determines that the received PMAP is less than the difference of the received DMAP and the threshold DMAP value, the system controller 106 may detect the insertion sequence error. In response to the error, at 415, the system controller 106 may automatically transition from an automatic mode to a manual mode (as discussed above).

Dampening Error

In some variations, runtime check tests may include detecting dampening in a first sensor in the system (e.g., one of the proximal sensor and the distal sensor) but not in another sensor in the system (e.g., the other of the proximal sensor and the distal sensor), which may indicate incorrect sensor measurements.

In one example, the system controller 106 may receive sensor measurements from the proximal sensor, such as, for example, proximal systolic pressure, proximal diastolic pressure, and/or PMAP. The system controller 106 may analyze the waveforms of the proximal average pressures. Similarly, the system controller 106 may receive measurements from the distal sensor, such as, for example, distal systolic pressure, distal diastolic pressure, and/or DMAP). The system controller 106 may analyze the waveforms of the distal average pressure. The system controller 106 may compare the waveforms of the proximal average pressure and the distal average pressure. If the waveforms are dissimilar, if multiple notches or waveform sub-features are detected on one waveform but not on the other, the system controller 106 may detect dampening in one of the sensors (e.g., the proximal sensor or the distal sensor), but not in the other of the sensors (e.g., the other of the proximal sensor and the distal sensor).

In response to detecting a dampening error, the system controller 106 may inhibit a function of the system. For example, in response to detecting the dampening error, the system controller 106 may automatically transition the system from the automatic mode to the manual mode.

FIG. 5A is a flow diagram of an exemplary variation of a runtime check test to detect a dampening error. In FIG. 5A, the pulsatility of the proximal average pressure and the distal average pressure may be compared. An error may be reported if dampening is detected in one sensor but not in the other. At step 524, if the dampening is detected, then the system controller may automatically transition from an automatic mode to a manual mode.

Clotting Error

In some variations, the runtime check test may include detecting clotting in the blood vessel. The system controller 106 may receive proximal systolic pressure, proximal diastolic pressure, and PMAP from the proximal sensor and may determine proximal average Pulsatility based on these measurements. Similarly, the system controller 106 may receive distal systolic pressure, distal diastolic pressure, and DMAP from the distal sensor and may determine distal average Pulsatility based on these measurements. The system controller 106 may also receive expandable member pressure from the expandable member pressure sensor and may determine the expandable member pressure Pulsatility. In some variations, the system controller 106 may compare the proximal average Pulsatility and the distal average Pulsatility to the expandable member pressure Pulsatility. If the trend of the proximal average pulsatility and/or the distal average pulsatility does not match the trend of the expandable member pressure Pulsatility, then the system controller

106 may detect an error indicating clotting in the blood vessel. For example, if the proximal average pulsatility and/or the distal average pulsatility drops but the expandable member pressure Pulsatility does not drop, it may be indicative of clotting in the blood vessel. In response, the system controller 106 may automatically transition from an automatic mode to a manual mode.

FIG. 5B is a flow diagram of an exemplary variation of a runtime check test to test clotting. In FIG. 5B, the pulsatility of the proximal average and the distal average may be compared with the pulsatility of the expandable member pressure. If the proximal systolic pressure pulsatility drops but the expandable pulsatility does not drop, this may indicate clotting. At 532, if the condition is not detected, then at 534 the system may automatically transition from an automatic mode to a manual mode.

Noise Due to Electrical Interference

In some variations, the runtime check test may include detecting noise due to electrical interference. If there is excessive electrical interference, such as electrical noise caused by an electro-cautery device, the system controller 106 may not receive appropriate sensor measurements, such as, for example, the proximal average pressure and the distal average pressure. In some variations, the system controller 106 may receive measurements from the sensors, but the measurements may be incorrect which may prevent the system controller 106 from determining other blood pressure values from the measurements. For example, upon receiving sensor data from the proximal sensor and the distal sensor, the system controller 106 may not be able to determine the proximal average pressure and the distal average pressure because the sensor measurements may be excessively high. The inability to determine the proximal average pressure and the distal average pressure may indicate an error due to electrical noise owing to electrical interference. In response, the system controller 106 may inhibit a function of the blood flow control system. For example, the system controller 106 may automatically transition the system from the automatic mode to the manual mode.

Figure 5D:
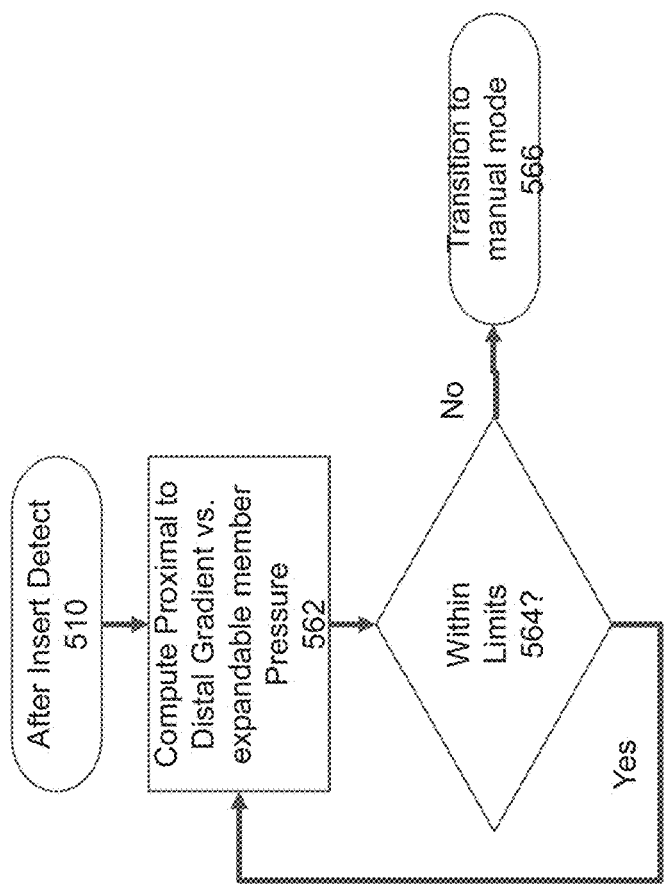
Figure 5C:
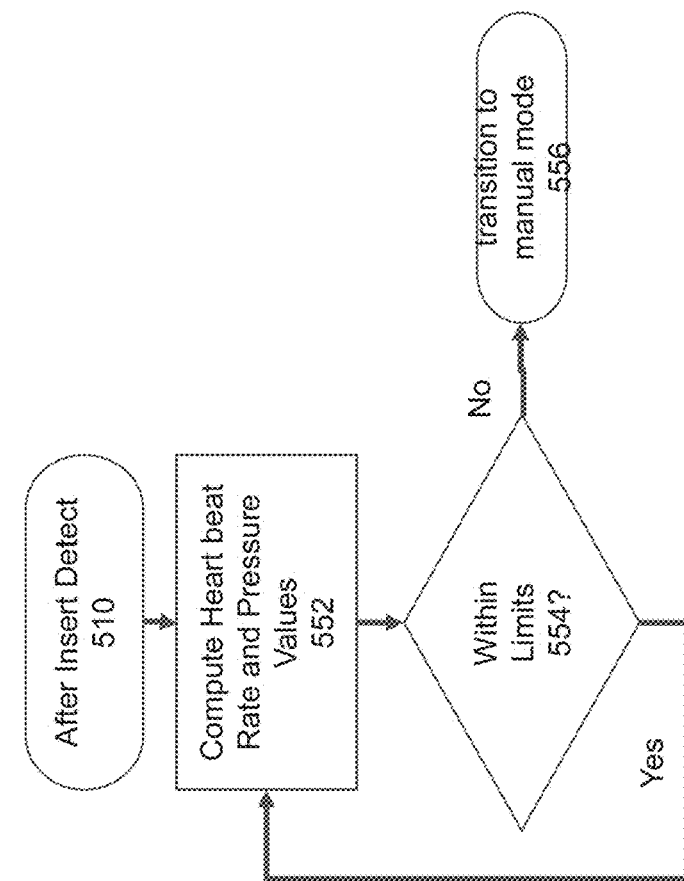

FIG. 5C is a flow diagram of an exemplary variation of a runtime check test to detect noise due to electrical interference. In FIG. 5C, step 552 involves detection of excess electrical noise, such as caused by an electro-cautery device, which may result in a temporary inability for the system controller 106 to determine proximal average pressure and distal average pressure. At step 554, if the condition is detected, the system controller 106 may detect an error. As a result of the error detection, the system controller 106 may automatically transition the system from the automatic mode to the manual mode. Additionally or alternatively, the system controller 106 may transmit an indication or alert to the user interface noting the error and/or that valid blood pressure measurements may not be displayed on the user interface.

In some variations, the detection of excess noise relies on the minimum and maximum valid pressures associated with human physiology to be well within the minimum and maximum pressures reportable by the proximal sensor and distal sensor. For example, if a pressure of 500 mmHg (well above the maximum plausible 300 mmHg) or −300 mmHg (well below the minimum plausible −50 mmHg) are observed, then the system controller 106 may detect excess electrical noise. The maximum plausible human heartbeat rate is approximately 5 Hz (300 beats per minute). Therefore, oscillations in the proximal average pressure and/or distal average pressure at a rate significantly greater than 5 Hz may also cause the system controller 106 to detect excess electrical noise. In response, the system controller 106 may automatically transition the system from the automatic mode to the manual mode. Additionally, the system controller 106 may also inhibit display of blood pressure measurements on the user interface. If the excess electrical noise condition ends within a predefined time period, then this error may be considered temporary. If the error is considered temporary, the system controller 106 may re-enable display of the pressure data on the user interface and may cease to inhibit the automatic inflation/deflation of expandable member (e.g., transition back to automatic mode) after the predefined time period ends. For instance, if the excess electrical noise ceases after ten seconds, the error may be considered temporary. However, if the excess electrical noise exceeds 1 minute, the error may be considered permanent, and the system controller 106 may automatically transition the system from the automatic mode to the manual mode.

Pressure Gradient Error

In some variations, the runtime check test may include detecting a pressure gradient error. The system controller 106 may receive proximal systolic pressure, proximal diastolic pressure, and PMAP from the proximal sensor and may determine proximal average pulsatility based on these measurements. Similarly, the system controller 106 may receive distal systolic pressure, distal diastolic pressure, and DMAP from the distal sensor and may determine distal average pulsatility based on these measurements. The system controller 106 may also measure the difference between PMAP and DMAP. This difference may indicate a pressure gradient. In some variations, for various values of pressure gradients, the system controller 106 may be able to predict a respective distal average pulsatility. Similarly, for various distal average pulsatility, the system controller 106 may be able to predict a respective pressure gradient. For any given expandable member pressure, there may be a valid range of pressure gradients and distal average pulsatilities. If the system controller 106 detects a value that may be outside the valid range of pressure gradients and distal average pulsatilities, the system controller 106 may detect a pressure gradient error. In response to this error, the system controller 106 may inhibit a function of the blood flow control system. For example, the system controller 106 may automatically transition the system from the automatic mode to the manual mode and/or may provide a warning (e.g., an alert) to the user via the user interface. In a non-limiting example, if the DMAP is 10 mmHg lower than the PMAP, the distal pulsatility should be within 90% of the proximal pulsatility. If the system controller 106 detects a value outside the distal pulsatility and proximal pulsatility, the system controller 106 may detect a pressure gradient error.

FIG. 5D is a flow diagram of an exemplary variation of a runtime check test to detect pressure gradient error. In FIG. 5D, the sequence starting at Step 560 involves cases where the pressure gradient is not at expected levels. When the distal pulsatility is much lower than the proximal pulsatility, the difference between PMAP and DMAP may be predicted. Similarly, when the gradient is measured, a predicted pulsatility of the distal average pressure is known. This can also be correlated relative to the expandable member pressure: at higher pressures the pressure gradient and the distal pulsatility can all be predicted. For any given expandable member pressure, there should be a valid range of gradients and distal pulsatilities. If the values are outside those limits, then the system controller 106 may automatically transition from an automatic mode to a manual mode and/or provide a warning (e.g., an alert) to the user via the User Interface.

One Sensor Reading is Too High or Too Low

In some variations, the runtime check test may include identifying that one of the sensor measurements (e.g., measurements from proximal or distal sensor) may be too high or too low relative to measurements from another sensor (the other of the proximal sensor and distal sensor). For example, the system controller 106 may receive current PMAP from the proximal sensor and current DMAP from the distal sensor, and may compare the current PMAP to the current DMAP. If the current PMAP drops below the current DMAP, the system controller 106 may detect an error indicating that one of the sensor readings may be too high or too low. In response, the system controller 106 may inhibit a function of the blood for control system and/or may provide a warning (e.g., an alert) to the user via the user interface. For example, the system controller 106 may automatically transition the system from the automatic mode to the manual mode. In some variations, this error may also occur if the proximal sensor and/or the distal sensor are damaged.

Figure 5F:
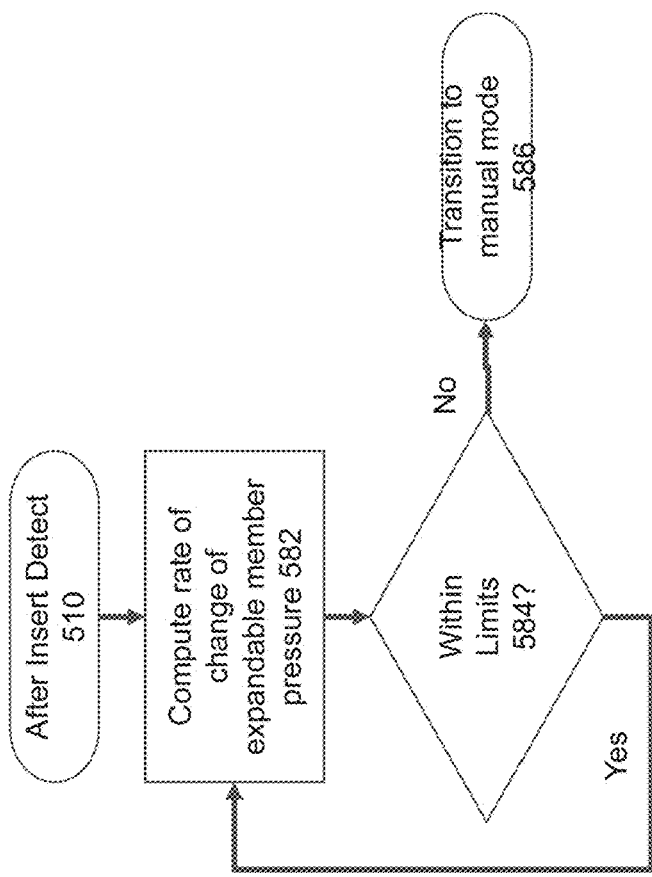
Figure 5E:
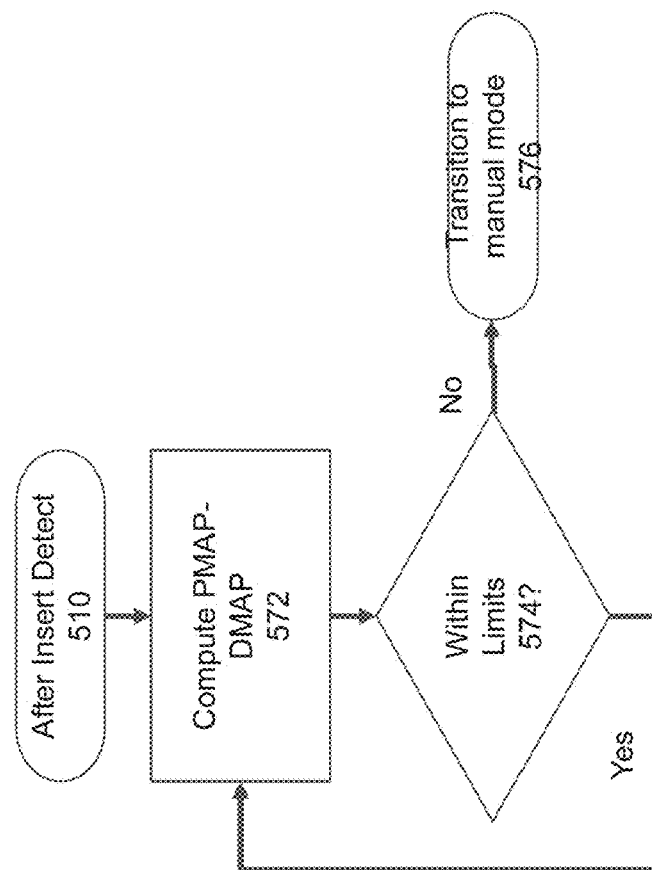

FIG. 5E is a flow diagram of an exemplary variation of a runtime check test for detecting whether one of the sensor's (e.g., proximal sensor or distal sensor) measurements are too high or too low. In FIG. 5E, the current PMAP 140 drops below the current DMAP. This may generally be indicative of an error associated with one of the sensors reporting a number that is too high or too low. The system controller 106 may automatically transition from an automatic mode to a manual mode and/or provide a warning (e.g., an alert) to the user via the User Interface.

Expandable Member Pressure and Pump Movement do not Correspond

In some variations, the runtime check test may include a test to identify whether the expandable member pressure corresponds to the pump 108 movement. For example, the system controller 106 may receive the expandable member pressure from an expandable member pressure sensor. The position sensor and/or the motion sensor (e.g., encoder) may make note of pump movements. If the system controller 108 identifies an increase or decrease in the expandable member pressure without an associated movement of the pump or with an unexpected pump movement, then the system controller 108 may detect an error. Similarly, the system controller 108 may predict hemodynamics within the blood vessel for various movements of the pump 108. If the rate of change of hemodynamics for a specific movement of the pump is outside the predicted rate of change of hemodynamics, the system controller 108 may detect an error. In response, the system controller 106 may inhibit a function of the blood flow control system and/or may provide a warning (e.g., an alert) to the user via the user interface. In some variations, the system controller 106 may automatically transition the system from the automatic mode to the manual mode.

FIG. 5F is a flow diagram of an exemplary variation of a runtime check test to identify whether the expandable member pressure corresponds to the pump movement. In FIG. 5F, the system controller 106 may check for a short term increase or decrease in the expandable member pressure without an associated movement of the Pump 108. While the heart and vascular system will exhibit changes in the pressures over various time windows, the beat-to-beat changes in the hemodynamics are tracked, known, and predicted. Therefore, when rates of change that are outside the known and predicted rates of change are detected, and there has been no associated movement (or an unexpected movement) in the Pump 108, then the system controller 106 may automatically transition from an automatic mode to a manual mode and/or may provide a warning (e.g., an alert) to the user via the user interface.

Sensor Damage

In some variations, the runtime check tests may include a test to identify whether one or more of the sensors is damaged. For example, the system controller 106 may receive data from one or more sensors (e.g., proximal sensor, distal sensor, expandable member pressure sensor, etc.) and may compare the current data from the sensor to data previously received from the sensor. The system controller 106 may determine if an absolute change and/or a rate of change between the current and previous sensor data exceeds a target threshold or falls outside a predetermined target range, and if so, the system controller 106 may detect a sensor damage error. If a sensor damage error is detected, the system controller 106 may inhibit a function of the blood flow control system and/or may provide a warning (e.g., an alert) the user via the user interface. For example, in some variations, the system controller 106 may shutdown the blood flow control system.

Figures 5G, 5H:
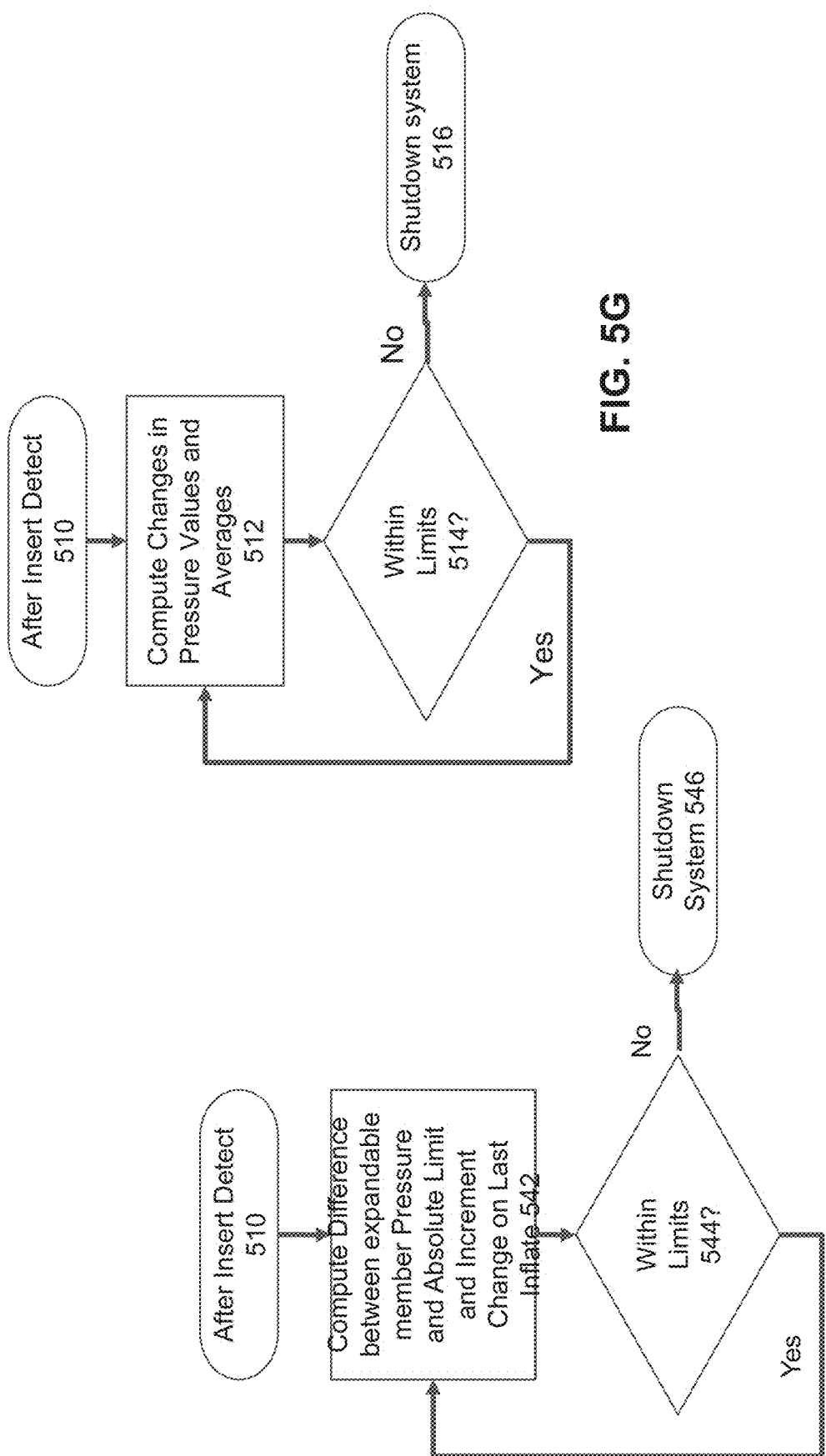

FIG. 5G is a flow diagram of an exemplary variation of a runtime check test to detect sensor damage in the blood flow control system. At 512, the system controller 106 may receive proximal average pressure from the proximal sensor and distal average pressure from the distal sensor. The proximal average pressure and the distal average pressure may be compared against previous values of proximal average pressure and distal average pressure. At 514, if the change in value or change in rate is greater than a threshold, then the system controller may identify an error indicating sensor damage. In response, the system controller 106 may shutdown the blood flow control system. For example, if either proximal or distal MAP are lower than barometric pressure, then it may be indicative of sensor damage. In some variations, if either proximal or distal MAP go beyond physiologic limits (e.g., above 300 mmHg), that may also be indicative of sensor damage error. If the distal sensor has pulsatility and the proximal sensor does not, that may be indicative of damage to the proximal sensor. If proximal sensor has pulsatility, the distal sensor does not, and the expandable member pressure is below a threshold, this may be indicative of damage to distal sensor. In response, the system controller 106 may inhibit a function of the blood flow control system, by e.g., shutting down the blood flow control system.

Maximum Inflation

In some variations, the runtime check tests may include a test to identify whether the expandable member has reached a maximum inflation level. In some variations, at the beginning of a procedure, such as, after advancing the expandable member to a target location within a patient (e.g., an aorta), a user may not yet have coupled the blood flow control device and/or the pump to the system controller 106 and may manually inflate the expandable member using the pump (e.g., syringe) to full occlusion (such as blood flow state of Occlusion) without utilizing the system controller 106. The user may also decouple the pump from the system controller 106 (if previously coupled) before manual inflation.

When the pump is coupled (or recoupled) to the system controller 106, the system controller 106 may register this initial inflation level as the maximum allowable inflation level for the particular patient and/or the particular procedure. For example, the system controller 106 may record the position of the pump (e.g., using position sensor and/or motion sensor) when the pump is coupled to the controller after initial inflation and may correlate this position to a maximum allowable inflation level for the blood flow control system. During subsequent automatic operation, if the movement and/or position of the pump indicates an inflation level nearing or exceeding the maximum allowable inflation level, the system controller may inhibit a function of the blood flow control system. For example the system controller 106 may transition the blood flow control device from the automatic mode to the manual mode of operation. In another example, the system controller may inhibit further automatic inflation of the expandable member. Additionally or alternatively, the system controller 106 may simultaneously or substantially simultaneously transmit an alert to the user indicating an error related to maximum allowable inflation level.

FIG. 5G is a flow diagram of an exemplary variation of a runtime check test to detect maximum inflation in the expandable member. In some variations, the system controller may receive the expandable member pressure from the expandable member pressure sensor. The system controller 106 may then compare the measured expandable member pressure to a maximum allowed pressure value (Step 540). If the measured expandable member pressure exceeds the maximum allowed pressure value, or falls outside a predetermined maximum allowed pressure range, the system controller 106 may detect a maximum inflation error and may inhibit a function of the blood flow control system and/or provide a warning (e.g., an alert) to a user via the user interface. In some variations, upon detection of this error, the system controller 106 may inhibit automatic inflation of the expandable member. However, the system controller 106 may not inhibit manual deflation of the expandable member.

In other variations, the maximum inflation level may be determined based on data received from one or more sensors (e.g., expandable member pressure sensor, position sensor, etc.) and may be based on expandable member pressure, expandable member volume, and/or rate of change of the expandable member pressure based on one or more incremental inflation amounts. For example, near its maximum allowed pressure, the expandable member may experience a much larger change in internal pressure for a given unit of added fluid and/or compressed gas. For example, when the expandable member 110 is only partially inflated and may not be making full contact with the blood vessel wall, an increase of 100 microliters in the expandable member volume may result in only a 5 mmHg increase in the expandable member pressure. However, when the expandable member 110 is almost fully inflated and is making full contact with the blood vessel wall, an increase of 100 microliters in the expandable member volume may result in about 10 or about 15 mmHg increase in the expandable pressure. The maximum allowed inflation may be determined based on a combination of expandable member pressure, expandable member volume and/or rate of change of the expandable member pressure based on the last inflation amount (e.g., as indicated by the position sensor). At step 542, if the inflation exceeds a maximum allowed inflation value, a maximum inflation error may be detected and the system controller 106 may inhibit a function of the blood flow control system and/or may provide a warning (e.g., an alert) the a user via the user interface. For example, in some variations, the system controller 106 may inhibit automatic inflation of the expandable member.

Morphological Changes to Expandable Member

Figure 5I:
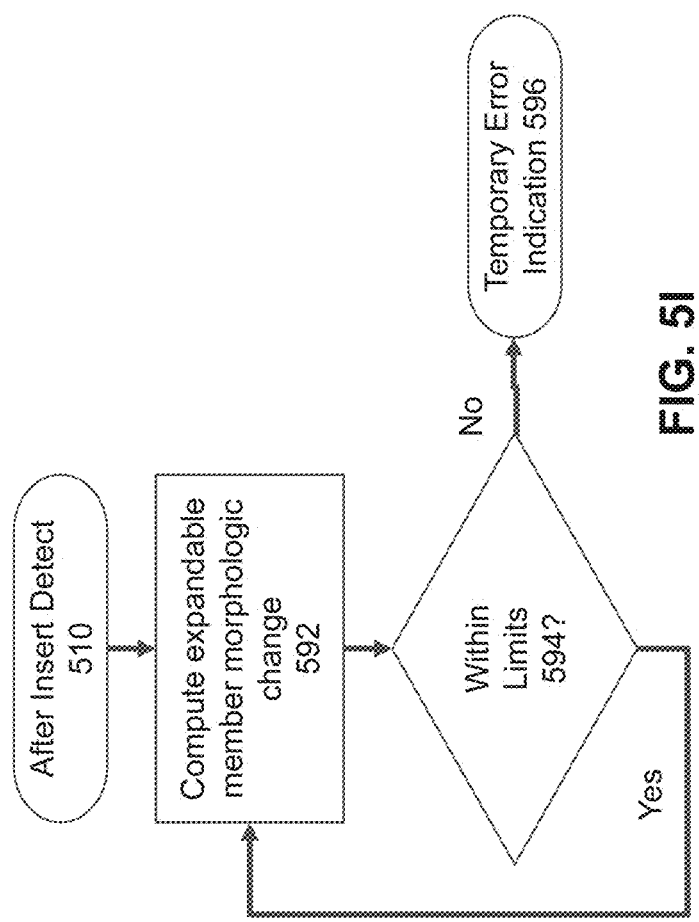

In some variations, the runtime check tests may include a test to check for morphological changes in the expandable member 110. For example, the system controller 106 may check for morphological changes in the expandable member 110 when the expandable member is inflated and/or deflated. FIG. 5I is a flow diagram of an exemplary variation of a runtime check to detect morphological changes in an expandable member. In some variations, the system controller 106 may associate the rate of change of expandable member pressure, proximal average pressure, and/or distal average pressure with a level of predicted occlusion. If the measured level of occlusion is different from the predicted level of occlusion, system controller 106 may detect a morphological change to expandable member error. In response, the system controller 106 may transmit an alert to the user indicating the same.

For example, in FIG. 5I, the system controller 106 checks for morphological changes in the expandable member 110. The morphological change phenomenon may occur when the expandable member 110 is partially inflated, such as levels between 40-80% of the Occlusion blood flow state. The pulsatile nature of the blood flow and the non-rigid nature of the wall material of the expandable member 110 may causes the expandable member material to "flap" in the flow. This flapping includes oscillatory convex and/or concave bending of the wall material.

The "flapping" may have some phase delay from the pressure wave, and may include one or more reverberations. This phenomenon is detected via observation of secondary oscillations at approximately the same rate as the heartbeat rate within the expandable member pressure or in the proximal average pressure and/or the distal average pressure. Upon detection, the system controller 106 may provide an indication to the user, e.g., via the user interface.

It should be appreciated that the runtime checks described herein, including, for example, the runtime checks in FIGS. 5A-5I, may run in parallel. Table 1 below provides examples of various errors discussed herein, exemplary input measurements to identify the errors, and exemplary responses from the blood flow control system 100.

TABLE 1

| Types of Error | Type of check to detect error | Input | Comparison | Output |
| --- | --- | --- | --- | --- |
| Sensor damaged during shipment | Power-up check | Proximal average, distal average, balloon pressure, and measurement from barometer | Compares all four pressures to expected ranges within allowed tolerance | Shutdown indication is activated |

TABLE 1-continued

| Types of Error | Type of check to detect error | Input | Comparison | Output |
|---|---|---|---|---|
| Balloon damage | Power-up check and/or Runtime check | Absolute Balloon pressure value | Compare expected change to balloon pressure for change in volume of saline | Transmit alert to the user to determine if stopcock valve is open. If stopcock valve is open, then shutdown automatic control of the pump |
| Communications Error | Runtime check | DMAP, PMAP, Balloon pressure | Failure to retrieve DMAP or PMAP for a maximum period of 3 seconds, or failure to retrieve balloon pressure for a maximum period of one second | Shutdown system allowing a user to "manually" inflate and/or deflate. |
| Insertion sequence | During Insertion check | PMAP and DMAP | Combination of proximal sensor, distal sensor, and barometer values gives an insertion signature. ( | Shutdown the system |
| Sensor not working | Runtime check | Absolute pressure values, balloon volume, blood flow, barometer | Compare pressure values to expected pressure values | Shuts down the system |
| Dampening detected in one sensor but not the other | Runtime check | Proximal pressure average, distal pressure average | Compare (pulse pressure) pulsatility of proximal pressure average to distal pressure average | Automatic transition from automatic mode to manual mode |
| Clotting (you see dampening in pulse pressure) errors with proximal sensor (can also happen in the distal) | Runtime check | proximal systolic value and diastolic value, MAP values | Compares pulsatility of the Proximal Systolic and Diastolic values to pulsatility of balloon pressure | Automatic transition from automatic mode to manual mode |
| Excess electrical noise caused by an electro-cautery device | Runtime check | Proximal and distal blood pressure | Compare PMAP and DMAP to respective target ranges Compare heartbeat rate to a target range Compare proximal pulsitility and distal pulsitility to target ranges. | Automatic transition to manual mode, and provide indication no pressures can be displayed - if error ends within a threshold time - transition back to automatic mode |
| Pressure gradient is not at expected level - pressure gradient of PMAP and DMAP (difference between proximal and distal is not at the level) | Runtime check | Proximal Mean Arterial Pressure and Distal Mean Arterial Pressure | Compare predicted distal pulsatility to distal pulsatility | Automatic transition to manual mode and provide warning to user |
| One sensor is reporting too high or too low | Runtime check | Proximal Mean Arterial Pressure and Distal Mean Arterial Pressure | If Proximal MAP falls below Distal MAP | Automatic transition to manual mode and provide warning to user |
| Increase or decrease of balloon pressure without intended movement of pump | Runtime check | Balloon pressure and magnetic encoder | If there is no movement in pump, compare rate of change of hemodynamics to expected rate | Automatic transition to manual mode |

TABLE 1-continued

| Types of Error | Type of check to detect error | Input | Comparison | Output |
|---|---|---|---|---|
| Sensor Damage | Runtime check | Proximal average and distal average | Compare pressure values to expected values | Shutdown system |
| Maximum allowed pressure in balloon | Runtime check | Balloon pressure, total volume in balloon, rate of change in balloon pressure on last inflation | Compares balloon pressure and volume change at complete occlusion to maximum allowed balloon pressure and volume change | Shutdown system |
| Check for morphological changes in balloon | Runtime check | Blood flow state rate | Observe oscillations of pressure wave | Indication to a user |

Physiologic Checks

In some variations, when the blood flow control system is in use (i.e., during treatment), the blood flow control system may automatically conduct various physiologic checks to aid with the treatment. For instance, these physiologic checks may help the user monitor patient physiology. Additionally, in some variations, when the user defines target values and/or target ranges for detecting various errors, it may be possible that these target values and/or target ranges may be unachievable. Accordingly, the physiologic checks below may help a user rectify the target values and/or target ranges in order to ensure smooth functioning of the blood flow control system. FIGS. 6A through 6E illustrate flow diagrams for detecting exemplary temporary physiologic conditions using the blood flow control system 100.

Error in Target Value (e.g., DMAP)

In some variations, a target value and/or target range for the blood flow control system may be unachievable (e.g., because the value is too high, because the value is too low, because the value doesn't comport with physiologic changes the patient is experiencing (e.g., the patient is experiencing bleeding). In such variations, the system controller 106 may detect that the target may be unachievable and may alert the user accordingly. In some variations, the system controller 106 may additionally or alternatively instruct, e.g., via the user interface, the user to define a new target value and/or range. For example, in some variations, the user may set a target value and/or target range for a blood pressure measurement (e.g., target DMAP) via, for example, the user interface. However, it is possible that the user defined target may be unachievable In such variations, the system controller 106 may detect that the user-entered target may be unachievable and may alert the user and/or instruct the user to define a new target.

Figure 6A:
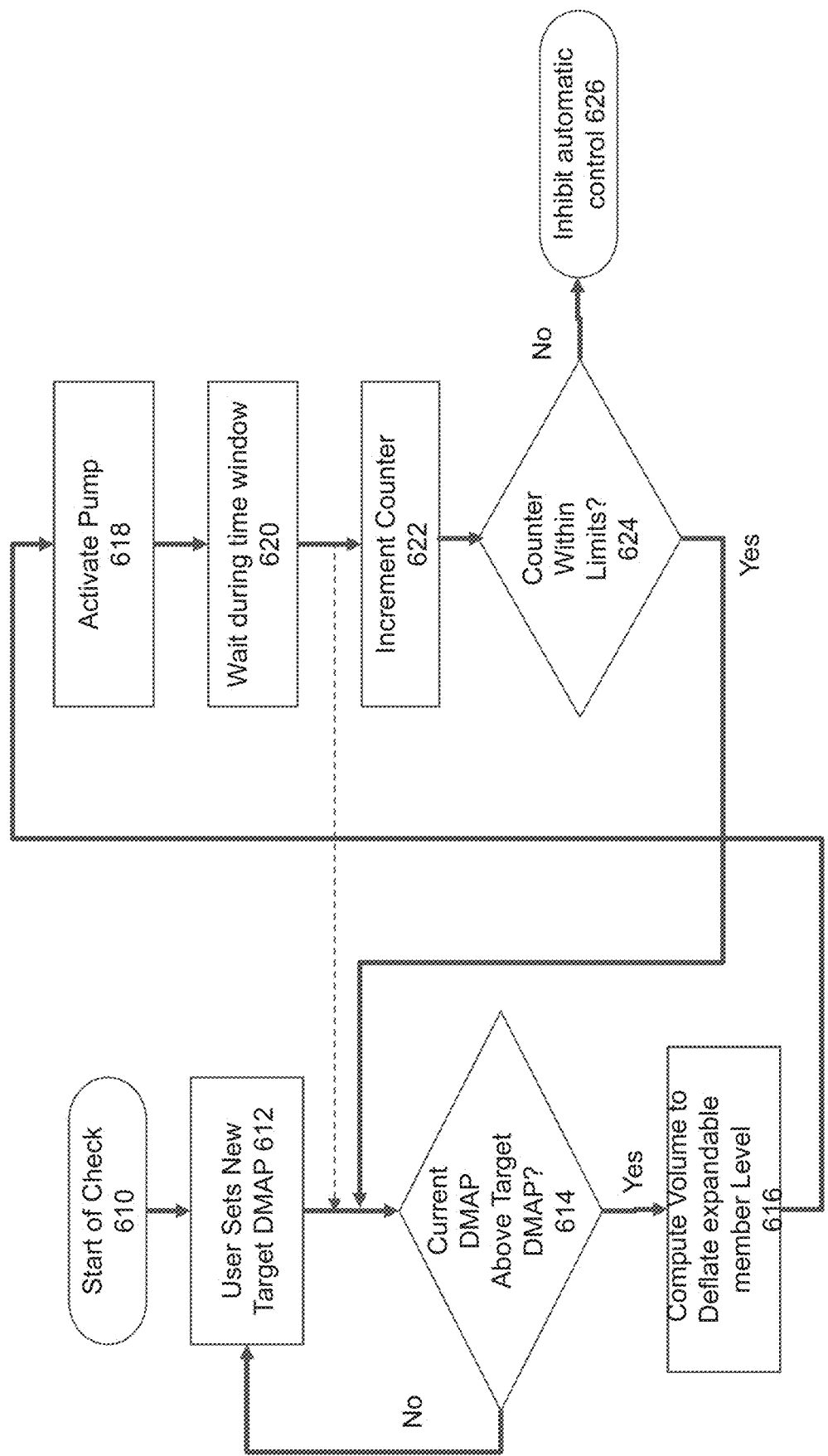
FIGS. 6A-6F are flow diagrams of exemplary variations of a physiologic check test.

FIG. 6A is a flow chart depicted an exemplary variation of detecting an error in a user-entered target DMAP. At step 612, the user sets the new target DMAP to a value that is higher than the current DMAP. At step 614, the system controller 106 may check if the new target DMAP is higher than the current DMAP, and if so, it may calculate the amount of fluid and/or compressed gas to be removed from the expandable member 110. At 616, based on the calculation, the system controller 106 may actuate the pump. At 620, the system controller 106 may wait for a predefined time period (e.g., about 60 seconds) to allow for the blood pressure to stabilize based on the new expandable member volume.

In some variations, instead of calculating the amount of fluid and/or compressed gas to be removed from the expandable member 110, the system controller 106 may determine a movement and/or or a position of the portion of the pump. The pump may be actuated (manually and/or automatically) accordingly to inject and/or remove the fluid and/or compressed gas until the new target DMAP is achieved. It should be readily appreciated that this variation may be implemented in scenarios where the expandable member is a non-fluid based expandable member (e.g., inflated and/or deflated using mechanical linkages, etc.) In some variations, instead of calculating an amount of fluid and/or a pump movement, the fluid and/or compressed gas may be injected and/or removed from the expandable member at a constant rate until the new target DMAP is achieved.

If the new target DMAP is too high, it may imply that the patient may be experiencing significant bleeding. In such a scenario, the new target DMAP may be difficult to achieve because the increased blood flow caused by the reduced expandable member volume will not result in the desired increase in the DMAP. As such, going from step 620 to 614 would result in repeated cycles of decreased expandable member volume, increased blood flow, and increased bleeding. This may result in the current DMAP not changing or current DMAP decreasing with subsequent decreases in expandable member volume.

To combat this situation, at step 622, the system controller 106 may initiate a counter. The counter may measure the number of automated inflations and/or deflations and may compare the number of automated steps (e.g., total inflations in a predetermined time, consecutive inflations, total deflations in a predetermined time, consecutive deflations, total inflations and deflations in a predetermined time) to a limit or range. The system controller 106 may also determine whether a corresponding increase in a blood pressure measurement (e.g., distal average pressure) has occurred. If the number of steps is below the limit and/or within the range, then the system controller 106 may maintain the system in the automatic mode. However, if the limit is exceeded and/or the number of steps is outside of the range, the system controller 106 may inhibit a function of the blood flow control system. For example, the system controller 106 may transition the blood from control system form the automated mode to the manual mode (step 626). In another variation, the system controller 106 may inhibit automated inflation/deflation of the expandable member (while maintain the volume of the expandable member) until user acknowledgment of the error (e.g., via an input of the user interface), at which point, the system controller 106 may allow for automated control.

In yet another variation, the system controller 106 may monitor the physiologic changes as the expandable member is automatically inflated and/or deflated. For repeated movements of the expandable member, the system controller 106 may identify a sequence of drops and/or increases in the blood pressure measurements. If the sequence of changes to the blood pressure measurements is outside an expected range, then the system controller 106 may inhibit a function of the blood flow control system. For example, the system controller 106 may transition the system from the automated mode to the manual mode (step 626). In another variation, the system controller 106 may inhibit automated inflation/deflation of the expandable member (while maintain the volume of the expandable member) until user acknowledgment of the error (e.g., via an input of the user interface), at which point, the system controller 106 may allow for automated control.

In some variations, the number of automated steps associated with step 624 may include the number of consecutive increases or decreases in the expandable member level, such as, for example, 5, 6, 7, 8, 9, 10 consecutive inflations or deflations (including all sub-ranges therein), without a corresponding decrease or increase in the distal average pressure. In other variations, this condition may be detected based on a ratio of inflations or deflations, such as, for example, 50% inflations, 60% inflations, 70% inflations, 80% inflations, or between about 50%-80% inflations, between about 60%-80% inflations, between about 70%-80% inflations, etc., resulting in no decrease or increase in the distal average pressure. In yet other variations, the condition may be detected based on the total volume of consecutive inflations or deflations rather than the number of inflations or deflations.

At step 626, the system controller 106 may inhibit further deflation of the expandable member 110 and may provide a warning (e.g., transmit an alert) to the user, e.g., via the user interface, that a lower target DMAP is recommended or that bleeding is predicted.

Excessive Bleeding

During the course of the procedure on the patient, the blood flow control system may continuously monitor the physiologic conditions (e.g., changes in blood pressures) of the patient. In some variations, such as after inflation of the expandable member to full occlusion (e.g., occlusion blood flow state), as the expandable member is deflated (e.g., using the pump), the expected response may be an increase in the DMAP and a slight decrease in the PMAP. However, if the DMAP does not increase, this may indicate that the expandable member is being deflated too fast and/or that the expandable member has been deflated too much for the particular patient's physiology at that time and that the patient may be excessively bleeding. In other instances, if PMAP drops rapidly, this may also indicate that the patient is excessively bleeding. If the system controller 106 detects conditions indicative of excessive bleeding, the system controller 106 may inhibit a function of the blood flow control system. For example, the system controller 106 may transition the blood flow control system from the automatic mode to the manual mode of operation. In another example, the system controller may inhibit further automatic deflation of the expandable member. Additionally or alternatively, the system controller 106 may simultaneously or substantially simultaneously transmit an alert to the user indicating excessive or ongoing bleeding.

Early Occlusion

During the course of the procedure on the patient, as the expandable member is inflated, the expected physiologic response from the patient may be an increase in PMAP but a decrease in DMAP. As the expandable member is inflated, the system controller 106 may monitor the physiologic conditions of the patient, such as, for example the DMAP. In some variations, a lower target DMAP may be set (e.g., using a user interface via input from a user and/or by the system controller itself) and the expandable member may continue to inflate in an attempt to achieve the lower target DMAP. For instance, the determined DMAP of the patient may be about 35 mmHg and target DMAP of about 10 mmHg may be set. As the expandable member is inflated to achieve the new target DMAP of 10 mmHg, the system controller 106 may monitor the blood flow state of the patient. In some situations, the system controller 106 may detect a blood flow state of Occlusion before reaching the target DMAP. In such situations, the system controller 106 may identify this condition, a blood flow state of Occlusion prior to reaching a target DMAP, and in response, may inhibit a function of the blood flow control system. For example, in some variations, the system controller 106 may transition the blood flow control system from the automatic mode to the manual mode of operation. In another example, the system controller 106 may inhibit further automatic inflation of the expandable member. Additionally or alternatively, the system controller 106 may simultaneously or substantially simultaneously transmit an alert to the user indicating early Occlusion.

Occlusion Time is Beyond Safe Limit (Unsafe Occlusion Time)

During the course of the procedure on the patient, the user may set a new target DMAP to achieve in a blood flow state of Occlusion, and then later, after obtaining hemorrhage control, may set a second, new, higher target DMAP to achieve partial flow. If bleeding is then discovered by the user, the user may set a third, new, lower target DMAP 148 to again achieve a blood flow state of Occlusion. As described above in relation to system measurements, the system controller 106 may determine a time at Occlusion during a treatment. During the course of the treatment, there may be multiple time windows of Occlusion and Flow. The system controller 106 may account for the various changes in blood flow control state and may determine a time at Occlusion and/or a time not at Occlusion. For example, the blood flow state might first be at occlusion for 20 minutes, then not at Occlusion for 5 minutes, then at Occlusion for 18 minutes, then not at Occlusion for 10 minutes, then at Occlusion for 15 minutes, and finally not at Occlusion for 30 minutes. In this example, the time at Occlusion is 43 minutes (20+18+15) and the time not at Occlusion is 45 minutes (5+10+30).

If any single time period at Occlusion, or the total time at Occlusion during an overall procedure is beyond a limit, damage to the patient may occur. This damage may include harm to the patient's internal organs, blood vessels, muscles, and/or other tissue. Accordingly, at least because it would require extra effort and resources for the user to have to separately keep track of the time at occlusion for each individual setting and because, it may be distracting for the user to have to keep track of these total times (as the individual time periods at occlusion may be separated by several minutes), the system controller 106 in the blood flow control systems described herein may track and/or calculate times associated with blood flow control states.

As discussed above, in some variations, the system controller 106 may determine total time elapsed, total time at Occlusion, and total time not at Occlusion. In some variations, the system controller 106 may determine if the total time at Occlusion has exceeded a safe limit based on the total time at Occlusion and/or the total time not at Occlusion. Additionally or alternatively, unsafe occlusion time may indicate duration of most recent uninterrupted time at occlusion.

Figure 6B:
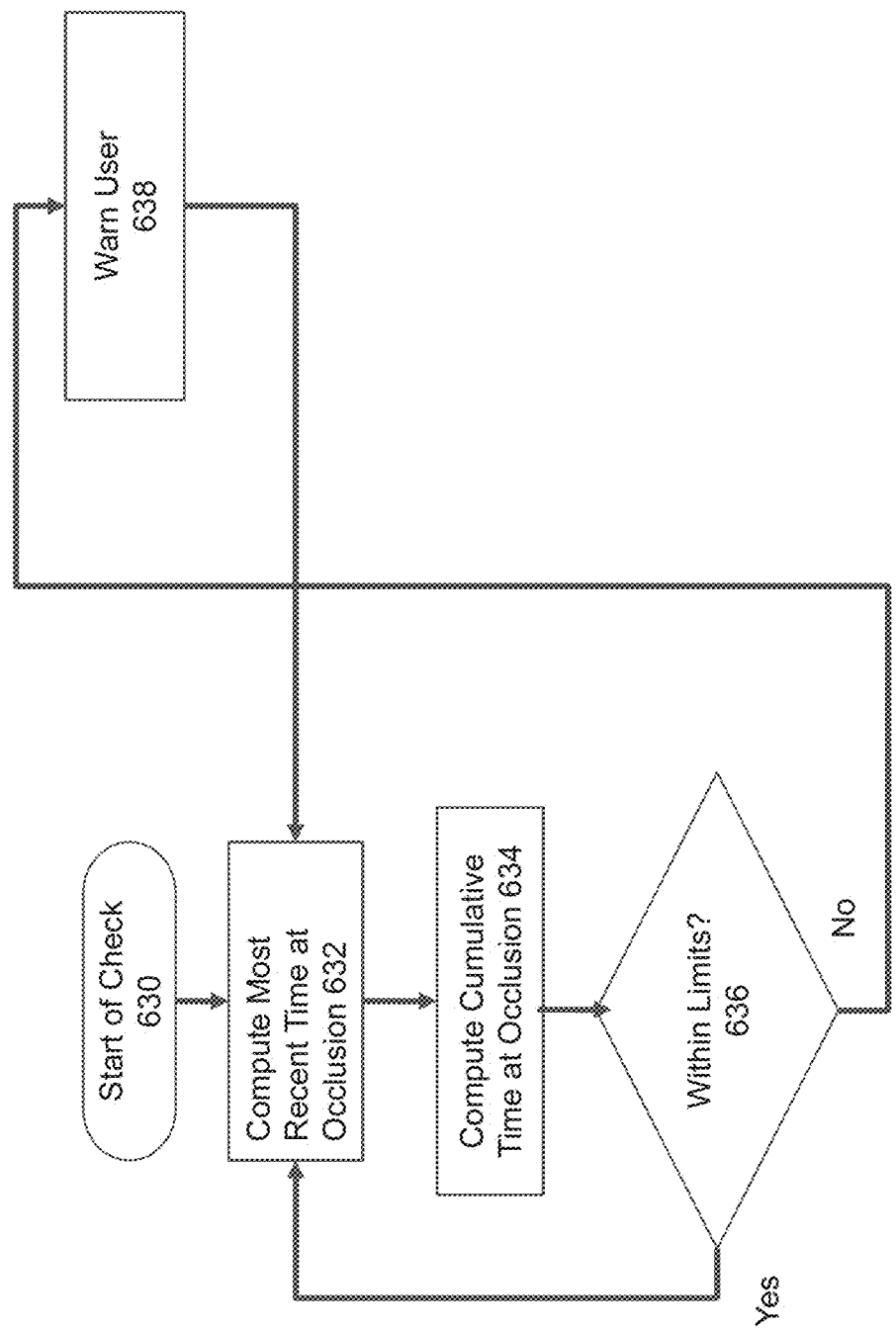

FIG. 6B illustrates a flow diagram associated with an exemplary variation of measuring the time at Occlusion and responding when it is longer than the amount considered safe for the patient. At step 632, the system controller 106 may determine the most recent period of time that the blood vessel has been occluded (e.g., based on blood flow state). At 634, the system controller 106 may determine a total time at Occlusion for the treatment. At step 636, the system controller 106 may compare the total time at Occlusion and/or the most recent period of time at Occlusion to target values and/or target ranges for each respectively. If the system controller 106 determines that one or more of the total time at Occlusion and the most recent period of time at Occlusion exceed their respective target values and/or fall outside their respective target ranges, (step 636), the system controller 106 may inhibit a function of the blood flow control system and/or transmit at warning (e.g., an alert) to the user, via, e.g., the user interface. For example, in some variations, the system controller 106 may transition the blood flow control system from the automatic mode to the manual mode. In another variation, the system controller 106 may inhibit automated inflation/deflation of the expandable member (while maintain the volume of the expandable member) until user acknowledgment of the error (e.g., via an input of the user interface), at which point, the system controller 106 may allow for automated control.

Temporary Physiologic Error

In some variations, when a target blood pressure (e.g., target DMAP) is changed, occlusion may be detected earlier than expected. For example, the pump 108 may inject fluid and/or compressed gas into the expandable member such that the volume of the expandable member may reach a volume (e.g., a threshold value) that corresponds to the target DMAP. However, as the pump injects the fluid and/or compressed gas, the volume of the expandable member may surpass a threshold value. Additionally or alternatively, an Occlusion state may be achieved before reaching the target blood pressure (e.g., target DMAP). This may be indicative of a temporary error condition. Upon detection of the temporary physiologic error, the system controller 106 may inhibit a function of the blood flow control system and/or may provide a warning (e.g., alert) to the user, via, e.g., the user interface. In some variations, the system controller may transition the system from the automatic mode to the manual mode. In another variation, the system controller 106 may inhibit automated inflation/deflation of the expandable member (while maintain the volume of the expandable member) until user acknowledgment of the error (e.g., via an input of the user interface), at which point, the system controller 106 may allow for automated control.

Figure 6C:
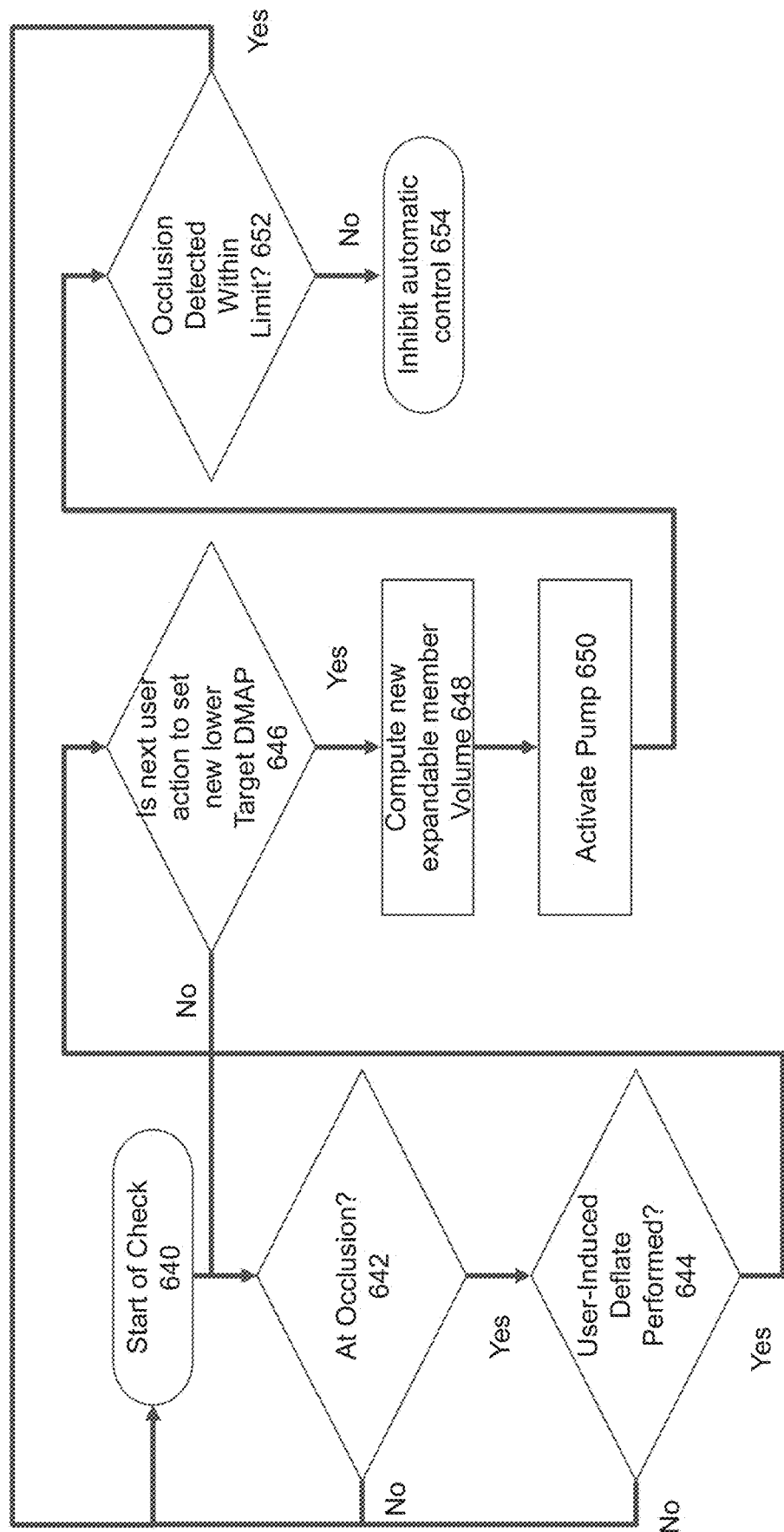

FIG. 6C illustrates a flow diagram associated with an exemplary variation of a temporary physiologic error that may occur when increasing and then reducing the Target DMAP, and occlusion is detected prior to the expected level. If at step 642, the blood flow state is not at Occlusion, then return to the start. At step 644, the system controller 106 may check if there is a user-induced reduction in the expandable member volume, either through manual actions (e.g., via the user interface) or by setting a higher target distal average pressure. At step 646, the system controller 106 may determine whether the next user input is setting a lower target distal average pressure. If the next user input is setting a lower target distal average pressure, system controller 106 may, at step 648, compute a new expandable member volume and activate the pump (step 650).

At step 652, the system controller 106 may determine whether the current expandable member volume plus a threshold value is greater than or equal to the last measured volume during an Occlusion state. If the Occlusion state is not detected, the patient's physiologic state may have significantly changed, and the system controller 106 may detect a temporary physiologic error (step 654). Upon detection of the temporary physiologic error, the system controller 106 may inhibit a function of the blood flow control system and/or may provide a warning (e.g., an alert) to a user via, e.g., the user interface. In some variations, the system controller 106 may transition the blood flow control system from the automated state to the manual state. In another variation, the system controller 106 may inhibit automated inflation/deflation of the expandable member (while maintain the volume of the expandable member) until user acknowledgment of the error (e.g., via an input of the user interface), at which point, the system controller 106 may allow for automated control.

Another system controller check may involve cases where setting a new target blood pressure (e.g., target DMAP) to a lower value, and the resulting inflation of the expandable member 110 results in a blood flow state of occlusion prior to achieving the target blood pressure. For example, if the blood flow state is not at occlusion and the current blood pressure value (e.g., current DMAP) is 20 mmHg, and the user selects a new target DMAP of 10 mmHg, the system controller may inflate the expandable member. During that inflation, if the blood flow state is at occlusion when the blood pressure value (e.g., DMAP) is 14 mmHg, then it might not be safe for the patient to keep inflating the expandable member, trying to achieve the target blood pressure value (e.g., target DMAP), since the blood flow state is already at occlusion.

Setting a New Target DMAP

In some variations, the system controller 106 may identify if a newly set target DMAP is too high or too low. For instance, if the system controller detects occlusion volume of the expandable member to be higher than the volume corresponding to the newly state target DMAP, it may be indicative of reaching occlusion state sooner than required. Accordingly, the system controller 106 may inhibit automatic inflation of the expandable member and may automatically set a new target DMAP that may be lower the previous target DMAP. In some variations, the system controller 106 may allow a user to set a new target DMAP via a user interface and may optionally provide an appropriate alert or warning to the user.

Figure 6D:
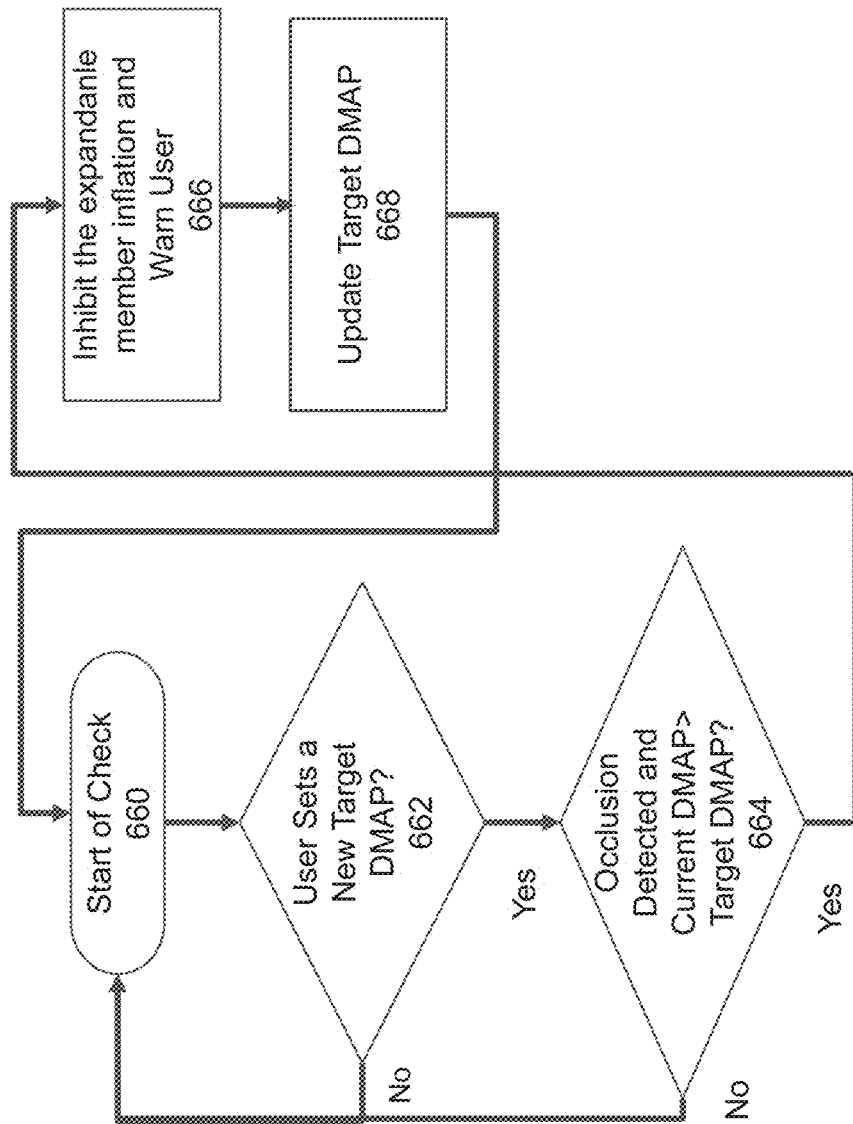

FIG. 6D illustrates a sequence where the user sets a new target DMAP at step 662. When the new target DMAP is lower than the current DMAP, the expandable member 110 is inflated. The check at step 664 looks for the case where the value is found to be lower than the current DMAP and occlusion is detected at a expandable member volume that is higher than the new target DMAP (plus some allowed threshold). If this occurs, then step 666 causes the system controller to inhibit the automatic inflation, warn the user via the User Interface, and automatically set a new Target DMAP.

Operating Thresholds

In some variations, the system controller 106 may determine whether a blood pressure measurement (e.g., a proximal average pressure) is above or below a safe operating threshold or outside of a safe operating range. Upon detection of a blood pressure measurement that is above/below a safe operating threshold and/or outside of safe operating range, the system controller 106 may inhibit a function of the blood flow control system and/or may provide a warning (e.g., an alert) to a user via, e.g., the user interface. For example, the system controller 106 may transition the blood flow control system from the automated mode to the manual mode. In another variation, the system controller 106 may inhibit automated inflation/deflation of the expandable member (while maintain the volume of the expandable member) until user acknowledgment of the error (e.g., via an input of the user interface), at which point, the system controller 106 may allow for automated control.

Figure 6E:
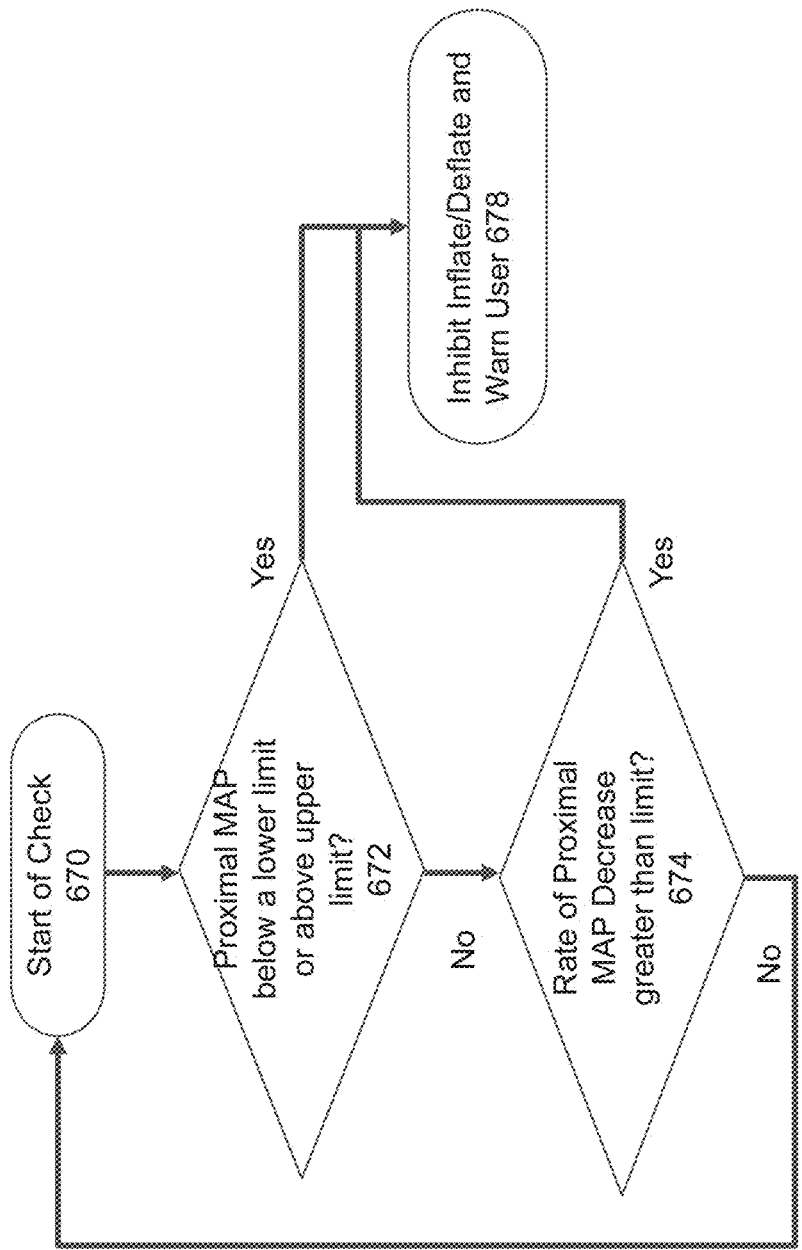

FIG. 6E illustrates a flow diagram of the checks for conditions where the absolute levels of the proximal average pressure are above or below safe operating thresholds, as well as rates of change in the proximal average pressure exceed thresholds. At step 672, the system controller 106 may examine the proximal average pressure to see if it is lower than an allowed lower limit or above an allowed upper limit. Similarly, at step 674 it checks if the rate of change in the proximal average pressure is greater than a limit. If the system controller determines that the threshold or limit has been exceeded, then at step 676, the system controller may provides a warning to the user and inhibits the automated inflate/deflate of the expandable member 110.

Identifying Cardiac Arrest

Figure 6F:
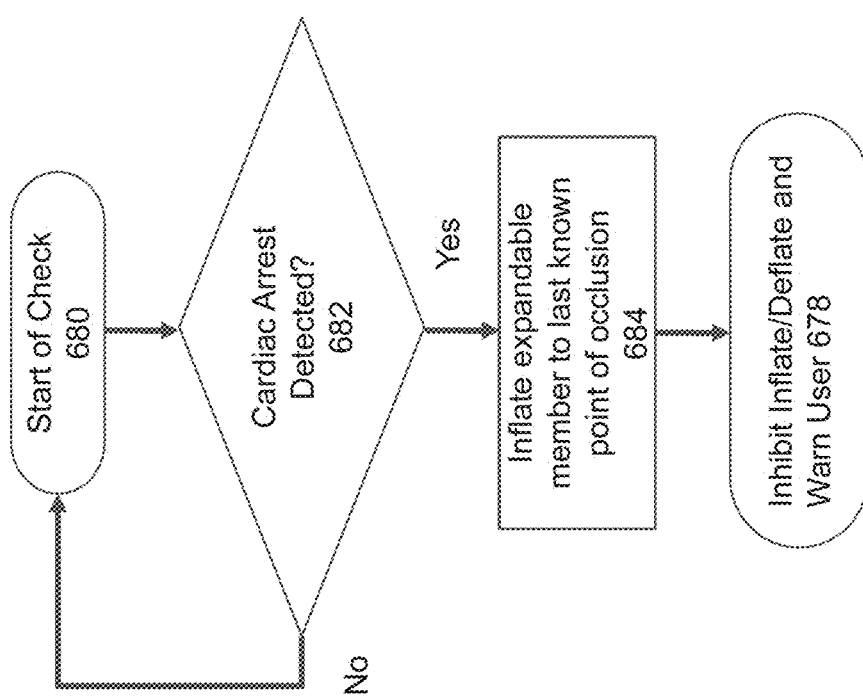

FIG. 6F shows the flow diagram of the system response to Cardiac Arrest. Cardiac arrest may be indicated by excess time between systolic peaks or diastolic troughs, and a significant drop in the mean arterial pressure. In some variations, upon the detection of cardiac arrest by the system controller 106, the system controller 106 may cause the expandable member 110 to inflate to the level at which a blood flow state of Occlusion was last detected.

Method for Controlling Blood Flow

Figure 7:
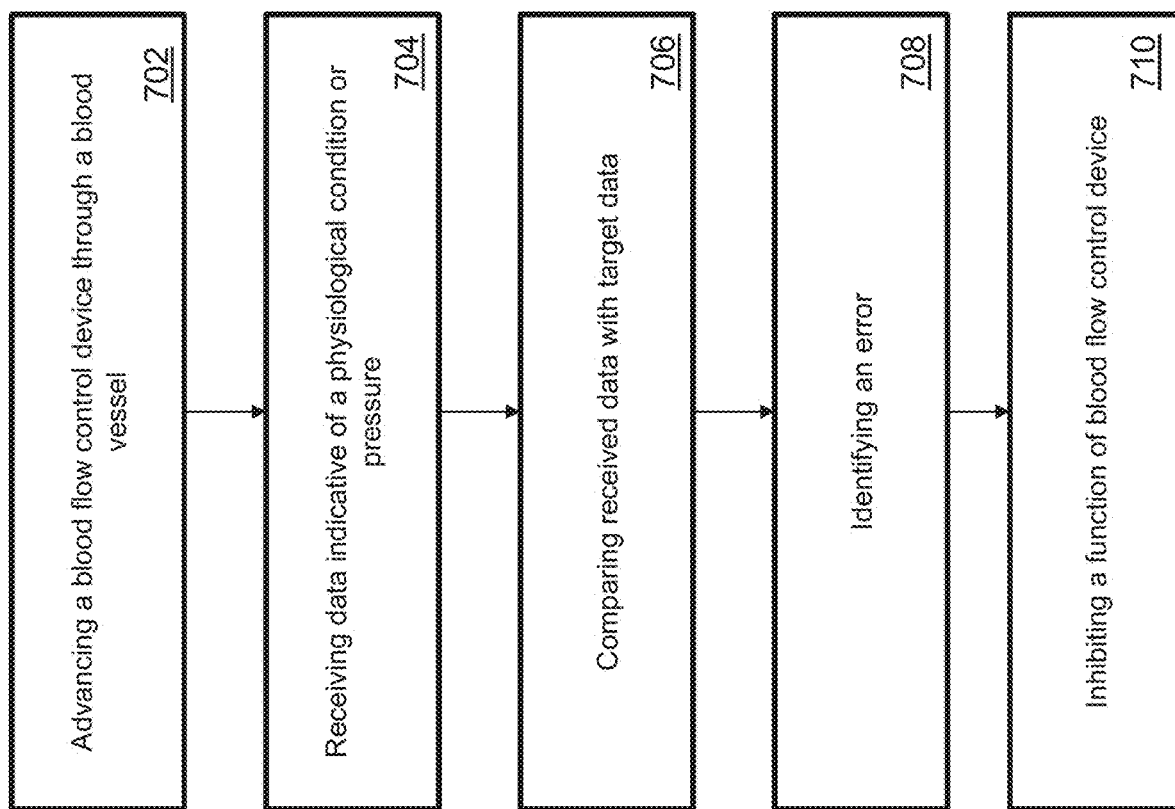
FIG. 7 is a flow diagram illustrating an exemplary variation of a method for controlling blood flow in a patient.

FIG. 7 is a flow diagram illustrating an exemplary variation of a method for controlling blood flow. In some variations, the method may include at 702, advancing a blood flow control device (e.g., structurally and/or functionally similar to blood flow control device 104 in FIG. 1) through a blood vessel. In some variations, the blood flow control device may include an elongate body (e.g., structurally and/or functionally similar to elongate body 102 in FIG. 1) and an expandable member (e.g., structurally and/or functionally similar to expandable member 110 in FIG. 1). The elongate body or a portion thereof (e.g., a tip or end portion) may be advanced to and inserted into a target blood vessel (e.g., the aorta) via a suitable endovascular route. For example, in variations in which the target blood vessel is the aorta, the end portion of the elongate body may be inserted into the aorta through the femoral artery. In some variations, the elongate body may be inserted into the aorta through radial access. The elongate body may be advanced such that the expandable member is positioned at a desired location in the aorta. For example, the elongate body may be advanced until the expandable member is positioned in zone 1 of the aorta, zone 2 of the aorta, or zone 3 of the aorta. Alternatively, the blood flow control device may be inserted into the iliac arteries and not advanced into the aorta.

Once the expandable member has been positioned in the desired location, the expandable member may be initially inflated manually by a user using the pump (i.e., without utilizing the controller(s)) to full occlusion (e.g., a blood flow state of Occlusion). The pump may then be coupled (or recoupled) to the controller(s), and the system may record this initial inflation level as the maximum allowable inflation level for the particular patient or procedure. For example, the system may record the position of the pump when the pump is coupled to the controller after initial inflation and may correlate this position to maximum allowable inflation level for the blood flow control system. During subsequent automatic operation, if the movement and/or position of the pump indicates an inflation level nearing or exceeding the maximum allowable inflation level, the method may include inhibiting a function of the blood flow control system, such as, for example, automatically transitioning the blood flow control system to a manual mode of operation.

In some variations, the blood flow control device may include at least one sensor. The at least one sensor may be any of the sensors described herein, such as, for example, one or more of a proximal pressure sensor, a distal pressure sensor, a flow sensor, an expandable member sensor, a barometer, and a position sensor (e.g., a magnetic encoder). A controller (e.g., system controller 106 in FIG. 1) may receive sensor data from the at least one sensor. The sensor data may be received after the blood flow control device has been powered on prior to advancing the blood flow control device through the vasculature, while inserting the blood flow control device, and/or during use of the blood flow control device.

At 704, the method may include receiving data indicative of a physiologic condition or expandable member pressure. Physiologic conditions may include, but are not limited to, one of and/or a combination of one or more of proximal systolic pressure, proximal diastolic pressure, PMAP, proximal pressure pulsitility, distal systolic pressure, distal diastolic pressure, DMAP, and distal pressure pulsitility. The expandable member pressure may be received from an expandable member sensor. In some variations, an expandable member volume may be derived from the expandable member pressure.

At 706, the method may include comparing the received data with target data. In some variations, the target data may be set by a user via a user interface. Alternatively, the controller may predict the target data based on analysis of prior data. In some variations, the target data may include threshold values. For example, the target data may include any of the threshold values described herein, such as, for example, threshold values for proximal systolic pressure, proximal diastolic pressure, PMAP, distal systolic pressure, distal diastolic pressure, DMAP, expandable member pressure, expandable member volume, total time at occlusion, etc. Alternatively, the target data may include any of the expected and/or predicted values described herein, such as, for example, expected and/or predicted values for proximal systolic pressure, proximal diastolic pressure, PMAP, proximal pressure pulsitility, distal systolic pressure, distal diastolic pressure, DMAP, distal pressure pulsitility, expandable member pressure, expandable member volume, total time at occlusion, etc.

At 708, the method may include identifying an error based on the comparison. The error may be any of the errors described herein, such as, for example an error indicative of one of and/or a combination of sensor damage, expandable member damage, low controller battery, high controller temperature, audio error, communications error, insertion sequence error, damping error, clotting error, noise due to electrical interference, pressure gradient error, one sensor reading being too high or too low, expandable member pressure not corresponding to pump movement, maximum inflation of expandable member, morphological changes to expandable member, error in target DMAP, occlusion time being beyond a safe limit, temporary physiologic errors, and identifying cardiac arrest.

At 710, the method may include inhibiting at least one function of the blood flow control system in response to identifying the error. In some variations, inhibiting the at least one function may include inhibiting automatic control of the expandable member. For instance, the blood flow control device may be automatically transitioned from an automatic mode of operation to a manual mode of operation. Some non-limiting examples of errors with this response may include: (i) error indicative of error in advancing the distal portion of the blood flow control device through the blood vessel (e.g., a function of PMAP and DMAP may be compared to a target value to identify this error); (ii) error indicative of clotting in the blood vessel (e.g., trend in proximal pulsitility and/or distal pulsatility may be compared to trend in expandable member pulsitility pressure to identify this error); and/or (iii) error indicative of electrical interference from another device (e.g., proximal blood pressure and distal blood pressure may be compared to one or more threshold values to identify this error).

In some variations, inhibiting the at least one function may include automatically shutting down the blood flow control system. Some non-limiting examples of errors with this response may include: (i) error may be indicative of damage to the sensor (e.g., proximal average pressure, distal average pressure and/or expandable member pressure may be compared to at least one threshold value to identify this error); (ii) error may be indicative of damage to an expandable member (e.g., expandable member pressure may be compared to a target value to identify this error); and/or (iii) error may be indicative of the expandable member having reached a maximum volume (e.g., the expandable member pressure may be compared to a target value to identify this error).

Additionally or alternatively to inhibiting at least one function of the blood flow control system, the method may include transmitting an alert to a user via a user interface. Some non-limiting examples of errors with this response may include: (i) error may be indicative of error in target data (e.g., the proximal systolic pressure may be compared to a target data and the alert may include instructions to change the target data); or (ii) error may be indicative of an unsafe occlusion time (e.g., the occlusion time may be compared to a first target value and the distal systolic pressure may be compared to a second target value). In some variations, unsafe occlusion time may indicate total time at occlusion. Additionally or alternatively, unsafe occlusion time may indicate duration of most recent uninterrupted time at occlusion.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

The invention claimed is:

1. A blood flow control system comprising:
a blood flow control device for placement within a body of a patient, the blood flow control device comprising an expandable member, a proximal sensor proximal to the expandable member, and a distal sensor distal to the expandable member, wherein each of the proximal and distal sensors is configured to measure a physiologic condition of the patient; and
one or more controllers communicably coupled to each of the proximal and distal sensors and configured to:
receive data indicative of the physiologic condition of the patient from the proximal and distal sensors;
compare the received data with target data;
identify at least one error based on the comparison; and
in response to identifying the error, inhibit at least one function of the blood flow control system,
wherein the received data is proximal blood pressure from the proximal sensor and distal blood pressure from the distal sensor, and the one or more controllers is further configured to compare at least one of the proximal blood pressure and the distal blood pressure to a target value.

2. The blood flow control system of claim 1, wherein the system further comprises a pump to control a volume of the expandable member.

3. The blood flow control system of claim 1, wherein the at least one function comprises automatic control of the expandable member.

4. The blood flow control system of claim 3, wherein the one or more controllers is configured to inhibit automatic control of the expandable member by transitioning the blood flow control system from an automatic mode of operation to a manual mode of operation.

5. The blood flow control system of claim 1, wherein the at least one error indicates an error in the placement of the blood flow control device.

6. The blood flow control system of claim 1, wherein the proximal blood pressure is proximal mean arterial pressure from the proximal sensor and the distal blood pressure is distal mean arterial pressure from the distal sensor, and
the one or more controllers is further configured to compare at least one of the proximal mean arterial pressure and the distal mean arterial pressure to a target value.

7. The blood flow control system of claim 1, wherein the at least one error indicates electrical interference from another device.

8. The blood flow control system of claim 7, wherein
the one or more controllers is further configured to compare the proximal blood pressure to a first threshold value and the distal blood pressure to a second threshold value.

9. The blood flow control system of claim 7, wherein:
the received data further comprises a heart rate of the patient, and
the one or more controllers is further configured to compare the heart rate to a target heart rate range.

10. The blood flow control system of claim 7, wherein in response to the electrical interference exceeding a threshold time, the one or more controllers is configured to transition the blood flow control system to the manual mode.

11. The blood flow control system of claim 1, wherein the at least one error indicates an error in pressure gradient between the proximal sensor and the distal sensor.

12. The blood flow control system of claim 11, wherein:
the proximal blood pressure is proximal mean arterial pressure from the proximal sensor and the distal blood pressure is distal mean arterial pressure from the distal sensor, and
the one or more controllers is further configured to compare distal pulsatility to a target distal pulsatility.

13. The blood flow control system of claim 1, wherein:
the error indicates an error in functionality with at least one of the proximal sensor and the distal sensor.

14. The blood flow control system of claim 13, wherein:
the received data is proximal mean arterial pressure from the proximal sensor and distal mean arterial pressure from the distal sensor, and
the one or more controllers is further configured to compare the proximal mean arterial pressure to the distal mean arterial pressure.

15. The blood flow control system of claim 1, wherein the one or more controllers is configured to inhibit the at least one function by shutting down the blood flow control system.

16. The blood flow control system of claim 1, wherein the error indicates damage to the sensor.

17. The blood flow control system of claim 16, wherein:
the received data further comprises expandable member pressure, and
the one or more controllers is further configured to compare at least one of the proximal blood pressure, the distal blood pressure, and the expandable member pressure to at least one target value.

18. The blood flow control system of claim 1, wherein the error indicates damage to the expandable member.

19. The blood flow control system of claim 18, wherein the received data further comprises expandable member pressure and the one or more controllers is further configured to compare the expandable member pressure to a target value.

20. The blood flow control system of claim 1, wherein the error indicates that the expandable member has reached a maximum volume.

21. The blood flow control system of claim 20, wherein:
the received data further comprises expandable member pressure, and
the one or more controllers is further configured to compare the expandable member pressure to a maximum threshold value.

22. The blood flow control system of claim 1, wherein the system further comprises a user interface communicably coupled to the one or more controllers.

23. The blood flow control system of claim 22, wherein the one or more controllers is further configured to transmit an alert to a user via the user interface.

24. The blood flow control system of claim 23, wherein the target data comprises a user-inputted target value, and wherein the alert indicates an error in the target value.

25. The blood flow control system of claim 24, wherein:
the received data further comprises proximal systolic blood pressure, and
the one or more controllers is configured to compare the proximal systolic blood pressure to the target value.

26. The blood flow control system of claim 1, wherein the one or more controllers is further configured to:
initiate a counter to determine a number of automatic inflations of the expandable member, and
compare the number of automatic inflations to reach a target value to a threshold count, the target value indicating a target blood pressure measurement.

27. The blood flow control system of claim 1, wherein the one or more controllers is further configured to:
initiate a counter to determine a number of automatic deflations of the expandable member, and
compare the number of automatic deflations to reach a target value to a threshold count, the target value indicating a target blood pressure measurement.

28. The blood flow control system of claim 23, wherein the alert indicates an unsafe occlusion time.

29. The blood flow control system of claim 28, wherein the unsafe occlusion time is based on a total time at occlusion.

30. The blood flow control system of claim 28, wherein the unsafe occlusion time is based on a duration of most recent uninterrupted time at occlusion.

31. A method for controlling blood flow in a patient, the method comprising:
advancing a blood flow control device through a blood vessel of a patient, wherein the blood flow control device comprises an expandable member and a proximal sensor proximal to the expandable member, and a distal sensor distal to the expandable member;
receiving, from each of the proximal and distal sensors, data indicative of a physiologic condition of the patient;
comparing the received data with target data;
identifying at least one error based on the comparison; and
in response to identifying the error, inhibiting at least one function of the blood flow control device,
wherein the received data is proximal blood pressure from the proximal sensor and distal blood pressure from the distal sensor.

32. A blood flow control system comprising:
a blood flow control device configured to be placed within a portion of a body of a patient, wherein the blood flow control device comprises an expandable member and a proximal sensor proximal to the expandable member, and a distal sensor distal to the expandable member;
a pump operably coupled to the expandable member; and
one or more controllers communicably coupled to the blood flow control device and the pump, the one or more controllers configured to:
automatically control inflation of the expandable member using the pump in an automatic mode based on proximal blood pressure data from the proximal sensor and distal blood pressure data from the distal sensor;
identify an error in the blood flow control system; and
upon identification of the error, automatically transition the blood flow control system from the automatic mode to a manual mode so as to inhibit automatic control of the expandable member with the one or more controllers.

33. The method of claim 31, wherein the proximal blood pressure is proximal mean arterial pressure and the distal blood pressure is distal mean arterial pressure.

34. The method of claim 31, wherein the identified error is an error in the placement of the blood flow control device.

35. The method of claim 31, wherein the identified error indicates an electrical interference from another device.

36. The method of claim 31, wherein the identified error is an error in a pressure gradient between the proximal sensor and the distal sensor.

37. The method of claim 31, wherein the error indicates an error in functionality with at least one of the proximal sensor and the distal sensor.

38. The method of claim 31, wherein the error indicates damage to the sensor.

39. The blood flow control system of claim 32, wherein the proximal blood pressure data is proximal mean arterial pressure data from the proximal sensor and the distal blood pressure data is distal mean arterial pressure data from the distal sensor.

\* \* \* \* \*